US009580752B2

(12) United States Patent
Rotter et al.

(10) Patent No.: US 9,580,752 B2
(45) Date of Patent: Feb. 28, 2017

(54) METHODS OF PREDICTING MEDICALLY REFRACTIVE ULCERATIVE COLITIS (MR-UC) REQUIRING COLECTOMY

(75) Inventors: Jerome I. Rotter, Los Angeles, CA (US); Kent D. Taylor, Ventura, CA (US); Stephan R. Targan, Santa Monica, CA (US); Talin Haritunians, Encino, CA (US); Dermot P. McGovern, Los Angeles, CA (US); Xiuqing Guo, Santa Monica, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 81 days.

(21) Appl. No.: 13/140,874

(22) PCT Filed: Dec. 24, 2009

(86) PCT No.: PCT/US2009/069531

§ 371 (c)(1), (2), (4) Date: Nov. 16, 2011

(87) PCT Pub. No.: WO2010/075579

PCT Pub. Date: Jul. 1, 2010

(65) Prior Publication Data

US 2012/0053131 A1 Mar. 1, 2012

Related U.S. Application Data

(60) Provisional application No. 61/140,794, filed on Dec. 24, 2008, provisional application No. 61/182,598, filed on May 29, 2009.

(51) Int. Cl.
*C12Q 1/68* (2006.01)

(52) U.S. Cl.
CPC ...... *C12Q 1/6883* (2013.01); *C12Q 2600/118* (2013.01); *C12Q 2600/156* (2013.01); *G01N 2800/067* (2013.01)

(58) Field of Classification Search
None
See application file for complete search history.

(56) References Cited

U.S. PATENT DOCUMENTS 3,654,090 A 4/1972 Schuurs
3,850,752 A 11/1974 Schuurs et al.
4,016,043 A 4/1977 Schuurs et al.
4,265,823 A 5/1981 Nobile
4,698,195 A 10/1987 Okumura et al.
4,699,880 A 10/1987 Goldtein
4,704,692 A 11/1987 Ladner
4,800,159 A 1/1989 Mullis et al.
4,880,548 A 11/1989 Pall et al.
4,925,572 A 5/1990 Pall et al.
4,935,234 A 6/1990 Todd et al.
5,002,873 A 3/1991 St. John et al.
5,085,318 A 2/1992 Leverick
5,091,302 A 2/1992 Newman et al.
5,114,842 A 5/1992 Plow et al.
5,137,806 A 8/1992 Lemaistre et al.
5,147,637 A 9/1992 Wright et al.
5,210,015 A 5/1993 Gelfand et al.
5,219,997 A 6/1993 Scholssman et al.
5,227,369 A 7/1993 Rosen et al.
5,234,810 A 8/1993 Kehrli, Jr. et al.
5,235,049 A 8/1993 McClelland et al.
5,236,081 A 8/1993 Fitzsimmons et al.
5,264,554 A 11/1993 Newman
5,272,263 A 12/1993 Hession et al.
5,284,931 A 2/1994 Springer et al.
5,491,063 A 2/1996 Fisher et al.
5,494,920 A 2/1996 Glasebrook et al.
5,518,488 A 5/1996 Schluger
5,590,769 A 1/1997 Lin
5,683,698 A 11/1997 Chavalli et al.
5,691,151 A 11/1997 Braun et al.
5,750,355 A 5/1998 Targan et al.
5,830,675 A 11/1998 Targan et al.
5,840,300 A 11/1998 Williams et al.
5,874,233 A 2/1999 Targan et al.
5,916,748 A 6/1999 Targan et al.
5,937,862 A 8/1999 Targan et al.
5,942,390 A 8/1999 Comminelli et al.

(Continued)

FOREIGN PATENT DOCUMENTS

AU 698604 2/1999
EP 0 760 010 B1 10/2002

(Continued)

OTHER PUBLICATIONS

Business Wire. Apr. 26, 2007, available via url: <businesswire.com/news/home/20070426005381/en/Illumina-Infinium-BeadChips-Selected-Germanys-National-Genome>.*
Hirschhorn et al. Genetics in Medicine. vol. 4, No. 2, pp. 45-61, Mar. 2002).*
Hattersley et al. The Lancet. 2005. 366: 1315-1323.*
Lucentini et al The Scientist (2004) vol. 18, p. 20.*
Magalhaes et al. Inflammatory Bowel Diseases. Oct. 208. 15: 353-358.*
Mummidi et al. Journal of Biological Chemistry 2000 vol. 275 No. 25 pp. 18946-18961.*
Halushka et al. Nature. Jul. 1999. 22: 239-247.*
Bagnoli et al (Inflammatory Bowel Diseases. 2006. 10: 705-708.*
Australia Office Action in App. No. 2005314089 dated Jul. 8, 2010 (Exhibit 56).
Australia Office Action in App. No. 26384/95 dated Sep. 19, 1997 (Exhibit 57).

(Continued)

*Primary Examiner* — Carla Myers
(74) *Attorney, Agent, or Firm* — Nixon Peabody LLP

(57) ABSTRACT

Disclosed are methods of predicting the development of medically refractory ulcerative colitis (MR-UC) in a patient In one embodiment, disclosed is a method of prognosing ulcerative colitis in an individual by determining the presence or absence of one or more risk variants, where the presence of one or more risk variants is indicative of a severe and/or aggressive form of ulcerative colitis. In another embodiment, the severe form of ulcerative colitis is indicative of MR-UC.

6 Claims, 17 Drawing Sheets

(56) References Cited

U.S. PATENT DOCUMENTS

| | | | |
|---|---|---|---|
| 5,947,281 | A | 9/1999 | Kaneff |
| 5,968,741 | A | 10/1999 | Pievy et al. |
| 6,034,102 | A | 3/2000 | Aiello |
| 6,074,835 | A | 6/2000 | Braun et al. |
| 6,114,395 | A | 9/2000 | Aiello |
| 6,183,951 | B1 | 2/2001 | Plevy et al. |
| 6,348,316 | B1 | 2/2002 | Taylor et al. |
| 6,376,176 | B1 | 4/2002 | Taylor et al. |
| 6,406,701 | B1 | 6/2002 | Pulido-Cejundo |
| 6,692,916 | B2 | 2/2004 | Bevilacqua et al. |
| 6,858,391 | B2 | 2/2005 | Nunez et al. |
| 6,869,762 | B1 | 3/2005 | Daly et al. |
| 7,138,237 | B1 | 11/2006 | Targan et al. |
| 7,252,971 | B2 | 8/2007 | Benson et al. |
| 7,332,156 | B2 | 2/2008 | Bowman et al. |
| 7,332,631 | B2 | 2/2008 | Hogarth et al. |
| 7,361,733 | B2 | 4/2008 | Hershberg et al. |
| 7,759,079 | B2 | 7/2010 | Oh et al. |
| 2001/0006789 | A1 | 7/2001 | Maino et al. |
| 2002/0006613 | A1 | 1/2002 | Shyjan et al. |
| 2002/0048566 | A1 | 4/2002 | El-Diery et al. |
| 2002/0106684 | A1 | 8/2002 | Kopreski |
| 2002/0150939 | A1 | 10/2002 | Taylor et al. |
| 2002/0198371 | A1 | 12/2002 | Wang et al. |
| 2003/0092019 | A1 | 5/2003 | Meyer et al. |
| 2003/0129215 | A1 | 7/2003 | Mollison et al. |
| 2003/0138781 | A1 | 7/2003 | Whitehead |
| 2003/0148345 | A1 | 8/2003 | Kopreski |
| 2003/0176409 | A1 | 9/2003 | Offner |
| 2003/0198640 | A1 | 10/2003 | Yu et al. |
| 2004/0053262 | A1 | 3/2004 | Lu |
| 2004/0181048 | A1 | 9/2004 | Wang |
| 2004/0203076 | A1 | 10/2004 | Targan et al. |
| 2004/0213761 | A1 | 10/2004 | Bowman et al. |
| 2004/0291555 | | 11/2004 | VanHeel |
| 2004/0265864 | A1 | 12/2004 | Mitsuhashi |
| 2005/0054021 | A1 | 3/2005 | Targan et al. |
| 2005/0143333 | A1 | 6/2005 | Richards et al. |
| 2005/0163764 | A1 | 7/2005 | Medzhitov et al. |
| 2005/0182007 | A1 | 8/2005 | McSwiggen et al. |
| 2005/0261219 | A1 | 11/2005 | Richards et al. |
| 2006/0003392 | A1 | 1/2006 | Oh et al. |
| 2006/0067936 | A1 | 3/2006 | Benson et al. |
| 2006/0141478 | A1 | 6/2006 | Brant et al. |
| 2006/0154276 | A1 | 7/2006 | Lois et al. |
| 2006/0211020 | A1 | 9/2006 | Farrer et al. |
| 2007/0037165 | A1 | 2/2007 | Venter et al. |
| 2007/0059758 | A1 | 3/2007 | Levine et al. |
| 2007/0072180 | A1 | 3/2007 | Abreu et al. |
| 2007/0196835 | A1 | 8/2007 | Bankaitis-Davis et al. |
| 2007/0254850 | A1 | 11/2007 | Lieberman et al. |
| 2007/0275424 | A1 | 11/2007 | Gewirtz et al. |
| 2008/0038831 | A1 | 2/2008 | Benson et al. |
| 2008/0081822 | A1 | 4/2008 | Berry et al. |
| 2008/0091471 | A1 | 4/2008 | Michon et al. |
| 2008/0095775 | A1 | 4/2008 | Lewis et al. |
| 2008/0103180 | A1 | 5/2008 | Fleming et al. |
| 2008/0108713 | A1 | 5/2008 | Begovich et al. |
| 2008/0131887 | A1 | 6/2008 | Stephan et al. |
| 2008/0206762 | A1 | 8/2008 | Ferrer Abizanda et al. |
| 2008/0261207 | A1 | 10/2008 | Mitsuhashi |
| 2008/0293582 | A1 | 11/2008 | Li et al. |
| 2009/0048119 | A1* | 2/2009 | Krjutskov et al. ................ 506/9 |
| 2009/0099789 | A1 | 4/2009 | Stephan et al. |
| 2009/0181380 | A1 | 7/2009 | Belouchi et al. |
| 2009/0253133 | A1 | 10/2009 | Mitsuhashi et al. |
| 2009/0297563 | A1 | 12/2009 | Borglum et al. |
| 2010/0015156 | A1 | 1/2010 | Dubinsky et al. |
| 2010/0021455 | A1 | 1/2010 | Targan et al. |
| 2010/0021917 | A1 | 1/2010 | Rotter et al. |
| 2010/0055700 | A1 | 3/2010 | Targan et al. |
| 2010/0099092 | A1* | 4/2010 | Song et al. ....................... 435/6 |
| 2010/0105044 | A1 | 4/2010 | Fleshner et al. |
| 2010/0144903 | A1 | 6/2010 | Taylor et al. |
| 2010/0184050 | A1 | 7/2010 | Rotter et al. |
| 2010/0190162 | A1 | 7/2010 | Rotter et al. |
| 2010/0240043 | A1 | 9/2010 | Rotter et al. |
| 2010/0284999 | A1 | 11/2010 | Taylor et al. |
| 2011/0033486 | A1 | 2/2011 | Abbas et al. |
| 2011/0124644 | A1 | 5/2011 | Targan et al. |
| 2011/0177969 | A1 | 7/2011 | Rotter et al. |
| 2011/0189685 | A1 | 8/2011 | Taylor et al. |
| 2011/0229471 | A1 | 9/2011 | Rotter et al. |
| 2012/0053131 | A1 | 3/2012 | Rotter et al. |
| 2013/0012604 | A1 | 1/2013 | Rotter et al. |
| 2014/0037618 | A1 | 2/2014 | Pidasheva et al. |

FOREIGN PATENT DOCUMENTS

| | | | | |
|---|---|---|---|---|
| EP | 1 285 271 B1 | | 8/2005 | |
| EP | 1 243 274 B1 | | 6/2008 | |
| EP | 1 819 827 B1 | | 8/2010 | |
| EP | 2 270 512 A1 | | 1/2011 | |
| WO | WO 91-16928 | | 4/1991 | |
| WO | WO 92-02819 | | 2/1992 | |
| WO | WO 92-22323 | | 6/1992 | |
| WO | WO 93-07485 | | 4/1993 | |
| WO | WO 93-12248 | | 6/1993 | |
| WO | WO 94-04188 | | 3/1994 | |
| WO | WO 95-21941 | | 8/1995 | |
| WO | WO 95-31575 | | 11/1995 | |
| WO | WO 97-25445 | | 7/1997 | |
| WO | WO 98-47004 | | 4/1998 | |
| WO | WO 00-76492 | | 12/2000 | |
| WO | WO 01-20036 | | 3/2001 | |
| WO | WO 03-040404 | | 5/2003 | |
| WO | WO 03-053220 | | 7/2003 | |
| WO | WO 03-059333 | | 7/2003 | |
| WO | WO 03-090694 | | 11/2003 | |
| WO | WO 03-099312 | | 12/2003 | |
| WO | WO 2004-020968 | | 3/2004 | |
| WO | WO 2004-031159 | | 4/2004 | |
| WO | WO 2004-048600 | | 6/2004 | |
| WO | WO 2005-044792 | | 5/2005 | |
| WO | WO 2005-114469 | | 12/2005 | |
| WO | WO 2005-115115 | | 12/2005 | |
| WO | WO 2005-116251 | | 12/2005 | |
| WO | WO 2006-063093 | | 6/2006 | |
| WO | WO 2006/075254 | * | 7/2006 | ............... C12Q 1/68 |
| WO | WO 2006-110091 | | 10/2006 | |
| WO | WO 2006-116721 | | 11/2006 | |
| WO | WO 2007-025989 | | 3/2007 | |
| WO | WO 2007-117611 | | 10/2007 | |
| WO | WO 2008-048984 | | 4/2008 | |
| WO | WO 2008-101133 | | 8/2008 | |
| WO | WO 2008-106451 | | 9/2008 | |
| WO | WO 2008-106579 | | 9/2008 | |
| WO | WO 2008-109782 | | 9/2008 | |
| WO | WO 2008-112990 | | 9/2008 | |
| WO | WO 2008-116150 | | 9/2008 | |
| WO | WO 2008-134569 | | 11/2008 | |
| WO | WO 2008-137762 | | 11/2008 | |
| WO | WO 2008-141148 | | 11/2008 | |
| WO | WO 2009-052512 | | 4/2009 | |
| WO | WO 2009-143278 | | 11/2009 | |
| WO | WO 2010-039931 | | 4/2010 | |
| WO | WO 2010-048415 | | 4/2010 | |
| WO | WO 2010-062960 | | 6/2010 | |
| WO | WO 2010-075579 | | 7/2010 | |
| WO | WO 2010-075584 | | 7/2010 | |
| WO | WO 2011-017120 | | 2/2011 | |
| WO | WO 2011-088237 | | 7/2011 | |
| WO | WO 2011-088306 | | 7/2011 | |
| WO | WO 2011-088380 | | 7/2011 | |
| WO | 2011116111 A1 | | 9/2011 | |
| WO | 2015168699 A1 | | 11/2015 | |

OTHER PUBLICATIONS

Australia Office Action in App. No. 13576/1997 dated Sep. 7, 2000 (Exhibit 58).

Australia Office Action in App. No. 13576/1997 dated Jul. 20, 2000 (Exhibit 59).

(56) References Cited

OTHER PUBLICATIONS

Australia Office Action in App. No. 13576/1997 dated Jul. 7, 1999 (Exhibit 60).
Canada Office Action in App. No. 13576/97 dated Jul. 7, 1999 (Exhibit 61).
Canada Office Action in App. No. 2,183,147 dated Jun. 20, 2007 (Exhibit 62).
Canada Office Action in App. No. 2,183,147 dated Mar. 20, 2006 (Exhibit 63).
Canada Office Action in App. No. 2,183,147 dated Apr. 1, 2005 (Exhibit 64).
Canada Office Action in App. No. 2,589,746 dated May 9, 2011 (Exhibit 65).
Canada Office Action in App. No. 2,589,746 dated Aug. 3, 2010 (Exhibit 66).
Europe Office Action in 05 853 294 dated May 8, 2008 (Exhibit 67).
ISR for EP application 2006772657 (Exhibit 68).
European Search Report in 05 85 3294 dated Apr. 29, 2008 (Exhibit 69).
European Search Report in 1 017 1757 dated Nov. 10, 2010 (Exhibit 70).
European Search Report in 95 921 264.8 dated Feb. 24, 1999 (Exhibit 71).
European Search Report in 95 921 264.8 dated Feb. 29, 2000 (Exhibit 72).
Further Examination Report in 05 85 3294 dated Apr. 30, 2009 (Exhibit 73).
IPER for PCT/US1995/001434 dated May 22, 1996 (Exhibit 74).
IPER for PCT/US1995/06107 dated May 6, 1996 (Exhibit 75).
IPER for PCT/US2000/025112 dated Dec. 20, 2001 (Exhibit 76).
IPER for PCT/US2003/023926 dated Aug. 19, 2004 (Exhibit 77).
IPER for PCT/US2005/044335 dated Jun. 13, 2007 (Exhibit 78).
IPRP for PCT/US2008/057820 dated Sep. 11, 2009 (Exhibit 79).
IPRP for PCT/US2008/063202 dated Sep. 11, 2009 (Exhibit 80).
IPRP for PCT/US1997/00042 dated Apr. 1, 1998 (Exhibit 81).
IPRP for PCT/US2005/018161 dated Jun. 4, 2008 (Exhibit 82).
IPRP for PCT/US2007/008597 dated Oct. 8, 2008 (Exhibit 83).
IPRP for PCT/US2008/057028 dated Sep. 15, 2009 (Exhibit 84).
IPRP for PCT/US2008/054033 dated Aug. 21, 2008 (Exhibit 85).
IPRP for PCT/US2008/055020 dated Aug. 26, 2009 (Exhibit 86).
IPRP for PCT/US2008/055236 dated Sep. 1, 2009 (Exhibit 87).
IPRP for PCT/US2008/056103 dated Sep. 3, 2008 (Exhibit 88).
IPRP for PCT/US2008/061652 dated Dec. 1, 2008 (Exhibit 89).
IPRP for PCT/US2008/062531 dated Nov. 10, 2009 (Exhibit 90).
IPRP for PCT/US2008/080526 dated Apr. 20, 2010 (Exhibit 91).
IPRP for PCT/US2009/044720 dated Nov. 23, 2010 (Exhibit 92).
IPRP for PCT/US2009/059190 dated Apr. 5, 2011 (Exhibit 93).
IPRP for PCT/US2009/061698 dated Apr. 26, 2011 (Exhibit 94).
IPRP for PCT/US2009/065928 dated May 31, 2011 (Exhibit 95).
IPRP for PCT/US2009/069531 dated Jun. 29, 2011 (Exhibit 96).
IPRP for PCT/US2009/069541 dated Jun. 29, 2011 (Exhibit 97).
ISR for PCT/2008/057820 dated Sep. 11, 2008 (Exhibit 98).
ISR for PCT/2008/063202 dated Nov. 18, 2008 (Exhibit 99).
ISR for PCT/US1995/01434 dated Jul. 21, 1995 (Exhibit 100).
ISR for PCT/US1995/06107 dated Jun. 10, 1995 (Exhibit 101).
ISR for PCT/US1997/00042 dated Apr. 21, 1997 (Exhibit 102).
ISR for PCT/US2000/25112 dated Jun. 8, 2001 (Exhibit 103).
ISR for PCT/US2003/023926 dated Jun. 23, 2004 (Exhibit 104).
ISR for PCT/US2005/018161 dated Jun. 4, 2008 (Exhibit 105).
ISR for PCT/US2005/044335 dated Sep. 22, 2006 (Exhibit 106).
ISR for PCT/US2007/008597 dated Jun. 4, 2008 (Exhibit 107).
ISR for PCT/US2008/050728 dated Oct. 10, 2008 (Exhibit 108).
ISR for PCT/US2008/054033 dated Aug. 21, 2008 (Exhibit 109).
ISR for PCT/US2008/055020 dated Aug. 14, 2008 (Exhibit 110).
ISR for PCT/US2008/055236 dated Nov. 14, 2008 (Exhibit 111).
ISR for PCT/US2008/056103 dated Sep. 3, 2008 (Exhibit 112).
ISR for PCT/US2008/061652 dated Dec. 1, 2008 (Exhibit 113).
ISR for PCT/US2008/062531 dated Nov. 18, 2008 (Exhibit 114).
ISR for PCT/US2008/080526 dated Mar. 25, 2009 (Exhibit 115).
ISR for PCT/US2009/0044720 dated Nov. 5, 2009 (Exhibit 116).
ISR for PCT/US2009/059190 dated Mar. 16, 2010 (Exhibit 117).
ISR for PCT/US2009/061698 dated Mar. 16, 2010 (Exhibit 118).
ISR for PCT/US2009/065928 dated Aug. 3, 2010 (Exhibit 119).
ISR for PCT/US2009/069531 dated Aug. 4, 2010 (Exhibit 120).
ISR for PCT/US2009/0695341 dated Mar. 4, 2010 (Exhibit 121).
ISR for PCT/US2010/043427 dated Mar. 12, 2010 (Exhibit 122).
ISR for PCT/US2011//021180 dated Jun. 15, 2011 (Exhibit 123).
ISR for PCT/US2011/021382 dated Mar. 15, 2011 (Exhibit 124).
ISR for PCT/US2011/028694 dared Jul. 27, 2011 (Exhibit 125).
Notice of Allowance dated Apr. 29, 1999 for U.S. Appl. No. 08/798,668 dated Apr. 29, 1999 (Exhibit 126).
Notice of Allowance dated Mar. 19, 2002 for U.S. Appl. No. 09/419,406 dated Mar. 19, 2002 (Exhibit 127 ).
Office Action for U.S. Appl. No. 08/587,911 dated Apr. 15, 1997 (Exhibit 128).
Office Action for U.S. Appl. No. 08/587,911 dated Jan. 5, 1998 (Exhibit 129).
Office Action for U.S. Appl. No. 08/587,911 dated Jul. 6, 1998 (Exhibit 130).
Office Action for U.S. Appl. No. 11/720,785 dated Dec. 23, 2010 (Exhibit 131).
Office Action for U.S. Appl. No. 11/720,785 dated Jul. 19, 2010 (Exhibit 132).
Office Action for U.S. Appl. No. 12/528,055 dated Jun. 27, 2011 (Exhibit 133).
Office Action for U.S. Appl. No. 12/530,390 dated Mar. 25, 2011 (Exhibit 134).
Office Action for U.S. Appl. No. 12/599,549 dated Apr. 26, 2011 (Exhibit 135).
Office Action in U.S. Appl. No. 08/196,003 dated Dec. 12, 1995 (Exhibit 136).
Office Action in U.S. Appl. No. 08/196,003 dated Oct. 2, 1996 (Exhibit 137).
Office Action in U.S. Appl. No. 08/245,297 dated Mar. 15, 1995 (Exhibit 138).
Office Action in U.S. Appl. No. 08/245,297 dated Jan. 22, 1996 (Exhibit 139).
Office Action in U.S. Appl. No. 08/245,297 dated Jul. 11, 1996 (Exhibit 140).
Office Action in U.S. Appl. No. 08/245,297 dated Dec. 9, 1996 (Exhibit 141).
Office Action in U.S. Appl. No. 08/798,668 dated Jan. 29, 1998 (Exhibit 142).
Office Action in U.S. Appl. No. 08/798,668 dated Jun. 6, 1997 (Exhibit 143).
Office Action in U.S. Appl. No. 08/798,668 dated Aug. 10, 1998 (Exhibit 144).
Office Action in U.S. Appl. No. 08/798,668 dated Apr. 29, 1999 (Exhibit 145).
Office Action in U.S. Appl. No. 08/933,824 dated Apr. 14, 1998 (Exhibit 146).
Office Action in U.S. Appl. No. 08/933,824 dated Jan. 5, 1999 (Exhibit 147).
Office Action in U.S. Appl. No. 09/395,345 dated May 3, 2000 (Exhibit 148).
Office Action in U.S. Appl. No. 09/395,345 dated Nov. 21, 2000 (Exhibit 149).
Office Action in U.S. Appl. No. 09/395,345 dated May 9, 2001 (Exhibit 150).
Office Action in U.S. Appl. No. 09/419,406 dated Jul. 17, 2001 (Exhibit 151).
Office Action in U.S. Appl. No. 09/419,406 dated Dec. 28, 2001 (Exhibit 152).
Office Action in U.S. Appl. No. 09/419,406 dated Apr. 24, 2000 (Exhibit 153).
Office Action in U.S. Appl. No. 09/419,408 dated Feb. 1, 2001 (Exhibit 154).
Office Action in U.S. Appl. No. 09/419,408 dated May 30, 2002 (Exhibit 155).
Office Action in U.S. Appl. No. 09/419,408 dated Nov. 14, 2002 (Exhibit 156).
Office Action in U.S. Appl. No. 10/075,425 dated Oct. 1, 2004 (Exhibit 157).

(56) References Cited

OTHER PUBLICATIONS

Office Action in U.S. Appl. No. 10/075,425 dated Jun. 17, 2005 (Exhibit 158).
Office Action in U.S. Appl. No. 10/356,736 dated Jul. 7, 2005 (Exhibit 159).
Office Action in U.S. Appl. No. 10/356,736 dated Apr. 10, 2006 (Exhibit 160).
Office Action in U.S. Appl. No. 10/356,736 dated Apr. 26, 2007 (Exhibit 161).
Office Action in U.S. Appl. No. 10/356,736 dated Nov. 30, 2007 (Exhibit 162).
Office Action in U.S. Appl. No. 10/356,736 dated Aug. 14, 2008 (Exhibit 163).
Office Action in U.S. Appl. No. 10/526,256 dated Dec. 29, 2008 (Exhibit 164).
Office Action in U.S. Appl. No. 10/526,256 dated May 9, 2008 (Exhibit 165).
Office Action in U.S. Appl. No. 10/526,256 dated Aug. 25, 2009 (Exhibit 166).
Written Opinion for PCT/US1995/01434 dated Nov. 20, 1995 (Exhibit 167).
Written Opinion for PCT/US1995/06107 dated Dec. 2, 1996 (Exhibit 168).
Written Opinion for PCT/US1997/00042 dated Oct. 29, 1997 (Exhibit 169).
Written Opinion for PCT/US2005/018161 dated Jun. 4, 2008 (Exhibit 170).
Written Opinion for PCT/US2005/044335 dated Aug. 26, 2006 (Exhibit 171).
Written Opinion for PCT/US2007/008597 dated Jun. 4, 2008 (Exhibit 172).
Written Opinion for PCT/US2008/050728 dated Oct. 10, 2008 (Exhibit 173).
Written Opinion for PCT/US2008/054033 dated Aug. 21, 2008 (Exhibit 174).
Written Opinion for PCT/US2008/055020 dated Aug. 14, 2008 (Exhibit 175).
Written Opinion for PCT/US2008/055236 dated Nov. 14, 2008 (Exhibit 176).
Written Opinion for PCT/US2008/056103 dated Sep. 3, 2008 (Exhibit 177).
Written Opinion for PCT/US2008/057820 dated Aug. 26, 2008 (Exhibit 178).
Written Opinion for PCT/US2008/061652 dated Dec. 1, 2008 (Exhibit 179).
Written Opinion for PCT/US2008/062531 dated Nov. 18, 2008 (Exhibit 180).
Written Opinion for PCT/US2008/063202 dated Nov. 18, 2008 (Exhibit 181).
Written Opinion for PCT/US2008/080526 dated Mar. 25, 2009 (Exhibit 182).
Written Opinion for PCT/US2009/044720 dated Nov. 5, 2009 (Exhibit 183).
Written Opinion for PCT/US2009/059190 dated Mar. 16, 2010 (Exhibit 184 ).
Written Opinion for PCT/US2009/061698 dated Mar. 16, 2010 (Exhibit 185).
Written Opinion for PCT/US2009/065928 dated Aug. 3, 2010 (Exhibit 186).
Written Opinion for PCT/US2009/069531 dated Aug. 4, 2008 (Exhibit 187).
Written Opinion for PCT/US2009/069541 datedMar. 4, 2010 (Exhibit 188).
Written Opinion for PCT/US2011/021382 dated Mar. 15, 2011 (Exhibit 189).
Written Opinion for PCT/US2011/028694 dated Jul. 27, 2011 (Exhibit 190).
Abraham et al., Haplotypic polymorphisms of the TNFB gene. *Immunogenetics* vol. 33 pp. 50-53 1991 (Exhibit 191).
Abreu et al., Mutations in NOD2 are associated with fibrostenosing disease in patients with Crohn's disease. *Gastroenterology* vol. 123 pp. 679-688 2002 (Exhibit 192).
Adam, Jamila et al., Immune response in cancer. *Pharmacology & Therapeutics* vol. 99 pp. 113-132 2003 (Exhibit 193).
Adams et al., 3400 new expressed sequence tags identify diversity of transcipts in the human brain. *Nature Genetics* vol. 4 pp. 256-267 1993 (Exhibit 194).
Agarwal, B. B. et al., The role of the TNF and its family members in inflammation and cancer: lessons from gene deletion. *Curr Drug Targets Inflamm Allergy* vol. 1 pp. 327-341 2002 (Exhibit 195).
Ahmad et al. The molecular classification of the clinical manifestations of Crohn's disease. *Gasterenterology* vol. 122 pp. 854-866 2002 (Exhibit 196).
Ajioka et al., Haplotype analysis of hemochromatosis: evaluation of linkage-disequilibrium approaches and evolution of disease chromosome. *Am J Hum Genet* vol. 60 pp. 1439-1447 1997 (Exhibit 197).
Akolkar et al., The IBD1 locus for susceptibility to Crohn's disease has a greater impack on Ashkenazi Jews with early onset diabetes. *Am J Gastroentrol* vol. 96 pp. 1127-1132 2001 (Exhibit 198).
Ames et al., Are vitamin and mineral deficiencies a major cancer risk? *Nature* vol. 694-704 2002 (Exhibit 199).
An et al., A tumor necrosis factor $\alpha$-inducible promoter variant of interferon-g accelerates CD4+ Tcell depletion in human immunodeficiency virus-1 infected individuals. *J Infectious Diseases* vol. 188 pp. 228-213 2003 (Exhibit 200).
Ando et al. Triplet repeat polymorphism within the NOTCH4 gene located near the junction of the HLA class II and class III regions in narcolepsy. *Tissue Antigens* vol. 50 pp. 646-649 1997 (Exhibit 201).
Andus et al., Measurement of TNFalpha mRNA in a small number of cells by quantitative polymerase chain reaction (PCR) *Regional Immunology* vol. 5 pp. 11-17 1993 (Exhibit 202).
Andus et al., Measurement of TNFalpha mRNA in lamina propia lymphocytes (LPL) isolated from mucosal biopsies by quantitative polymerase chain reaction (PCR). *Cytokines and cytokine receptor in mucosal immunity* Abstract # 2742 p. A1409 (Exhibit 203).
Annese et al., Genetic analysis in Italian families with inflammatory bowel disease supports linkage to the IBD1 locus—a GSIC study. *Eur J Hum Genet* vol. 7 pp. 567-573 1999 (Exhibit 204).
Aron et al., Analysis of shp70 gene polymorphism in allergic asthma *Allergy* vol. 54 pp. 165-170 1999 (Exhibit 205).
Ausubel, F. M. et al., Current protocols in Molecular Biology. Wiley Interscience, New York, 1987 1989 Book not included.
Badger et al., Idoxifene, a novel selective estrogen receptor modulator is effective in a rat model of adjuvant-induced arthritis. *J Pharmacology and Experimental Therapeutics* vol. 291 pp. 1380-1386 1999 (Exhibit 207).
Ballantyne, C. et al., Short communication, assignment of the gene for intercellular adhesion molecule-1 (ICAM-1) to proximal mouse chromosome 9. *Genomics*vol. 9 pp. 547-550 1991 (Exhibit 208).
Bao et al., Molecular mechanism for gender differences in susceptibility to T Cell mediated autoimmune diabetes in nonobese diabetic mice. *J of Immunol* vol. 168 pp. 5269-5379 2002 (Exhibit 209).
Becker et al., Clustering of non-major histocompatibility complex susceptibility candidate loci in human autoimmune disease. *Proc Natl Acad Sci*. vol. 95 pp. 9979-9984 1998 (Exhibit 210).
Benoit, R. et al., Presence of somatostatin-28-(1-12) in hypothalamus and pancreas. *Proc Natl Acad Sci. USA* vol. 79 pp. 917-921 1982 (Exhibit 211).
Beutler et al., Control of cachectin (tumor necrosis factor) synthesis: mechanisms of endotoxin resistance. *Science* vol. 232 pp. 977-980 1986 (Exhibit 212).
Biener-Ramanujan et al., Functional signaling of membrane-bound TL1A induces IFN-gamma expression. *FEBS Lett* vol. 11 pp. 2376-2380 2010 (Exhibit 213).
Bioque et al., Further evidence for a genetic association of interleukin-1 receptor antagonist and ulcerative colitis in the Northern and Mediterranean population. Abstract only *Gastroenterology* XP00673121 vol. 108 p. a783 1995 (Exhibit 214).

(56) References Cited

OTHER PUBLICATIONS

Boirivant et al., Hypoproliferative human lamina propia T cells retain the capacity to secrete lymphokines when stimulated via CD2/CD28 pathways. *Proceedings of the association of American physicians*Abstract Only *Proc Assoc Am Physicians* vol. 108 pp. 55-67 1996 (Exhibit 215).
Bourinbaiar et al., Pregnancy hormones, estrogen and progesteron prevent HIV-1 synthesis in monocytes but not lymphocytes. *FEBS Letters* vol. 302 pp. 206-208 1992 (Exhibit 216).
Brabin L., Interactions of the female hormonal environment, susceptibility to viral infection and disease progression. *AIDS Patient Care and STDs*. vol. 16, pp. 211-221 2002 (Exhibit 217).
Braegger et al., Tumor necrosis factor alpha in stool as a marker of intestinal inflammation. *The Lancet* vol. 339 pp. 89-91 1992 (Exhibit 218).
Brambs et al., Inflammatory Bowel Disease: Radiographical diagnostics. (reprints available at the Department of Radiography, Albert Ludwigs University Hospital, Freiburg, Federal Republic of Germany, pp. 3-62 undated (Exhibit 219).
Brant et al., American families with Crohn's disease have strong evidence for linkage to chromosomes 16 but not chromosome 12. *Gastroentrol* vol. 115 pp. 1056-1061 1998 (Exhibit 220).
Braun et al., Chapter 13: Multiparameter analysis of immunogenetic mechanisms in clinical diagnosis and mamagement of inflammatory bowel disease. *Immune mechanisms in inflammatory bowel disease* edited by Richard S. Blumberg and Markus F. Neurath Mar. 10, 2006, Springer first edition pp. 209-218 (Exhibit 221).
Bream et al., A single nucleotide polymorphism in the proximal IFN-gamma promoter alters control of gene transcription. *Genes and Immunity* vol. 3 pp. 165-169 2002 (Exhibit 222).
Buning et al., Heterozygosity for IL23R, p.Arg318GIn confers a protective effect not only against Crohn's disease but also ulcerative colitis. *Aliment. Pharmacol Ther*. vol. 26 pp. 1025-1033 2007 (Exhibit 223).
Burks, C et al., GenBank *Nucleic Acids Res* (*Suppl*) vol. 29 pp. 2065-2069 1992 (Exhibit 224).
Bush et al., Cancer chemoresistance: the relationship between p53 and multidrug transporters *Int J Cancer* vol. 98 pp. 323-330 2002 (Exhibit 225).
Calemine, J. B. et al. Immunomodulation by diethylstillbestrol is dose and gender related: effects on thymocyte apoptosis and mitogen-induced proliferation. *Toxicology* vol. 178 pp. 101-118 2002 (Exhibit 226).
Cardullo et al., Detection of nucleic acid hybridization by nonradiative fluorescence resonance energy transfer. *Proc Natl Acad Sci. USA*vol. 85 pp. 8790-8794 1992 (Exhibit 227).
Casini-Raggi et al., Mucosal imbalance of IL-1 and IL-1 receptor antagonist in inflammatory bowel disease. *J Immunol* vol. 154 pp. 2434-2440 1995 (Exhibit 228).
Cavanaugh et al., Analysis of Australian Crohn's disease pedigrees refines the localization for susceptibility to inflammatory bowel disease on chromosome 16. *Ann Hum Genet* vol. 62 pp. 291-298 1998 (Exhibit 229).
Cenci et al., Estrogen deficiency induces bone loss by increasing T cell proliferation and lifespan through IFN-gamma induced class II transactivator. *Proc Natl Acad Sci*. vol. 100 pp. 10405-10410 2003 (Exhibit 230).
Chaudhary et al., Prediction of response to infliximab in Crohn's disease. *Digestive and Liver Disease* vol. 37 pp. 559-563 2005 (Exhibit 231).
Chevillard et al. Two new polymorphisms in the human interferon gamma promoter. *Eur J Immunogenetics* vol. 29 pp. 52-56 2002 (Exhibit 232).
Chiaretti, S et al., Gene expression profile of adult T-cell acute lymphocytic leukemia identifies distinct subsets of patients with different responses to therapy and survival. *Blood* vol. 103 pp. 2771-2778 2004 (Exhibit 233).
Cho et al., Confirmation of a susceptibility locus for Crohn's disease on chromosome 16. *Inflamm Bowel Dis*. vol. 3 pp. 186-190 1997 (Exhibit 234).
Cho et al., Identification of novel susceptibility loci for inflammatory bowel disease on chromosome 1p, 3q and 4q: evidence for epistasis between 1p and 1BD1. *Proc Natl Acad Sci*vol. 95 pp. 7501-7501 1998 (Exhibit 235).
Cippitelli et al. Retinoic acid-induced transcriptional modulation of the human interferon-gamma promoter. *J Biol Chemistry* vol. 271 pp. 26783-26793 1996 (Exhibit 236).
Cippitelli et al., Vitamin D3: a trasncriptional modulator of the interferon-gamma gene. *Eur J Immunol* Abstract Only vol. 28 pp. 3017-3030 1998 (Exhibit 237).
Costello et al., Dissection of the inflammatory bowel disease transcriptome using genome wide cDNA microarrays. *PloS Medicine* vol. 2 pp. 0771-0787 2005 (Exhibit 238).
Curran et al., Genetic analysis of inflammatory bowel disease in a large European cohort supports linkage to chromosome 12 and 16. *Gastroenterology* vol. 115 pp. 1066-1071 1998 (Exhibit 239).
Cushman et al., Effects of estrogen and selective estrogen receptor modulators in hemostasis and inflammation: potential differences among drugs. *Annals of New York Academy of Sciences* Abstract Only vol. 949 pp. 175-180 2001 (Exhibit 240).
Cushman et al., Tamoxifen and cardiac risk factors in healthy women—suggestion of an anti-inflammatory effect, arteriosclerosis, thrombosis and vascular biology. *Arterioscler Thromb Vasc Biol* vol. 21 pp. 251-266 2001 (Exhibit 241).
Cuzzocrea et al., 19beta-estradiol anti-inflammatory activitiy in Carrageenan-induced pleurisy. *Endocrinology* vol. 141 pp. 1455-1465 2000 (Exhibit 242).
Derrkx et al., Tumor-necrosis-factor antibody treatment in Crohn's disease. *The Lancet* vol. 342 pp. 173-174 1993 (Exhibit 243).
DeSilva et al., Pharmacogenetics of infliximab in Crohn's disease: the 5q31/IBD5 risk haplotype predict response. *Gastroenterology* 2002 vol. 122 Abstract M1423 (Exhibit 244).
Devlin et al., NOD2 variants and antibody response to microbial antigens in Crohn's disease patients and their unaffected relatives. *Gastroenterology* vol. 132 pp. 576-586 2007 (Exhibit 245).
Devlin et al., NOD2 variants are significantly associated with sero-reactivity to microbial antigens in Crohn's disease. Abstract Only 2006 Journal unknown (Exhibit 246).
Devlin et al., The p631H variant of the TLR2 gene associated with sero-reactivity to microbial antigens in Jewish patients with Crohn's disease. Abstract Only 2007 Journal unknown (Exhibit 247).
Diamond, M. S. et al., Binding of the integrin Mac-1 (CD11b/CD18) to the third immunoglobulin-like domain of ICAM01 (CD54) and its regulation by glycosylation. *Cell* vol. 65 pp. 961-971 1991 (Exhibit 248).
Diamond, M. S. et al., ICAM-1 (CD54): A counter receptor for Mac-1 (CD11b/CD18). *J Cell Biol* vol. 111 pp. 3129-3139 1990 (Exhibit 249).
Dib et al., A comprehensive genetic map of the human based on 5,264 microsatellites. *Nature* vol. 380 pp. 152-154 1996 (Exhibit 250).
Dubinsky et al., CARD8: A novel association with childhood onset ulcerative colitis (UC). *AGA Institute* Abstract # T1983 p. A-587 2006 (Exhibit 251).
Dubinsky et al., Familial expression of serological immune responses in pediatric IBD. *J of Pediatric Gastroenterology and Nutrition* Abstract #150 vol. 41 p. 539 2005 (Exhibit 252).
Dubinsky et al., IL-23 receptor (IL-23R) gene protects against pediatric Crohn's disease. *Inflamm Bowel Disease* vol. 13 pp. 511-515 2007 (Exhibit 253).
Dubinsky et al., Increased immune reactivity predicts aggressive complicating Crohn's disease in children. Abstract only 2007 Journal unknown (Exhibit 254).
Dubinsky et al., Serum immune responses predict rapid disease progression among children with Chron's disease: immune responses predict disease progression. *Am J. Gastroenterology* vol. 101 pp. 360-367 2006 (Exhibit 255).
Duerr R. H. et al., A genome-wide association study identifies IL23R as an inflammatory bowel disease gene. *Science Express* vol. 314 pp. 1-5 2006 (Exhibit 256).

(56) References Cited

OTHER PUBLICATIONS

Duerr R. H. et al., Association between ulcerative colitis and a polymorphism in intron 2 of the interleukin-2 receptor antagonist gene. *Gastroenterology* Abstract Only vol. 108 p. a812 1995 (Exhibit 257).
Duerr R. H. et al., Homozygosity for an HLA class II group haplotype is associated with pANCA positive and familial ulcerative colitis. Abstract only *Gastroenterology* vol. 108 p. a812 1995 (Exhibit 258).
Duerr R. H. et al., Linkage and association between inflammatory bowel disease and a locus on chromosom 12. *Am J Hum Genet* vol. 63 pp. 95-100 1998 (Exhibit 259).
Email from James Jenkins referencing the "Amazon.com" website regarding exact publication date of "Immune Mechanism in Inflammatroy Bowel Disease", edited by Richard S. Blumberg and Markus F. Neurath; Springer first edition. 2 pages. (Exhibit 260).
Erlandsson et al., Effects of raloxifene, a selective estrogen receptor modulator on thymus T cell reactivity and inflammation in mice. *Cellular Immunology* vol. 205 pp. 103-109 2000 (Exhibit 261).
Erlich et al., Chapter 32 HLA DNA typing. PCR protocols. Edited by Innis et al. pp. 261-271 (Exhibit 262).
Ewens and Spielman, The transmission/disequilibrium test: history, subdivision, and admixture. *Am J Hum Geneticsvol.* 57 pp. 455-464 1995 (Exhibit 263).
Fawcett, J. et al., Molecular cloning of ICAM-3, a third ligand for LFA-1, constitutively expressed on resting leukocytes. *Nature* vol. 360 1992 (Exhibit 264).
Feder et al., A novel MHC class I-like gene is mutated in patients with hereditary heaemochromatosis. *Nature Genetics* vol. 13 pp. 399-408 1996 (Exhibit 265).
Ferrante et al., Predictors of early response to infliximab in patients with ulcerative colitis. *Inflamm Bowel Disease* 2007 vol. 13 pp. 123-128 (Exhibit 266).
Ferraris et al., Analysis of CARD15 gene variants in Italian pediatric patients with inflammatory bowel disease. *J of Pediatrics* pp. 272-273 2005 (Exhibit 267).
Fleshner et al., Both preoperative pANCA and CBir1 flagellin expression in ulcerative colitis (UC) patients influence pouchitis developemt after illeal pouch-anal anastomosis (IPAA). Abstract only 2006 Journal unknown (Exhibit 268).
Flores Mona G. et al. In vitro evaluation of the effects of candidate immunosuppressive drugs: flow cytometry and quantitative real-time PCR as two independent and correlated read-outs. *Journal of Immunological Methods* vol. 289 pp. 123-135 2004 (Exhibit 269).
Fox et al., Estrogen regulates the IFN-gamma promoter. *J Immunol* vol. 146 pp. 4362-4367 1991 (Exhibit 270).
Fujikado et al., Identification of arthritis related gene clusters by microarray analysis analysis of two independent mouse models for rheumatoid arthritis. *Arthritis Research and Therapy* vol. 8 pp. 1-13 2006 (Exhibit 271).
Fujino et al., Increased expression of interleukin 17 in inflammatory bowel disease gene. *Gut* vol. 52 pp. 65-70 2003 (Exhibit 272).
Garcia-Bates et al., Peroxisome proliferator-activated receptor gamma ligands enhance human B cell antibody production and differentiation. *J Immunology* vol. 183 pp. 6903-6912 2009 (Exhibit 273).
Gasche et al., A simple classification of Crohn's disease: report of the working party for the world congresses of gastroenterology, Vienna. *Inflammatory Bowel Disease* vol. 6 pp. 8-15 2000 (Exhibit 274).
GenBank Accession No. AF129756.1 (Exhibit 275).
GenBank Accession No. AF134726 (Exhibit 276).
GenBank Accession No. AF385089 (Exhibit 277).
GenBank Accession No. AF513860 (Exhibit 278).
GenBank Accession No. AC007728 (Exhibit 279).
GenBank Accession No. AX259776 (Exhibit 280).
GenBank Accession No. NM022162 (Exhibit 281).
GenBank Accession No. U89335 (Exhibit 282).
GenBank Accession No. U89336 (Exhibit 283).
GeneBank Accession No. AF450133 (Exhibit 284).
GeneCard NOD2 gene (Exhibit 285).
Gewirtz et al., Dominant-negative TLR5 polymorphism reduces adaptive immune response to flagellin and negatively associates with Crohn's disease. *Am J Physiol Gastrointest Liver Physiol* 290: pp. G1157-G1163, 2006 (Exhibit 286).
Ghosh et al., Anti-TNF therapy in Crohn's disease *Novartis Foundation Symposium* vol. 263 pp. 193-218 2004 (Exhibit 287).
Giacomelli et al., Combination therapy with cyclosporin and methotrexate in patients with early rheumatoid arthritis soon inhibits TNF production without decreasing TNF mRNA level: an in vivo and in vitro study. *Clinical and Experimental Rheumatology* vol. 20 pp. 365-372 2002 (Exhibit 288).
Gilmore et al., Effect of estradiol on cytokine secretion by proteolipid proten-specific T cell clones isolated from multiple sclerosis patients and normal control subjects. *J Immmunology* Abstract only vol. 158 pp. 446-451 1997 (Exhibit 289).
Gonsky et al., CD2 mediates activation of the IFN-gamma intronic STAT binding region in mucosal T cells. *Eur J Immunol* vol. 33 pp. 1152-1162 2003 (Exhibit 290).
Gonsky et al., Mucosa-specific targets for regulation of IFN-gamma expression: lamia propia T cells use different cis-elements than peripheral blood T cells to regulate transactivation of IFN-gamma expression. *J Immunol* vol. 164 pp. 1399-1407 2000 (Exhibit 291).
Greenstein et al., Perforating and non-perforating indications for repeated operation in Crohn's disease: evidence of two clinical forms. *Gut* vol. 29 pp. 588-592 1988 (Exhibit 292).
Haertel C. et al., Dose-dependent immunomodulatory effects of acetylsalicylic acid and indomethacin in human whole blood: potential role of cyclooxygenase-2 inhibition. *Scandanavian Journal Immunology* vol. 60 pp. 412-420 2004 (Exhibit 293).
Hampe et al., A genomewide analysis provides evidence for novel linkage in inflammatory bowel disease in a large European cohort. *Am J Hum Genet* vol. 64 pp. 808-816 1999 (Exhibit 294).
Hampe et al., A genome-wide association scan of nonsynonymous SNPs identifies a susceptibility variant for Crohn disease in ATG16L1 *Nature Genetics* vol. 39 pp. 207-211 2007 (Exhibit 295).
Hampe et al., Association between insertion mutation in NOD2 gene and Crohn's disease in German and British populations. *Lancet* vol. 357 pp. 1925-1928 2001 (Exhibit 296).
Hampe et al., Association of NOD2 (CARD15) genotype with clinical course of Crohn's disease: a cohort study. *Lancet* Lancet Limited pp. 1661-1665 vol. 35 2002 (Exhibit 297).
Hanifi et al., Genetic structure of IDDM1: two separate regions in the major histocompatibility complex contribute to suceptibility or protection. *Diabetes A Journal of the American Diabetes Association* vol. 47 pp. 1-7 1999 (Exhibit 298).
Harnish et al. Beneficial effects of estrogen treatment in the HLA-B27 trangenic rat model of inflammatory bowel disease. *Am J Physiol Gastrointest Liver Physiology* vol. 286 pp. G118-G124 2004 (Exhibit 299).
Hartel, Christopher et al., Delayed cytokine mRNA expresion kinetics after T-lymphocyte costimulation: A quantitative measure of the efficacy of cyclosporin A-based immunosuppression. *Clinical Chemistry* vol. 48 pp. 2225-2231 2002 (Exhibit 300).
Hazra et al., Common variant of FUT2 are associated with plasma vitamin B12 levels. *Nature Genetics* vol. 40 pp. 1160-1162 2008 (Exhibit 301).
Herbon et al. High-resolution SNP scan of chromosome 6p21 in pooled samples from patients with complex diseases. *Genomics* vol. 81 pp. 510-518 2003 (Exhibit 302).
Heresbach et al., NOD2/CARD15 gene polymorphisms in Crohn's disease: a genotype-phenotype analysis. *Eur J Gastroenterology and Hepatology* vol. 16 pp. 55-62 2004 (Exhibit 303).
Hess et al., The hydroxylamine of sulfamethoxazole synergizeswith FK506 and cyclosporin A inhibiting T-cell proliferation *Journal of Pharmacology and Experimental Techniques* vol. 281 pp. 540-548 1996 (Exhibit 304).
Hirschhorn et al., A comprehensive review of genetic association studies. *Genetics in Medicine* vol. 4 pp. 45-61 2002 (Exhibit 305).
Hlavaty et al., Polymorphisms in apoptosis genes predict response to infliximab therapy in luminal and fistulizing Crohn's disease. *Aliment Pharmacol Ther* vol. 22 pp. 613-626 2005 (Exhibit 306).

(56) References Cited

OTHER PUBLICATIONS

Hogg, N. and Landis, R. Adhesion molecules in cell interactions. *Curr Opin Immunol*. vol. 5, pp. 383-390 1993 (Exhibit 307).
Scientists Discover New Gene Associated with Crohn's Disease (Exhibit 308).
Hugot et al., Association of Nod2 leucine-rich repeat variants with sesceptibility to Crohn's disease. *Nature* vol. 411 pp. 599-603 2001 (Exhibit 310).
Hugot et al., Linkage analyses of chromosome 6 loci, including HLA, in familian aggregations of Crohn's disease GETAID. *Am J Med Genet* vol. 52 pp. 207-213 1994 (Exhibit 311).
Hugot et al., Mapping of a susceptibility locus for Crohn's disease on chromosome 16. *Nature* vol. 379 pp. 821-823 1996. (Exhibit 312).
Inohara et al., Human NOD1 confers responsiveness to bacterial lipopolysaccharides. *J Biol Chem* vol. 276 pp. 2551-2554 2001 (Exhibit 313).
Ioannidis et al., Replication validity of genetic association studies. *Nature Genetics* vol. 29 pp. 306-309 2001 (Exhibit 314).
Ippoliti et al., Combination of innate and adaptive immune alterations increased the liklihood of fibrostenosis in Crohn's disease. *Inflamm Bowel Disease* vol. 16 pp. 1279-1285 2010 (Exhibit 315).
Ippoliti et al., The relationship between abnormal innate and adaptive immune function and fibrostenosis in Crohn's disease patients. Abstract only. 2006 Journal unknown (Exhibit 316).
Iris et al., Dense Alu clustering and a potential new member of the NFkB family within a 90 kilobase HLA Class III segment *Nature Genetics* vol. 3 pp. 137-145 1993 (Exhibit 317).
Jacob et al., Definition of microsatellite size variants for Tnfa and Hsp70 in autoimmune and nonautoimmune mouse strains *Immunogenetics* vol. 36 pp. 182-188 1992 (Exhibit 318).
Jarjour et al., The 8.5 kb PatI allele of the stress protein gene Map70-2—an independent risk factor for systemic lupus erythematosus in African Americans. *Hum Immunol* vol. 45 pp. 59-63 1996 (Exhibit 319).
Johnston, M. I. et al. Present status and future prospects for HIV therapies. *Science* vol. 260 pp. 1286-1293 1993 (Exhibit 320).
Jongeneel et al., Extensive genetic polymorphism in the human tumor necrosis factor region and relation to extended HLA haplotypes. *Proc Natl Acad Sci* vol. 88 pp. 9717-9721 1991 (Exhibit 321).
Juhasz et al., Quantification of chemotherapeutic target gene mRNA expression in human breast cancer biopsies: comparison of real-time reverse transcription-PCR vs. relative quantification reverse transcription-PCR utilizing DNA sequence analysis of PCR product. *Journal of Clinical Laboratory Analysis* vol. 17 pp. 184-194 2003 (Exhibit 322).
Karpuzoglu-Sahin et al., Effects of long-term estrogen treatment on IFN-gamma, IL-2 and IL-4 gene expression and protein synthesis in spleen and thymus of normal C57BL/6 mice. *Cytokine* vol. 14 pp. 208-217 2001(Exhibit 323).
Karpuzoglu-Sahin et al., Interferon-gamma levels are upregulated by 17-beta-estradiol and diethylstibestrol. *J Reproductive Immunology*vol. 52 pp. 113-127 2001 (Exhibit 324).
Kim et al. DQCAR113and DQCAR115 in combination with HLA-DRB1 alleles are significant markers of susceptibility to rheumatoid artiritis in the Korean population. *Tissue Antigens* vol. 54 pp. 552-559 1999 (Exhibit 325).
Kirchhausen et al., Location of the domains of ICAM-1 by immunolabeling and single-molecule electron microscopy. *J Leukocyte Biology* vol. 53 pp. 342-346 1993 (Exhibit 326).
Kita, Y. et al., Sequence and expression of rat ICAM-1. *Biochim Biophys Acta*vol. 1131 pp. 108-111 1992 (Exhibit 327).
Klein N J et al., Ex-vivo assessment of candidate anti-inflammatory agents in the treatment of Gram-negative sepsis. *Immunology and Infectious Disease* vol. 4 pp. 33-35 1994 (Exhibit 328).
Koutroubakis et al., Tumor necrosis factor-alpha polymorphism in inflammatory bowel disease *Hellenic J of Gastroenterology* vol. 8 pp. 132-135 1995 (Exhibit 329).
Kugathansan et al., L1007FsinsC variant of CARD15/NOD2 is strongly associated with early onset and fibrostenosing behavior in pediatric Crohn's disease. *Gasteroenterology* vol. 126 No. 4 Supp 2 pp. A68 524 (Exhibit 330).
Kugathansan et al., Loci on 20q13 and 21q22 are associated with pediatric onset inflammatory bowel disease. *Nature Genetics* 2008 vol. 40 pp. 1211-1215 (Exhibit 331).
Kuntz, H. D. et al., Inflammatory Bowel Disease: endoscopic diagnostics. (Reprints available at the Department of Gastroenterology and Hepatology "Bergmannshell" Hospital, University of Bochum, Federal Republic of Germany) pp. 3-38 (Undated) (Exhibit 332).
Kutyavin et al., 3-minor groove binder-DNA probes increase sequence specificity at PCR extension temperatures. *Nucleic Acid Res* vol. 28 pp. 655-661 2000 (Exhibit 333).
Kutyavin et al., Oligonucleotides with conjugated dihyropyrroloindole tripeptides: base composition and backbone effects on hybridization. *Nucleic Acid Res* vol. 25 pp. 3718-3723 1997 (Exhibit 334).
Lakatos et al., NOD2/CARD15 mutations and genotype-phenotype correlations in patients with Crohn's disease. Hungarian multicenter study *Orv. Hetil*. vol. 145 pp. 1403-1411 2004 (Exhibit 335).
Landegren, U. et al., A ligase-mediated gene detection technique. *Science*vol. 241 pp. 1077-1080 1988 (Exhibit 336).
Lasky, L., Selectins: interpreters of cell-specific carbohydrate information during inflammation. *Science* vol. 258 pp. 964-969 1992 (Exhibit 337).
Latham et al., Estradiol treatment redirects the isotype of the autoantibody response and prevents the development of autoimmune arthritis. *J of Immunol* vol. 171 pp. 5820-5826 2003 (Exhibit 338).
Laurence et al. Effect of tamoxifen on regulation of viral replication and human immunodeficiency virus (HIV) long terminal repeat-directed transcription in cells chronically infected with HIV-1. *Blood* vol. 75 pp. 696-703 1990 (Exhibit 339).
Lee et al., Estrogen-mediated protection against HIV Tat protein-induced inflammatory pathways in human vascular endothelial cells. *Cardiovascular Research* vol. 63 pp. 139-148 2004 (Exhibit 340).
Lemna, W. K. et al., Mutation analysis for heterozygote detection and the prenatal diagnosis of cystic firbosis. *N. Eng. J. Med*. vol. 322 pp. 291-296 1990 (Exhibit 341).
Leong et al., NOD2/CARD15 gene polymorphisms and Crohn's disease in the Chinese population. *Aliment Pharmacol Thera* vol. 17 pp. 1465-1470 2003 (Exhibit 342).
Lesage et al., CARD15/NOD2 mutational analysis and genotype-phenotype correlation in 612 patients with inflammatory bowel disease. *Am J of Human Genetics* vol. 70 pp. 845-857 2002 (Exhibit 343).
Leung, S. Y. et al. Expression profiling identifies chemokine (C-C Motif) ligand 18 as an independent prognostic indicator of gastric cancer. *Gastroenterology* vol. 127 pp. 457-469 2004 (Exhibit 344).
Li et al., Cloning, characterization and the complete 56.8-kilobase DNA sequence of the human NOTCH4 gene. *Genomics* vol. 51 pp. 45-58 1998 (Exhibit 345).
Li et al., New serological biomarkers of inflammatory bowel disease. *World J of Gastroenterology* vol. 14 pp. 5115-5125 2008 (Exhibit 346).
Limbergen et al., IL23R Arg381 Gln is associated with childhood onset inflammatory bowel disease in Scotland. *Gut* vol. 56 pp. 1173-1174 2007 (Exhibit 347).
Linder et al. Tamoxifen enhances interferon regulated gene expression in breat cancel cells. *Molecular and Cellular Biochemistry* Abstract Only vol. 167 pp. 169-177 1997 (Exhibit 348).
Lipsky, P. Structure, function and regulation of molecules involved in leukocyte adhesion. New York: Springer-Verlag 1993 Book not included.
Liu et al., Mucosal gene expression profiles following the colonization of immunocompetent defined-flora C3H mice wih Helicobacter bilis: a prelude to typhlocolitis. *Microbes and Infection* vol. 11 pp. 374-383 2009 (Exhibit 350).

(56) References Cited

OTHER PUBLICATIONS

Livak, Allelic discrimination using fluorogenic probes and the 5' nuclease assay. *Genetic Analysis* vol. 14 pp. 143-149 1999 (Exhibit 351).
Lodes et al., Bacterial flagellin is a dominant antigen in Crohn disease. *Journal of Clinical Investigation*, vol. 113, pp. 1296-1306 May 2004 (Exhibit 352).
Lorenz-Meyer, H. Inflammatory Bowel Disease Laboratory Diagnostics. (Reprints available from the City Hospital, Friedrichshafen, Federal Republic of Germany) pp. 3-29 (undated) (Exhibit 353).
Louis et al., Association between polymorphism in IgG Fc receptor IIIa coding gene and biological response to infliximab in Crohn's disease. *Aliment Pharmacol Ther* 2004 vol. 19 pp. 511-519 (Exhibit 354).
Macdonald et al., Tumor necrosis factor-alpha and interferon-gamma production measured at the single cell level in normal and inflamed human intestine *Clin Exp Immunol* vol. 81 pp. 301-302 1990 (Exhibit 355).
Maniatis, T. et al. Molecular Cloning: A laboratory manual. Cold Spring Harbor Laboratory press. 1982 Book not included.
Mansfield et al., Novel genetic association between ulcerative colitis and the antiinflammatory cytokine interleukin-1 receptor antagonist. *Gastroenterology* pp. 637-642 vol. 106 1994 (Exhibit 357).
Martin et al., Recombination rates across the HLA complex: use of microsatellites as a rapid screen for recombinant chromosome. *Human Molecular Genetics* vol. 4 pp. 423-428 1995 (Exhibit 358).
Martins et al., Transcriptional repressor Blimp-1 regulates T cell homeostasis and function. *Nature Immunology* vol. 7, pp. 457-265 2006 (Exhibit 359).
Mascheretti et al. Pharmacogenetic investigation of the TNF/TNF-receptor system in patients with chronic active Crohn's disease treated with infliximib *The Pharmacogenomics Journal* vol. 2 pp. 127-136 2002 (Exhibit 360).
Matalka, K. Z. The effect of estradiol but not progesterone on the production of cytokines in stimulated whole blood is concentration-dependent. *Neuro Endocrinology Letters* Abstract only. vol. 24 pp. 185-191 2003 (Exhibit 361).
Matejuk et al., 17-beta-estradiol inhibits cytokine, chemokine and chemokine receptor mRNA expression in the central nervous system of gemale mice with experimental autoimmune encephalomyelitis. *J of Neuroscience Research* vol. 65 pp. 529-542 2001 (Exhibit 362).
Matsunaga, Hiroko et al., Application of differential displayto identify genes fir lung cancer detection in peripheral blood. *Int J of Cancer* vol. 100 pp. 593-599 2002 (Exhibit 363).
McCall et al., Constitutive expression of TNF-a and of an IL-8 gene is associated with genetic susceptibility to chronic granulomatous enterocolitis in inbred rats *AGA Abstracts* p. A740 1993 (Exhibit 364).
McEver, R. Leukocyte—endothelial cell interactions. *Curr Opin Cell Biol* vol. 4 pp. 840-849 1992 (Exhibit 365).
Mehmut et al., Fas ligand and TNF-related apoptosis-inducing ligand induction of infiltrating lymphocytes in bladder carcinoma by Bacillus Calmette-Guerin treatment *Urologica International* vol. 75 pp. 87-88 2005 (Exhibit 366).
Mei et al., Familian expression of anti-*Escherichia coli* outer membrane porin C in relatives of patients with Crohn's disease. *Gasteroenterology* vol. 130 pp. 1078-1085 2006 (Exhibit 367).
Mei L., Association between IL17A and IL17RA genes and inflammatory bowel disease (IBD). Abstract only 2007 Journal unknown (Exhibit 368).
Melmed et al., A prospective analysis of predictive factors for the diagnosis of Crohn's disease after Ileal pouch-anal anastomosis for ulcerative colitis. Abstract only 2007 Journal unknown (Exhibit 369).
Melmed et al., Patients with inflammatry bowel disease are at risk for vaccine-preventable illness. *Am J Gasteroenterol* vol. 101 pp. 1834-1849 2006 (Exhibit 370).
Mesange et al., Ligands of the antiestrogen-binding site are able to inhibit virion production of human immunodeficiency virus 1-infected lymphocytes. *Molecular Pharmacology* vol. 50 pp. 75-79 1996 Abstract only (Exhibit 371).
Messer et al., Polymorphic structure of the tumor necrosis factor (TNF) locus: an NcoI polymorphism in the first intron of TNF-B gene correlates with a variant in amino acid position 26 and a reduced level of TNF-B production *J Exp Med* vol. 173 pp. 209-219 1991 (Exhibit 372).
Milner and Campbell. Polymorphic analysis of the three MHC-linked HSP70 genes. *Immunogenetics* vol. 36 pp. 357-362 1992 (Exhibit 373).
Mingjia et al., How oestrogen or progesterone might change a woman's susceptibility to HIV-1 infections. *The Australian and New Zealand Journal of Obstetrics and Gynecology* Abstract only. vol. 42 pp. 472-475 2002 (Exhibit 374).
Misiewicz et al., The estrogen antagonist tamoxifen inhibits carrageenan induced inflammation in LEW/N female rats. *Life Sciences* vol. 58 pp. PL281-PL286 1996 (Exhibit 375).
Moghaddam et al., Genetic structure of IDDM1: two separate regions in the major histocompatibility complex contribute to susceptibility or protection. *Diabetes* vol. 47 pp. 263-269 1998 (Exhibit 376).
Mow et al., Association of antibody responses to microbial antigens and complications of small bowel Crohn's disease. *Gastroenterology* vol. 126 pp. 414-424 2004 (Exhibit 377).
Murch et al., Location of tumor necrosis factor alpha by immunochemistry in chronic inflammatory bowel disease *Gut* vol. 34 pp. 1705-1709 1993 (Exhibit 378).
Murillo et al., CARD15 gene and the classification of Crohn's disease. *Immunogenetics* vol. 54 pp. 59-61 2002 (Exhibit 379).
Murray et al., GenBank Accession No. G08322, Feb. 5, 1997 (Exhibit 380).
Nadal et al., Imbalance in the composition of the duodenal microbiata of children with coeliac disease. *J Medical Microbiol* vol. 56 pp. 1669-1674 2007 (Exhibit 381).
Nakamura et al., In situ expression of the cell adhesion molecules in Inflammatory Bowel Disease; evidence of immunologic activation of vascular endothelial cells. *Lab. Investig.*vol. 69 No. 1, pp. 77-85, 1993 (Exhibit 382).
Nakaya et al., Estrogenic compounds suppressed interferon-gamma production in mouse splenocytes through direct cell-cell interaction. *In vitro cellular and developmental biology animal*. vol. 39 pp. 383-387 2003 (Exhibit 383).
NCBI Accession No. NM_001198.3 (Exhibit 384).
NCBI SNP ID rs11209063 (Exhibit 385).
NCBI SNP ID rs12495640 (Exhibit 386).
NCBI SNP ID rs12638201 (Exhibit 387).
NCBI SNP ID rs1495964 (Exhibit 388).
NCBI SNP ID rs1908632 (Exhibit 389).
NCBI SNP ID rs2066844 (Exhibit 390).
NCBI SNP ID rs2066845 (Exhibit 391).
NCBI SNP ID rs2066847 (Exhibit 392).
NCBI SNP ID rs2302600 (Exhibit 393).
NCBI SNP ID rs6788981 (Exhibit 394).
NCBI SNP ID rs7374667 (Exhibit 395).
NCBI SNP ID rs746503 (Exhibit 396).
NCBI SNP ID rs7613548 (Exhibit 397).
Nedospasov et al., Genetic polymorphism of the human gene locus containing genes for tumor necrosis factors: ethnic differences in allele frequency distribution, Chemical Abstracts, vol. 120, No. 5, 1994, Columbus, Ohio, US, abstract No. 47183y. (Exhibit 398).
Nedospasov, S.A., et al., Dna sequence polymorphism at the human tumor necrosis factor (TNF) locus. Numerous TNF/lymphotoxin alleles tagged by two closely linked microsatellites in the upstream region of the lymphotoxin (TNF-beta) gene. *J. Immunol.* vol. 147 pp. 1053-1059 1991 (Exhibit 399).
Ogura et al., NOD2, a Nod1/Apaf-1 family member that is restricted to monocytes and activates NF-kB. *J Biol Chem* vol. 276 pp. 4812-4818 2001 (Exhibit 400).
Ogura, Y. et al., A frameshift mutation in NOD2 associates with susceotibility to Crohn's disease. *Nature* vol. 411: pp. 603-606, 2001 (Exhibit 401).

(56) References Cited

OTHER PUBLICATIONS

Ohmen et al., Susceptibility locus for inflammatory bowl disease on chromosome 16 has a tole in Crohn's disease, but not in ulcerative colitis. *Hum Mol Genet* vol. 5 pp. 1679-1683 1996 (Exhibit 402).
Okazaki et al., Contributions of the IBD5, IL23R, ATG16L1, and NOD2 to Crohn's disease risk in a population-based case-controlled study: evidence of gene-gene interaction *Inflamm Bowel Disease* vol. 14 pp. 1528-1541 2008 (Exhibit 403).
Orholm et al., Familial occurrence of inflammatory bowel disease. *New England Journal of Medicine* vol. 84 pp. 84-88 1991 (Exhibit 404).
Over et al., Thromphilia and inflammatroy bowel disease: does factor V mutation have a role? *European Journal of Gastroenterology and Hepatology* vol. 10 pp. 827-829 1998 (Exhibit 405).
Owerbach and Gabbay. The HOXD8 locus (2q31) is linked to type I diabetes—interaction with chromosome 6 and 11 disease susceptibility genes. *Diabetes* vol. 44 p. 132-136 1995 (Exhibit 406).
Papadakis et al., An interaction between IL-23R and IL-17A and between IL-23R and IL-17RA haplotypes is necessary for susceptibility to Crohn's disease. Abstract only 2007 Journal unknown (Exhibit 407).
Papadakis et al., Anti-Flagellin (Cbir1) phenotypic and genetic Crohn's Disease associations, *Inflamm Bowel Dis*, vol. 13, No. 5, May 2007 (Exhibit 408).
Papadakis et al., Phenotypic and functional characterization of CCR9+ T lymphocytes in small intestinal Crohn's disease. Abstract only. 2006 Journal unknown (Exhibit 409).
Papp et al., Seroreactivity to microbial components in Crohn's disease is associated with Ileal involvement, noninflammatory disease behavior and NOD2/CARD15 genotype but not with risk for surgery in a Hungarian cohort of IBD patients. *Inflamm Bowel Disease* vol. 13 pp. 984-992 2007 (Exhibit 410).
Parkes et al., Susceptibility loci in inflammatory bowel disease. *Lancet* vol. 348 p. 1588 1996 (Exhibit 411).
Parrello et al., Upregulation of the IL-12 receptor beta 2 chain in Crohn's disease. *J Immunol* vol. 165 pp. 7234-7239 2000 (Exhibit 412).
Partanen, J., et al., Low degree of DNA polymorphism in the HLA-linked lymphotoxin (tumor necrosis factor-B) gene. *Scand J. Immunol*. vol. 28 pp. 313-316 1988. (Exhibit 413).
Paul, ed. Fundamental Immunology 4th edition pages Chapter 19 663-665 1998 (Exhibit 414).
Pericak-Vance et al., Approaches to gene mapping in complex human diseases. Wiley-Liss New York 1998 (Exhibit 415).
Perkin Elmer Catalog 1992 p. 12 (Exhibit 416).
Plevy et al, Tumor necrosis factor (TFN) microsatellite associations with HLA-DR2+ patients define crohn's disease (cd) and ulcerative colitis (uc)-specific genotypes, *Gastroenterology*, vol. 106, p. A754 1994 (Exhibit 417).
Plevy et al. TNF-alpha MRNA levels differentiated mucosal inflammation in crohn's disease from ulcerative colitis, *J. Immunology*, vol. 150, p. 10a 1993 (Exhibit 418).
Plevy et al., A role of TNF-alpha and mucosal T-helper-1 cytokines in the pathogenesis of Crohn's disease. *The Journal of Immunology* vol. 84 pp. 1397-1398 2004 (Exhibit 419).
Plevy et al., Increased mucosal tnf-alpha mrna levels and numbers of tnf-alpha producing cells are unique to mucosal inflammation in crohn's disease, *Faseb Journal*, Abstract 5849 vol. 8, p. A1010 Apr. 1994, (Exhibit 420).
Plevy et al., The tumor necrosis factor (TNF) microsatellite haplotype A2B1C2D4E1 correlates with increased TNF production in Crohn's disease. Abstract only AASLD at Digestive disease week 1995 (Exhibit 421).
Plevy et al., Tumor necrosis factor microsatellites define Crohn's disease—associated haplotype on chromosome 6. *Gasteroenterology* vol. 110 pp. 1053-1060 1996 (Exhibit 422).
Pociot et al., Association of tumor necrosis factor and class II major histocompatibility complex alles with secretion of tnf alfa and tnf beta by human mononuclear cells: a possible link to insulin-dependent diabetes mellitus, 1993, Abstract only *Eur. J. Immunology*, vol. 23, 1993 (Exhibit 423).
Pociot, F., et al., "A tumor necrosis factor beta gene polymorphism in relation to monokine secretion and insulin dependent diabetes mellitus." *Scand J. Immunol*., vol. 33 pp. 37-49 1991 (Exhibit 424).
Poicot et al., Polymorphic analyis of the human MHC-linked heat shock protein 70 (HSP70-2) and HSP70-Hom genes in insulin-dependent diabetes mellitus (IDDM). *Scand J Immunol* vol. 38 pp. 491-495 1993 (Exhibit 425).
Polanczyk et al., The protective effect of 17beta-estradiol on experimental autoimmune encephalomyelitis is mediated through estrogen receptor-a. *Americal J of Pathology* vol. 163 pp. 5820-5827 2003 (Exhibit 426).
Potts et al., Using micorbicides to fight the spread of HIV. *Science* vol. 300 p. 431 2003 (Exhibit 427).
Radlmayr, M. et al., The c-insertion mutation of the NOD2 gene is associated with fistulizing and fibrostenotic phenotypes in Crohn'd diseases. *Gasterenterology* vol. 122 pp. 2091-2095 2002 (Exhibit 428).
Rector et al., Mannan-binding lectin (MBL) gene polymorphisms in ulcerative colitis and Crohn's disease. *Genes and Immunity*vol. 2 pp. 323-328 2001 (Exhibit 429).
Reinecker et al., Enhanced secretion of tumor necrosis factor-alpha, IL-6 and IL-1beta by isolated lamina propia mononuclear cells from patients with ulcerative colitis and Crohn's disease *Clin Exp Immunol* vol. 94 pp. 174-181 1993 (Exhibit 430).
Rioux et al., Genome-wide association study identifies new susceptibility loci for Crohn disease and implicates autophagy in disease pathogenesis *Nature Genetics* pp. 1-9 2007 (Exhibit 431).
Rodriguez-Caballero et al., A new simple whole blood flow cytometry-based method for simultaneous identification of activated cells and quantitative evaluation of cytokines released during activation *Laboratory Investigation* vol. 84 pp. 1387-1398 2004 (Exhibit 432).
Roth et al., Familial empiric risk estimates of inflammatory bowel disease in Ashkenazi Jews. *Gastroenterology* vol. 96 pp. 1016-1020 1989 (Exhibit 433).
Roth et al., Geographic origins of Jewish patients with inflammatory bowel disease. *Gastroenterology* vol. 97. pp. 900-904 1989 (Exhibit 434).
Rotter et al., TLR5 polymorphisms are associated with OmpC and CBir1 expression and with severity of Crohn's disease in Ashkenazi Jews. Abstract only 2004. Journal unknown (Exhibit 435).
Rozen et al., Crohn's disease in the Jewish population of Tel-Aviv-Yafo: epidemiologic and clinical aspects. *Gastroenterology* vol. 76 pp. 25-30 1979 (Exhibit 436).
Salem et al., Mediation of the immunomodulatory effect of beta-estradiol on inflammatory response by inhibition of recruitment and activation of inflammatory cells and their gene expression of TNF-alpha and IFN-gamma. *Intl Archives of Allergy and Immunology* Abstract Only. vol. 121 pp. 235-245 2000 (Exhibit 437).
Salem M. L. Estrogen, a double-edged sword: modulation of TH1- and THw-medicated inflammations by differential regualtion of TJ1/TH2 cytokine production. *Inflammation and Allergy* vol. 3 pp. 97-104 2004 (Exhibit 438).
Saruta et al., High frequency haplotypes in the X-chromosome locus TLR8 are associated with both CD and UC in females. 2007 Journal unknown (Exhibit 439).
Saruta et al., TLR8-mediated activation of human monocytes inhibits TL1A expression. *Eur J Immunol* vol. 39 pp. 2195-2202 2009 (Exhibit 440).
Sategna-Guidetti et al., Tumor necrosis factor/cachectin in Crohn's disease—relation of serum concentration to disease activity *Recenti Progressi*, vol. 84, pp. 93-99 1993 (Exhibit 441).
Satsangi et al., The genetics of inflammatory bowel disease. *Gut* vol. 40 pp. 572-574 1997 (Exhibit 442).
Saxon, E. Z. et al., A distinct subset of antineutrophil cytoplasmic antibodies is associated with inflammatory bowel disease. *J Allergy Clin. Immunol*. vol. 86 pp. 202-210 1990 (Exhibit 443).
Schimanski, C. C. et al., Efect of chemokine receptors CXCR4 and CCR7 on the metastatic behavior of human colorectal cancer *Clinical Cancer Research* vol. 11 pp. 1743-1750 2005 (Exhibit 444).

(56) References Cited

OTHER PUBLICATIONS

Schluender et al., Does infliximab influence surgical morbidity or long-term outcome of Ileal pouch-anal anastomosis in patients with ulcerative colitis. Abstract only 2006 Journal unknown (Exhibit 445).
Schluender et al., Does preoperative wireless endoscopic capsule predict long-term outcome after Ileal pouch-anal anastomosis (IPAA)? Abstract only 2006 Journal unknown (Exhibit 446).
Schoelmerich, J. Inflammatory Bowel Diseases: early symptoms and differential (Reprints available from University of Freiburg, Department of Internal Medicine, Hugstetter Strasse 55, D-7800 Freiburg, W. Germany) pp. 2-20 (Exhibit 447).
See, Darryl et al., Increased tumor necrosis factor alpha (TNF-alpha) and natural killer cell (NK) function using an integrative approach in late stage cancers. *Immunological Investigations* vol. 31 pp. 137-153 2002 (Exhibit 448).
Shanahan, F. et al., Inflammatory Bowel Disease. *Textbook of Internal Medicine* W.N. Kelley et al. (editor) 2nd edition J. B. Lippincott Company, Philadelphia vol. 81 pp. 489-502 1992 (Exhibit 449).
Shetty et al., Pharmacogenomics of response to anti-tumor necrosis factor therapy in patients with Crohn's disease. *American Journal of Pharmacogenomics* vol. 2 pp. 215-221 2202 (Exhibit 450).
Shovam et al., Evaluation of the BioPlex 2200 ANA screen: Analysis of 510 healthy subjects: incidence of natural/predictive autoantibodies. *Annals of the New York Academy of Science* vol. 1050 pp. 380-388 2005 (Exhibit 451).
Silman et al., Epidemiology and genetics of rheumatoid arthritis. *Arthritis Research* vol. 4 Supp 3 pp. S265-S272 2002 (Exhibit 452).
Silverberg et al., Evidence for linkage between Crohn's disease (CD) and a locus near the major histocompatibility complex (MHC) on chromosome 6 in a Canadian inflammatory bowel disease (IBD) population. *Gastroenterology* vol. 116:G3560 AGA Abstracts 1999 (Exhibit 453).
Silverberg et al., The HLA DRBL 0103 allele is associated with Crohn's disease (CD) in a Toronto inflammatory bowel disease (IBD) population. *Gastroenterology* vol. 116:G3559 AGA Abstracts 1999 (Exhibit 454).
Singal et al., D6S273 microsatellite polymorphism and susceptibility to Rhematoid Arthritis. *Tissue Antigens* vol. 52 pp. 353-358 1998 (Exhibit 455).
Singal et al., Genetics of rheumatoid arthritis (RA): two separate regions in the major histocompatibility complex contribute to susceptibility to RA. *Immunol Lett* vol. 69 pp. 301-306 1999 (Exhibit 456).
Sitaraman et al., Elevated flagellin-specific immunoglobulins in Crohn's disease. *Am J Physiol Gastrointest Liver Physiol* 288:G403-G406, 2005 (Exhibit 457).
Smith C. et al., Cooperative interactions of LFA-1 and Mac-1 with intercellular adhesion molecule-1 in facilitating adherence and transendothelial migration of human neurophils in vitro. *J Clin Invest* vol. 83 pp. 2008-2017 1998 (Exhibit 458).
Smith et al. Topical estrogen protects against SIV vaginal transmission without evidence of systemic effect. Abstract only. vol. 18 pp. 1637-1643 2004 (Exhibit 459).
Smith et al., Estrogen protects against vaginal transmission of simian immunodeficiency virus. *J Infectious Diseases* vol. 182 pp. 708-715 2000 (Exhibit 460).
Smith, C. W. et al., Recognition of an endothelial determinant for CD18-dependent human neutrophil adherence and transendothelial migration. *J Clin Invest* vol. 82 pp. 1746-1756 1988 (Exhibit 461).
Smith, C., Adherence of neutrophils to canine cardiac myocyyes in vitro is dependent on intercellular adhesion molecule-1. *J Clin Invest* vol. 88 pp. 1216-1223 1991 (Exhibit 462).
Smith, C., Transendothelial Migration, Harlan, J. and Liu D., eds., W. H. Freeman & Co. New York pp. 83-115 1992 (Exhibit 463).
Springer, T. A. et al., Adhesion receptors of the immune system. *Nature* vol. 346 pp. 425-433 1990 (Exhibit 464).
Springer, T. A. et al., Leukocyte adhesion molecules structure function and regulation. New York, Springer-Verlag 1990 Book—Table of Contents Book not included.
Staunton et al. The arrangement of the immunoglobulin-like domains of ICAM-1and binding sites for LFA-1 and rhinovirus. *Cell* vol. 61 pp. 243-254 1990 (Exhibit 466).
Staunton et al., Primary Structure of ICAM-1 demonstrates interaction between member of the immunoglobulin and integring supergene families. *Cell* vol. 52 pp. 925-933 Mar. 25, 1988 (Exhibit 467).
Steer et al., Development of rheumatoid arthritis is not associated with two polymorphisms in the Crohn's disease gene CARD15 *Rheumatology* vol. 42 pp. 304-307 2003 (Exhibit 468).
Stites, D. P., et al., Chapter 22 of the 4th edition of Basic and Clinical Immunology, Lange Medical Publications, Los Altos, California 1982 (Exhibit 469).
Stratagene Catalog 1988 p. 39 (Exhibit 470).
Strater, J. et al., Expression of TRAIL and TRAIL receptors in colon carcinoma: TRAIL-R1 is an independent prognostic parameter. *Clinical Cancer Research* vol. 8 pp. 3734-3740 2002 (Exhibit 471).
Stulik et al., The different expression of proteins recognized by monoclonal anti-heat shock protein 70 (hsp70) antibody in human colonic diseases. *Electrophoresis* vol. 18 pp. 625-628 1997 (Exhibit 472).
Su, X., Different haplotypes of IL12B (p40) genes are associated with clinical Crohn's disease (CD) and with CD patients expressing Cbir1 antibodies, respectively. Abstract only 2007 Journal unknown (Exhibit 473).
Sugaya et al., Gene organization of human NOTCH4 and (CTG)n polymorphism in this human counterpart gene of mouse proto-oncogene Int3. *Gene* vol. 189 pp. 235-244 1997 (Exhibit 474).
Sugaya et al., Three genes in the human MHC class III region near the junction with the class II: gene for receptor of advanced glycosylation end products, PBX2 homeobox gene and a notch homolog, human counterpart of mouse mammary tumor gene int-3. *Genomics* vol. 23 pp. 408-419 1994 (Exhibit 475).
Sullivan et al., Prevalence of a mutation causing C2 deficiency in systemic lupus erythematosus. *J of Rhematology* vol. 21 pp. 1128-1133 1994 (Exhibit 476).
Takedatsu, H., Reduced nuclear factor (NF)-kB expression in cell lines from anti-CBir1-associated NFKB1 haplotypes. Abstract only. 2007 Journal unknown (Exhibit 477).
Takedatsu et al., TL1A (TNFSF15) regulates the development of chronic colitis by modulating both T helper (TH)1 and TH17 activation. *Gastroenterology* vol. 135 pp. 552-567 2008 (Exhibit 478).
Targan et al., Antibodies to CBir1 flagellin define a unique response that is associated independently with complicated Crohn's disease. *Gastroenterology*, vol. 128, 2005, pp. 2020-20289 (Exhibit 479).
Targan et al., Definition of a lamina propia T cells responsive state enhanced cytokine responsiveness of T cells stimulated through the CD2 pathway. *J Immunol* vol. 154 pp. 664-675 1995 (Exhibit 480).
Targan, et al., Antibodies to a novel flagellin (CBir1) define a unique serologic response in Crohn's disease (CD). *Gastroenterology*, Abstract only XP009098183 vol. 126, No. 4, Suppl 2, Apr. 2004, p. A113 (Exhibit 481).
Tarlow J. K. et al., Polymorphism in human IL-1 receptor antagonist gene intron 2 is caused by variable numbers of an 86-bp tandem repeat. *Hum Genet* vol. 91 pp. 403-404 1993 (Exhibit 482).
Taylor et al., Analysis of IBD5-related polymorphisms: IRF1 but not SLC22A4 or SLC22A5 is associated with IBD in Puerto Rican populations. *Digestive Disease Week* Abstract only 2006 Journal unknown (Exhibit 483).
Taylor et al., Genes regulating the expression of antibody to CBir1 flagellin in humans are located within a syntemic region to the major mouse colitogenic locus Cdcs1. *AGA Institute* Abstract #444 p. A-64 2006 (Exhibit 484).
Taylor et al., IL23R haplotypes provide a large population attributable risk for Crohn's disease. *Inflammatory Bowel* vol. 14 pp. 1185-1191 2008 (Exhibit 485).
Taylor et al., Specific clinical and immunological features in Crohn's disease patients are associated with the MHC class III

(56) References Cited

OTHER PUBLICATIONS marker Notch4. *Gastroenterology* Abstract 4830 XP001009809 vol. 118 Supp 2 p. A869 2000 (Exhibit 486).

Taylor K et al., Linkage disequilibrium mapping identifies a Class III major histocompatibility complex (MHC) susceptibility haplotypes to Crohn's disease in Ashkenazi Jews. *Am J Human Genetics* Abstract XP001009810 vol. 65 p. A102 1999 (Exhibit 487).

Thisted. What is a P-value? Department of Statistics and health studies. The University of Chicago. May 1998 (Exhibit 488).

Thomas et al., Estrogen and raloxifen activities on amyloid-beta-induced inflammatory reaction. *Microvascular Research* vol. 61 pp. 28-39 2001 (Exhibit 489).

Tomassini, J. E. et al., cDNA cloning reveals that the major group rhinovirus receptor on HeLa cells in intercellular adhesion molecule-1. *Proc Natl Acad Sci* vol. 86 pp. 4907-4911 1989 (Exhibit 490).

Torok et al., Crohn's disease is associated with a Toll-like receptor-9 polymorphism. *Gastroenterology* vol. 127 pp. 365-368 2004 (Exhibit 491).

Torres et al., The Hermansky-pudlak 1 (HPS1) gene is associated with IBD in Puerto Rico independent of the known HPS1 insertion mutation. Abstract only 2006 Journal unknown (Exhibit 492).

Tountas et al. Heterogenous association between allele 2 of IL-2 receptor antagonist (IL-1RA) and ulcerative colitis in Jewish and non-Jewish populations. Abstract only. *J. Investigative Medicine* XP000673114 vol. 44 1996 (Exhibit 493).

Tountas et al., Genetic association between allele 2 of IL-1 receptor antagonist (IL-1ra) and ulcerative colitis in Los Angeles based hispanic population. Abstract only. *Gastroenterology* XP000673112 vol. 108 1995 (Exhibit 494).

Tountas et al., Increased carriage of allele 2 of IL-1 receptor antagonist (IL-1ra) in Jewish population: the strongest known genetic association in ulcerative colitis. *American Gastroenterology Association* Abstract Only 1996 (Exhibit 495).

Trachtenberg et al., Rare HLA DR-DQ haplotypes associated with inflammatory bowel disease. *Human Immunol* vol. 55 (supp. 1) Abstract #42 p. 59 1997 (Exhibit 496).

Trowsdale et al., Map of the human MHC. *Immunol. Today* vol. 12 pp. 443-446 1991 (Exhibit 497).

Turchan et al., Estrogen protects against the synergistic toxicity by HIV proteins, methamphetamine and cocaine. *BMC Neuroscience*vol. 2 2001 (Exhibit 498).

Udalova, I.A., et al., Highly informative typing of the human TNF locus using six adjacent polymorphic markers *Genomics*, vol. 16 pp. 180-186 1993 (Exhibit 499).

Vaidya et al., The cytotoxic T lymphocyte antigen-4 is a major Graves' disease locus. *Hum Mol Gen* vol. 8 pp. 1195-1199 1999 (Exhibit 500).

Vasiliauskas et al., Marker antibody expression stratifies Crohn's disease into immunilogically homogenous subgroups with distinct clinical characteristics. *Gut* vol. 47 pp. 487-496 2000 (Exhibit 501).

Vasiliauskas et al., Perinuclear antineutrophil cytoplasmic antibodies in patients with Crohn's disease define a clinical subgroups. *Gastroenterology* vol. 110 pp. 1810-1819 1996 (Exhibit 502).

Vavassori et al., CARD15 mutation analysis in an Italian population: Leu1007fsinsC but neither Arg702Trp nor Gly908Arg mutations are associated with Crohn's disease. Inflamm Bowel Dis vol. 10 pp. 116-121 2004 (Exhibit 503).

Verdu et al., Modulatory effects of estrogen in two murine models of experimental colitis . . . *American J Physiology* vol. 283 pp. G27-G36 2002 (Exhibit 504).

Vermiere, S. et al., CARD15 genetic variation in a Quebec population: prevalence, genotype-phenotype relationship and haplotype structure. *Am J Hum Genet* vol. 71 pp. 74-83 2002 (Exhibit 505).

Vermiere, S. et al., Current status of genetics research in inflammatory bowel disease. *Genes and Immunity*, 6:637-645, 2005 (Exhibit 506).

Verthelyi et al. Sex hormone levels correlate with the activity of cytokine-secreting celss in vivo. *Immunology* vol. 100 pp. 384-390 2000 (Exhibit 507).

Voraberger, G. et al., Cloning on the human gene for intercellular adhesion molecule-1 and analysis of its 5'-regulatory region. *J Immunol* vol. 147 pp. 2777-2786 1991 (Exhibit 508).

Warzocha et al., Tumor necrosis factor ligand receptor system can predict treatment outcome of lymphoma patients. *Journal of Clinical Oncology* vol. 15 pp. 499-508 1997 (Exhibit 509).

Webb, G. C., et al., Genetic variability at the human tumor necrosis factor loci. *J. Immunol* vol. 145 pp. 1278-1285 1993 (Exhibit 510).

Weber, J. and May, P., Abundant class of human DNA polymorphisms which can be typed using the polymerase chain reaction. *Am J Hum Genet* vol. 44 pp. 388-396 1989 (Exhibit 511).

Wen et al., TL1A-induced NF-kB activation and c-IAP2 production prevent DR3-mediated apoptosis in TF-1 cells *J of Biological Chemistry* vol. 278 pp. 39251-39258 2003 (Exhibit 512).

Williams et al., Optimization stratagies for the polymerase chain reaction, *Biotechniques*, vol. 7, pp. 762-768 1989 (Exhibit 513).

Wouters et al., Inter- and intraindividual variation of endotoxin- and beta (1->3)-glucan-induced cytokine responses in a whole blood assay. *Toxicology and Industrial Health* vol. 18 pp. 15-27 2002 (Exhibit 514).

Wu et al. Tamoxifen alleviates disease severity and decreases double negative T cells in autoimmune MRL-Ipr/Ipr mice. *Immunology* vol. 100 pp. 110-118 2000 (Exhibit 515).

Wu et al., Tamoxifen decreases renal inflammation and alleviates disease severity in autoimmune NZB/W F1 mice. *Scandinavian Journal of Immunology* vol. 52 pp. 393-400 2000 (Exhibit 516).

Xiao et al., Interaction of Cocksackievirus A21 with its cellular receptor ICAM-1. *J Virol* vol. 75 pp. 2444-2451 2001. (Exhibit 517).

Yamamoto-Furusho et al., Complotype SC30 is associated with susceptibility to develop ulcerative colitis in Mexicans. *J Clin Gasteroenterology* vol. 27 pp. 178-180 1998 (Exhibit 518).

Yamazaki et al., Absence of mutation in the NOD2/CARD15 gene among 483 Japanese patients with Crohn's disease. *Hum Mol Genet* vol. 47 pp. 469-472 2002 (Exhibit 519).

Yamazaki et al., Association analysis of genetic variants in IL23R, ATG16L1 and 5p13.1 loci with Crohn's disease in Japanese patients. *J Hum Genet* vol. 52 pp. 575-582 2007 (Exhibit 520).

Yamazaki et al., Single nucleotide polymorphisms in TNFSF15 confers susceptibility to Crohn's disease. *Hum Mol Genet* vol. 14 pp. 3499-3506 2005 (Exhibit 521).

Yang and Rotter, Genetic aspects of idiopathic inflammatory bowel disease. Kirschner and Shorter (Eds.), *Inflammatory Bowel Disease*Baltimore: Williams and Wilkins pp. 301-331 1195 (Exhibit 522).

Yang et al. The R241 allele if ICAM-1 is associated with a distinct clinical subgroup of Crohn's disease (CD) characterized by perinuclear ANCA (pANCA) production. Abstract only. *American Gastroenterological Association and American Association for the study of Liver disease*. May 19-22, 1996 (Exhibit 523).

Yang et al., Familial empirical risks for inflammatory bowel disease: differences between Jews and non-Jews. *Gut* vol. 34 pp. 517-524 1993 (Exhibit 524).

Yang et al., Intercellular adhesion molecule 1 gene association with immunologic subsets of inflammatory bowel disease. *Gastroenterology* vol. 109 pp. 440-448 1995 (Exhibit 525).

Yang et al., Linkage of Crohn's disease to the major histocompatibility complex region is detected by multiple non-parametric analyses. *Gut* vol. 44 p. 519-526 1999 (Exhibit 526).

Yang H., et al., Ulcerative colitis: a genetically heterogenous disorder defined by genetic (HLA class II) and subclinical (antineutrophil cytoplasmic antibodies) markers *J. Clin. Invest*., vol. 92, pp. 1080-1084 1993 (Exhibit 527).

Yang, H. et al., Association of intercellular adhesion molecule-1 (ICAM-1) gene with subsets of Inflammatory Bowel Disease (IBD) stratified by anti-neutrophil cytoplasmic antibodies (ANCAs). *Clinical Research* Abstract only vol. 42 No. 1 pp. 76A 1994 (Exhibit 528).

Yang, H. et al., Genetic Heterogeneity within UC and Crohn's defined by anti-neutrophil cytoplasmic antibodies (ANCAs) and

(56) References Cited

OTHER PUBLICATIONS intercellular adhesion molecule-1 (ICAM-1) polymorphisms. *Gastroenterology* vol. 106 No. 4. p. A794 AGA Abstract 1994 (Exhibit 529).
Yoon et al., Decreased potency of the *Vibrio cholerae* sheathed flagellum to trigger host innate immunity. *Infection and Immunity* vol. 76 pp. 1282-1288 2008 (Exhibit 530).
Younes, A. et al., Clinical implication of the tumor necrosis factor family in benign and malignant hematologic disorders. *Cancer* vol. 98 pp. 458-467 2003 (Exhibit 531).
Younes, A. et al., Emerging applications of the tumor necrosis factor family if ligands and receptors in cancer therapy. *J Clin Oncol* vol. 21 pp. 3526-3534 2003 (Exhibit 532).
Zhang et al. Estrogen affects the differentiation and function of splenic monocyte-derived dendritic cells from normal rats. Abstract Only. vol. 20 pp. 129-134 2004 (Exhibit 533).
Zhang et al., Critical role of IL-17 receptor signaling in acute TNBS-induced colitis. *Inflamm Bowel Dis* vol. 12 pp. 382-388 2006 (Exhibit 534).
Ziegler et al., Detectable serum flagellin and liposaccharide and upregulated anti-flagellin and liposaccharide immunoglobulins in human short bowel syndrome. *Am J Physiol Regul Integr Comp Physiol* vol. 294 pp. R402-R410 2008 (Exhibit 535).
Office Action for U.S. Appl. No. 12/528,668 dated Sep. 2, 2011 (Exhibit 536).
Office Action for U.S. Appl. No. 12/529,106 dated Oct. 14, 2011 (Exhibit 537).
Prehn et al., The T Cell Costimulator TL1A Is Induced by Fc R Signaling in Human Monocytes and Dendritic Cells. *J Immunol* vol. 178 pp. 4033-4038 2007 (Exhibit 538).
Takedatsu et al., Linkage of CD-related serological phenotypes: NFKB1 haplotypes are associated with anti-CBir1 & ASCA, and show reduced NF-κB activation. *Gut* vol. 58 pp. 60-67 2009 (Exhibit 539).
McGovern et al., Genetic epistasis of IL23/1L17 pathway genes in Crohn's disease. *Inflamm Bowel Dis*. vol. 15 pp. 883-889 2009 (Exhibit 540).
Michelsen et al., IBD-Associated TL1A Gene (TNFSF15) Haplotypes Determine Increased Expression of TL1A Protein. PLoS ONE vol. 4 e4719 2009 (Exhibit 541).
Office Action for U.S. Appl. No. 12/527,376 dated Oct. 19, 2011 (Exhibit 542).
Redon et al., Global variation in copy number in Genome. Nature vol. 444 pp. 444-454 2006 (Exhibit 543).
Zaahl et al., Analysis of the three common mutations in the CARD15 gene (R702W, G908R and 1007fs) in South African colored patients with inflammatory bowel disease. *Molecular and Cellular Probes* pp. 278-281 2005 (Exhibit 544).
Franke et al. Replication of signals from recent studies of Crohn's disease identifies previously unknown disease loci for ulcerative colitis. Nature Genetics (2008). 40(6): 713-715.
Haritunians et al. Genetic predictors of medically refractory ulcerative colities. Inflamm Bowel Dis (2010). 16(11):1830-1840, 21 pages.
Hoh et al. Trimming, weighting, and grouping SNPs in human case-control association studies. Genome Research (2001). 11:2115-2119.
Queiroz et al. Immune response and gene polymorphism profiles in Crohn's disease and ulcerative colitis. Inflamm Bowel Dis (2009). 15:353-358.
PCT/US2015/029101 International Search Report and Written Opinion dated Aug. 11, 2015; 10 pages.

* cited by examiner

FIG. 3A (Table 1).

<table>
<tr><th>Chr</th><th>SNP</th><th>Position129</th><th>Risk_allele</th><th>Loci</th></tr>
<tr><td>1</td><td>rs746503</td><td>54842574</td><td>A</td><td>ACOT11 | FAM151A | C1orf175 | 645442 |</td></tr>
<tr><td>1</td><td>rs2275612</td><td>95140004</td><td>A</td><td>CNN3 | SLC44A3 | 646896 | 729970 |</td></tr>
<tr><td>1</td><td>rs7550055</td><td>157045388</td><td>C</td><td>MNDA | OR6N2 | OR2AQ1P | OR10AA1P | OR6K4P | OR6N1 | OR6K3 | OR6K5P | 646377 |</td></tr>
<tr><td>1</td><td>rs7367845</td><td>224512151</td><td>A</td><td>ACBD3 | MIXL1 | LIN9 | 100128832 |</td></tr>
<tr><td>2</td><td>rs1448901</td><td>206961885</td><td>G</td><td>ADAM23 | 100132849 |</td></tr>
<tr><td>2</td><td>rs4487082</td><td>229432205</td><td>A</td><td>2q36.3</td></tr>
<tr><td>3</td><td>rs900569</td><td>41834977</td><td>G</td><td>ULK4 |</td></tr>
<tr><td>3</td><td>rs924022</td><td>65824936</td><td>A</td><td>MAGI1 |</td></tr>
<tr><td>3</td><td>rs9843732</td><td>135505746</td><td>G</td><td>RYK |</td></tr>
<tr><td>4</td><td>rs2286461</td><td>15572771</td><td>G</td><td>PROM1 | FGFBP1 | FGFBP2 | 100130067 |</td></tr>
<tr><td>4</td><td>rs12650313</td><td>41401850</td><td>A</td><td>LIMCH1 | 100128654 |</td></tr>
<tr><td>4</td><td>rs1399403</td><td>108639264</td><td>A</td><td>4q25</td></tr>
<tr><td>4</td><td>rs7675371</td><td>116049368</td><td>G</td><td>NDST4 |</td></tr>
<tr><td>5</td><td>rs3846599</td><td>10308821</td><td>A</td><td>MARCH6 | CCT5 | FAM173B | MIR378 |</td></tr>
<tr><td>5</td><td>rs6596684</td><td>105972832</td><td>G</td><td>345571 |</td></tr>
<tr><td>6</td><td>rs1536242</td><td>6876009</td><td>G</td><td>6p25.1</td></tr>
<tr><td>6</td><td>rs17207986</td><td>32187545</td><td>G</td><td>ATF6B | RNF5 | PPT2 | EGFL8 | 653033 |</td></tr>
<tr><td>6</td><td>rs777649</td><td>68925053</td><td>A</td><td>642902 |</td></tr>
<tr><td>7</td><td>rs11764116</td><td>18766938</td><td>A</td><td>HDAC9 |</td></tr>
<tr><td>7</td><td>rs4722456</td><td>25338225</td><td>G</td><td>100131016 |</td></tr>
<tr><td>7</td><td>rs929351</td><td>81695829</td><td>A</td><td>CACNA2D1 |</td></tr>
<tr><td>8</td><td>rs2980654</td><td>6480608</td><td>G</td><td>ANGPT2 | AGPAT5 | MCPH1 | 100131112 | 100132301 |</td></tr>
<tr><td>8</td><td>rs6994721</td><td>76220268</td><td>A</td><td>8q21.11</td></tr>
<tr><td>8</td><td>rs4734754</td><td>105347978</td><td>A</td><td>RIMS2 | TM7SF4 |</td></tr>
<tr><td>9</td><td>rs7861972</td><td>6759692</td><td>A</td><td>JMJD2C | SNRPEL1 |</td></tr>
</table>

FIG. 3B

<table>
<tr><td>9</td><td>rs3118292</td><td>25133480</td><td>G</td><td>9p21.3</td></tr>
<tr><td>9</td><td>rs10817934</td><td>118589872</td><td>G</td><td>ASTN2 |</td></tr>
<tr><td>11</td><td>rs2403456</td><td>11134390</td><td>A</td><td>11p15.3</td></tr>
<tr><td>11</td><td>rs1461898</td><td>37546808</td><td>G</td><td>100132895 |<br>100132631 |</td></tr>
<tr><td>11</td><td>rs6591765</td><td>62674829</td><td>G</td><td>SLC22A24 | SLC22A25 | SLC22A10 |</td></tr>
<tr><td>12</td><td>rs887357</td><td>3344906</td><td>A</td><td>643119 | 728230 | 100128253 |</td></tr>
<tr><td>12</td><td>rs526058</td><td>24326688</td><td>G</td><td>12p12.1</td></tr>
<tr><td>13</td><td>rs7319358</td><td>78448935</td><td>A</td><td>13q31.1</td></tr>
<tr><td>14</td><td>rs1956388</td><td>28202628</td><td>G</td><td>14q12</td></tr>
<tr><td>14</td><td>rs11156667</td><td>30906111</td><td>G</td><td>GPR33 | HEATR5A | NUBPL | C14orf126 |<br>728852 |</td></tr>
<tr><td>14</td><td>rs10133064</td><td>85844148</td><td>C</td><td>14q31.3</td></tr>
<tr><td>14</td><td>rs8020281</td><td>94436179</td><td>A</td><td>14q32.13</td></tr>
<tr><td>15</td><td>rs965353</td><td>57847498</td><td>G</td><td>BNIP2 | 100130107 | GTF2A2 |</td></tr>
<tr><td>16</td><td>rs305087</td><td>84539747</td><td>A</td><td>100131952 |</td></tr>
<tr><td>17</td><td>rs759258</td><td>52483547</td><td>A</td><td>AKAP1 |</td></tr>
<tr><td>19</td><td>rs2967682</td><td>8644532</td><td>C</td><td>MYO1F | ADAMTS10 | OR2Z1 | 390880 |</td></tr>
<tr><td>19</td><td>rs2293683</td><td>12900284</td><td>G</td><td>CALR | DNASE2 | GCDH | FARSA | NFIX | RAD23A | PRDX2 | KLF1 |<br>RTBDN | GADD45GIP1 | DAND5 | SYCE2 |</td></tr>
<tr><td>20</td><td>rs6034134</td><td>15182479</td><td>C</td><td>MACROD2 |</td></tr>
<tr><td>20</td><td>rs10485594</td><td>19772393</td><td>A</td><td>RIN2 | 644298 |</td></tr>
<tr><td>20</td><td>rs6059104</td><td>31185354</td><td>G</td><td>PLUNC | C20orf71 | C20orf70 | C20orf186 | 317716 | 391242 |</td></tr>
<tr><td>21</td><td>rs2831462</td><td>28370367</td><td>A</td><td>21q21.3</td></tr>
</table>

FIG. 4

Sensitivity/ Specificity (cut-off=.5)
Original Data with logistic regression

| | |
|---|---|
| Sensitivity | 0.793 |
| Specificity | 0.858 |

1000 times of 10 fold Cross-Validation data sets with logistic regression

| Variable | N | Mean | Std Dev | Minimum | Maximum |
|---|---|---|---|---|---|
| Sensitivity | 1000 | 0.789 | 0.0067 | 0.758 | 0.793 |
| Specificity | 1000 | 0.859 | 0.0021 | 0.858 | 0.870 |

Hazard Ratio
Original Data

1.313

1000 fold Bootstrapping

| N | Mean | Std Dev | Minimum | Maximum |
|---|---|---|---|---|
| 1000 | 1.314 | 0.017 | 1.269 | 1.372 |

FIG. 5A (Table 2)

| Chr* | SNP | Position* | Minor Allele | P-value | Odds Ratio | Stat | Loci** |
|---|---|---|---|---|---|---|---|
| 1 | rs260970 | 39323829 | G | 2.38E-04 | 1.594 | 3.675 | MACF1 \| 643910 \| |
| 1 | rs6697447 | 54219515 | A | 2.06E-04 | 0.4481 | -3.712 | HSPB11 \| YIPF1 \| C1orf83 \| |
| 1 | rs746503 | 54842574 | A | 2.27E-04 | 1.475 | 3.687 | ACOT11 \| FAM151A \| C1orf175 \| 645442 \| |
| 1 | rs2275612 | 95140004 | A | 1.87E-04 | 1.838 | 3.736 | CNN3 \| SLC44A3 \| 646896 \| 729970 \| |
| 1 | rs4847368 | 95149626 | G | 7.75E-05 | 1.976 | 3.952 | CNN3 \| 646896 \| 729970 \| |
| 1 | rs2298162 | 95221621 | G | 2.85E-04 | 0.6668 | -3.628 | CNN3 \| ALG14 \| |
| 1 | rs7550055 | 157045388 | C | 1.35E-04 | 1.571 | 3.818 | MNDA \| OR6N2 \| OR10AA1P \| OR6K4P \| OR6N1 \| OR6K3 \| OR6K5P \| 646377 \| |
| 1 | rs7367845 | 224512151 | A | 2.55E-04 | 1.475 | 3.657 | ACBD3 \| LIN9 \| |
| 1 | rs9286999 | 224561138 | A | 1.61E-04 | 1.491 | 3.773 | LIN9 \| 100128832 \| |
| 2 | rs892878 | 137588330 | A | 2.78E-04 | 0.6726 | -3.635 | THSD7B \| |
| 2 | rs1560579 | 137592445 | A | 2.67E-04 | 0.6326 | -3.646 | THSD7B \| |
| 2 | rs9287461 | 137593668 | G | 8.64E-05 | 0.6156 | -3.926 | THSD7B \| |
| 2 | rs958323 | 137606935 | G | 1.85E-04 | 0.6408 | -3.738 | THSD7B \| |
| 2 | rs1483148 | 142036240 | C | 1.59E-04 | 0.6225 | -3.777 | LRP1B \| |
| 2 | rs1448901 | 206961885 | G | 2.13E-05 | 1.673 | 4.251 | ADAM23 \| |
| 2 | rs7565690 | 224105705 | A | 2.10E-04 | 0.5414 | -3.706 | |
| 2 | rs4487082 | 229432205 | G | 2.03E-04 | 0.4091 | -3.716 | |
| 3 | rs403961 | 1575422 | G | 2.09E-04 | 1.495 | 3.708 | |
| 3 | rs924022 | 65824936 | G | 1.98E-04 | 0.5251 | -3.721 | MAGI1 \| |
| 3 | rs10511119 | 79943297 | G | 2.87E-04 | 0.6796 | -3.627 | |
| 3 | rs9682694 | 114378369 | G | 1.47E-04 | 1.549 | 3.797 | BOC \| |

FIG. 5B

<table>
<tr><td>3</td><td>rs4839637</td><td>144422638</td><td>A</td><td>2.15E-04</td><td>1.501</td><td>3.701</td><td></td></tr>
<tr><td>4</td><td>rs2286461</td><td>15572771</td><td>G</td><td>1.86E-04</td><td>1.487</td><td>3.738</td><td>PROM1 | FGFBP1 | FGFBP2 | 100130067 |</td></tr>
<tr><td>4</td><td>rs12650313</td><td>41401850</td><td>A</td><td>2.57E-04</td><td>1.877</td><td>3.655</td><td>LIMCH1 | 100128654 |</td></tr>
<tr><td>4</td><td>rs1546318</td><td>79168396</td><td>C</td><td>9.31E-05</td><td>1.932</td><td>3.908</td><td>FRAS1 | 391670 | 100128297 |</td></tr>
<tr><td>4</td><td>rs1393644</td><td>79175731</td><td>C</td><td>9.19E-05</td><td>1.93</td><td>3.911</td><td>FRAS1 | 391670 | 100128297 |</td></tr>
<tr><td>4</td><td>rs1399403</td><td>108639264</td><td>A</td><td>1.60E-04</td><td>1.538</td><td>3.775</td><td></td></tr>
<tr><td>4</td><td>rs11098020</td><td>110122894</td><td>A</td><td>1.90E-04</td><td>1.777</td><td>3.732</td><td>COL25A1 |</td></tr>
<tr><td>4</td><td>rs7675371</td><td>116049368</td><td>A</td><td>2.64E-04</td><td>0.58</td><td>-3.648</td><td>NDST4 |</td></tr>
<tr><td>4</td><td>rs6821443</td><td>122566710</td><td>C</td><td>2.90E-04</td><td>0.669</td><td>-3.624</td><td>QRFPR | 391692 | 729109 | 729112 |</td></tr>
<tr><td>5</td><td>rs3846599</td><td>10308821</td><td>A</td><td>1.06E-04</td><td>1.517</td><td>3.877</td><td>MARCH6 | CCT5 | FAM173B | MIR378 |</td></tr>
<tr><td>5</td><td>rs12652447</td><td>15727635</td><td>A</td><td>3.86E-05</td><td>1.524</td><td>4.115</td><td>FBXL7 |</td></tr>
<tr><td>5</td><td>rs6596684</td><td>105972832</td><td>G</td><td>1.13E-04</td><td>1.53</td><td>3.861</td><td>345571 |</td></tr>
<tr><td>5</td><td>rs6870711</td><td>126446993</td><td>A</td><td>1.98E-04</td><td>2.404</td><td>3.722</td><td>MARCH3 | 401207 |</td></tr>
<tr><td>6</td><td>rs1536242</td><td>6876009</td><td>A</td><td>2.71E-04</td><td>0.62</td><td>-3.642</td><td></td></tr>
<tr><td>6</td><td>rs17207986</td><td>32187545</td><td>G</td><td>4.71E-05</td><td>2.297</td><td>4.069</td><td>ATF6B | RNF5 | PPT2 | EGFL8 | 653033 |</td></tr>
<tr><td>6</td><td>rs3734263</td><td>34946407</td><td>G</td><td>2.37E-04</td><td>0.4474</td><td>-3.676</td><td>TAF11 | ANKS1A | UHRF1BP1 |</td></tr>
<tr><td>6</td><td>rs9470224</td><td>36248614</td><td>A</td><td>1.70E-04</td><td>1.843</td><td>3.759</td><td>BRPF3 | PNPLA1 |</td></tr>
<tr><td>6</td><td>rs777649</td><td>68925053</td><td>A</td><td>1.10E-05</td><td>1.618</td><td>4.396</td><td>642902 |</td></tr>
<tr><td>6</td><td>rs3777505</td><td>75937343</td><td>A</td><td>1.04E-04</td><td>2.526</td><td>3.881</td><td>COL12A1 |</td></tr>
<tr><td>6</td><td>rs6908055</td><td>107015887</td><td>G</td><td>1.13E-04</td><td>1.67</td><td>3.861</td><td>AIM1 |</td></tr>
<tr><td>6</td><td>rs9400010</td><td>107027893</td><td>G</td><td>1.44E-04</td><td>1.56</td><td>3.802</td><td>AIM1 |</td></tr>
<tr><td>7</td><td>rs11760555</td><td>12563060</td><td>G</td><td>2.92E-04</td><td>0.6713</td><td>-3.622</td><td>SCIN |</td></tr>
<tr><td>7</td><td>rs4722456</td><td>25338225</td><td>A</td><td>9.50E-05</td><td>0.6644</td><td>-3.903</td><td>100131016 |</td></tr>
<tr><td>7</td><td>rs13244827</td><td>131735522</td><td>G</td><td>1.68E-04</td><td>0.3415</td><td>-3.763</td><td>PLXNA4 |</td></tr>
<tr><td>7</td><td>rs851685</td><td>147125736</td><td>A</td><td>2.25E-04</td><td>1.546</td><td>3.69</td><td>CNTNAP2 |</td></tr>
<tr><td>8</td><td>rs2978310</td><td>2701133</td><td>A</td><td>2.68E-04</td><td>1.496</td><td>3.644</td><td></td></tr>
<tr><td>8</td><td>rs1471474</td><td>76216530</td><td>A</td><td>1.12E-04</td><td>0.6541</td><td>-3.864</td><td></td></tr>
<tr><td>8</td><td>rs6994721</td><td>76220268</td><td>G</td><td>7.63E-05</td><td>0.6521</td><td>-3.956</td><td></td></tr>
<tr><td>8</td><td>rs4734754</td><td>105347978</td><td>C</td><td>1.57E-04</td><td>0.6496</td><td>-3.78</td><td>TM7SF4 |</td></tr>
<tr><td>8</td><td>rs4734757</td><td>105355266</td><td>A</td><td>1.95E-04</td><td>0.6537</td><td>-3.725</td><td>TM7SF4 |</td></tr>
<tr><td>8</td><td>rs263241</td><td>131931602</td><td>A</td><td>2.44E-04</td><td>1.456</td><td>3.669</td><td>ADCY8 |</td></tr>
</table>

FIG. 5C

| | | | | | | | |
|---|---|---|---|---|---|---|---|
| 9 | rs7861972 | 6759692 | G | 2.34E-04 | 0.473 | -3.68 | JMJD2C \| SNRPEL1 \| |
| 9 | rs11265961 | 91638884 | A | 2.12E-05 | 1.586 | 4.252 | |
| 9 | rs2145929 | 116621761 | G | 2.44E-04 | 1.634 | 3.668 | TNFSF15 \| 645266 \| 100129633 \| |
| 9 | rs10817934 | 118589872 | A | 1.39E-04 | 0.6364 | -3.811 | ASTN2 \| |
| 10 | rs3793792 | 50520169 | A | 2.94E-04 | 1.481 | 3.62 | CHAT \| C10orf53 \| |
| 10 | rs518525 | 129520863 | A | 1.65E-04 | 1.488 | 3.767 | PTPRE \| 387720 \| |
| 11 | rs2403456 | 11134390 | A | 1.08E-04 | 2.413 | 3.872 | |
| 11 | rs4356200 | 37489093 | A | 6.49E-05 | 0.6231 | -3.994 | 100132895 \| |
| 11 | rs1461898 | 37546808 | A | 5.46E-05 | 0.5881 | -4.035 | |
| 11 | rs1075025 | 37582318 | G | 2.38E-04 | 0.6141 | -3.675 | |
| 11 | rs767289 | 37624038 | G | 3.99E-05 | 0.6274 | -4.108 | 100132631 \| |
| 11 | rs10837504 | 40775682 | A | 1.50E-04 | 1.649 | 3.792 | |
| 11 | rs6591765 | 62674829 | A | 7.84E-05 | 0.6468 | -3.949 | SLC22A24 \| |
| 11 | rs7949840 | 62741273 | G | 6.75E-05 | 0.6511 | -3.985 | SLC22A24 \| SLC22A25 \| SLC22A10 \| |
| 11 | rs11231409 | 62741444 | G | 7.46E-05 | 0.6527 | -3.961 | SLC22A24 \| SLC22A25 \| SLC22A10 \| |
| 12 | rs887357 | 3344906 | C | 2.16E-04 | 0.5947 | -3.699 | 643119 \| 728230 \| 100128253 \| |
| 12 | rs970063 | 13424516 | A | 1.87E-04 | 1.48 | 3.736 | C12orf36 \| |
| 12 | rs12581840 | 19725418 | G | 1.05E-04 | 0.6566 | -3.88 | |
| 12 | rs526058 | 24326688 | A | 6.51E-05 | 0.6009 | -3.994 | |
| 12 | rs1144720 | 32157518 | G | 2.82E-05 | 1.571 | 4.188 | BICD1 \| 729457 \| |
| 12 | rs1613650 | 32169080 | G | 2.65E-04 | 1.507 | 3.647 | BICD1 \| 729457 \| |
| 12 | rs2683471 | 32171607 | A | 2.14E-04 | 1.518 | 3.702 | BICD1 \| 729457 \| |
| 14 | rs1956388 | 28202628 | A | 1.32E-04 | 0.672 | -3.822 | |
| 14 | rs11156667 | 30906111 | A | 1.75E-05 | 0.6296 | -4.294 | HEATR5A \| 728852 \| |
| 14 | rs9323262 | 53863964 | A | 2.69E-04 | 0.5639 | -3.644 | CDKN3 \| |
| 14 | rs10133064 | 85844148 | A | 2.03E-04 | 0.4618 | -3.715 | |
| 14 | rs35795554 | 85854768 | C | 2.56E-04 | 0.4743 | -3.656 | |
| 15 | rs7172534 | 24855745 | G | 2.52E-04 | 1.503 | 3.661 | GABRG3 \| |
| 15 | rs965355 | 57847116 | G | 1.04E-04 | 1.584 | 3.881 | BNIP2 \| 100130107 \| |
| 15 | rs965353 | 57847498 | G | 1.38E-04 | 1.569 | 3.811 | BNIP2 \| 100130107 \| |
| 15 | rs10519111 | 59169989 | G | 1.08E-04 | 1.719 | 3.872 | RORA \| |

FIG. 5D

| | | | | | | | |
|---|---|---|---|---|---|---|---|
| 15 | rs990422 | 98377291 | A | 2.97E-04 | 1.533 | 3.618 | ADAMTS17 \| |
| 15 | rs1585933 | 98403238 | G | 6.14E-05 | 1.605 | 4.007 | ADAMTS17 \| |
| 16 | rs305087 | 84539747 | G | 4.72E-05 | 0.5364 | -4.069 | 100131952 \| |
| 17 | rs759258 | 52483547 | A | 2.39E-04 | 1.561 | 3.674 | AKAP1 \| |
| 18 | rs3848490 | 2326366 | A | 2.97E-04 | 1.48 | 3.618 | |
| 18 | rs8088744 | 64685792 | A | 1.72E-04 | 0.6688 | -3.757 | CCDC102B \| |
| 19 | rs2967682 | 8644532 | A | 9.96E-05 | 0.6538 | -3.892 | MYO1F \| ADAMTS10 \| OR2Z1 \| 390880 \| |
| 19 | rs11085825 | 12868458 | A | 6.05E-05 | 0.6309 | -4.011 | CALR \| DNASE2 \| GCDH \| NFIX \| RAD23A \| PRDX2 \| KLF1 \| RTBDN \| DAND5 \| SYCE2 \| |
| 19 | rs2293683 | 12900284 | A | 8.35E-05 | 0.636 | -3.934 | CALR \| DNASE2 \| FARSA \| NFIX \| RAD23A \| KLF1 \| RTBDN \| DAND5 \| SYCE2 \| |
| 19 | rs1010222 | 12909608 | A | 1.52E-04 | 0.6469 | -3.788 | CALR \| DNASE2 \| FARSA \| NFIX \| RAD23A \| KLF1 \| DAND5 \| SYCE2 \| |
| 19 | rs4808408 | 15881376 | G | 1.47E-05 | 0.628 | -4.334 | CYP4F2 \| CYP4F11 \| OR10H4 \| 440511 \| 646596 \| 729645 \| 729654 \| |
| 19 | rs12459140 | 15882888 | G | 1.52E-05 | 0.6287 | -4.326 | CYP4F2 \| CYP4F11 \| OR10H4 \| 440511 \| 646596 \| 729645 \| 729654 \| |
| 20 | rs6034134 | 15182479 | A | 1.00E-04 | 0.6518 | -3.89 | MACROD2 \| |
| 20 | rs10485594 | 19772393 | A | 6.91E-05 | 2.126 | 3.979 | RIN2 \| 644298 \| |
| 20 | rs6059101 | 31182314 | A | 6.54E-05 | 0.601 | -3.993 | C20orf71 \| C20orf70 \| 317716 \| 391242 \| |
| 20 | rs6059104 | 31185354 | A | 1.55E-04 | 0.6545 | -3.784 | C20orf71 \| C20orf70 \| 317716 \| 391242 \| |
| 22 | rs909502 | 47050966 | A | 2.65E-04 | 1.483 | 3.647 | |

FIG. 6A (Table 3)

| Chr | SNP | Position129 | Minor_allele | P_value | Loci |
|---|---|---|---|---|---|
| 1 | rs1392127 | 55788503 | A | 5.25E-05 | 400754 \| |
| 1 | rs2298162 | 95221621 | G | 1.58E-05 | CNN3 \| ALG14 \| |
| 2 | rs1448901 | 206961885 | G | 5.08E-05 | ADAM23 \| |
| 2 | rs3791994 | 207718164 | A | 2.66E-05 | KLF7 \| |
| 3 | rs900569 | 41834977 | G | 1.91E-05 | ULK4 \| |
| 3 | rs6796430 | 73950170 | A | 5.77E-05 | |
| 3 | rs9843732 | 135505746 | G | 6.00E-05 | RYK \| |
| 4 | rs1013300 | 13204657 | G | 9.52E-05 | NKX3-2 \| BOD1L \| 285548 \| |
| 4 | rs1491262 | 13301398 | A | 9.20E-05 | BOD1L \| 644868 \| |
| 4 | rs17476066 | 15461202 | G | 4.87E-05 | CD38 \| |
| 4 | rs2608816 | 39103204 | G | 9.90E-05 | RFC1 \| LIAS \| KLB \| 642885 \| |
| 4 | rs6811556 | 180521808 | A | 9.46E-06 | |
| 5 | rs6892546 | 5873530 | G | 7.03E-05 | |
| 5 | rs4571457 | 107862146 | G | 7.40E-06 | |
| 6 | rs9468256 | 28003483 | A | 8.81E-05 | HIST1H1B \| HIST1H2AK \| HIST1H2AM \| HIST1H3I \| HIST1H3J \| HIST1H4K \| HIST1H4L \| OR2B6 \| OR2W6P \| OR2W4P \| OR2B2 \| |
| 6 | rs2116984 | 28040741 | A | 4.39E-05 | HIST1H1B \| HIST1H2AM \| HIST1H3I \| HIST1H3J \| HIST1H4L \| OR2B6 \| OR2W4P \| OR2W2P \| OR2B7P \| OR2B2 \| |
| 6 | rs1012411 | 30440534 | C | 8.56E-05 | HCG18 \| 646491 \| 100129192 \| |
| 6 | rs9501030 | 30907378 | A | 4.27E-06 | DDR1 \| GTF2H4 \| IER3 \| FLOT1 \| VARS2 \| 646553 \| MIR588 \| |
| 6 | rs9295930 | 30957801 | A | 9.38E-05 | DDR1 \| GTF2H4 \| VARS2 \| DPCR1 \| 646553 \| 646570 \| |

FIG. 6B

<table>
<tr><td></td><td></td><td></td><td></td><td></td><td>MIR588 | 729778 |</td></tr>
<tr><td>6</td><td>rs10947114</td><td>31010160</td><td>A</td><td>7.87E-05</td><td>VARS2 | DPCR1 | SFTA2 | MUC21 | 646563 | 646570 | MIR588 | 729778 | 729792 |</td></tr>
<tr><td>6</td><td>rs537160</td><td>32024379</td><td>A</td><td>1.44E-05</td><td>CFB | C2 | C4A | C4B | NEU1 | SKIV2L | RDBP | STK19 | EHMT2 | SLC44A4 | ZBTB12 |</td></tr>
<tr><td>6</td><td>rs4151657</td><td>32025519</td><td>G</td><td>5.17E-05</td><td>CFB | C2 | C4A | C4B | NEU1 | SKIV2L | RDBP | STK19 | EHMT2 | SLC44A4 | ZBTB12 |</td></tr>
<tr><td>6</td><td>rs9267845</td><td>32301676</td><td>T</td><td>4.04E-05</td><td>AGER | ATF6B | NOTCH4 | PBX2 | AGPAT1 | GPSM3 | FKBPL | PRRT1 | 401252 | 100130536 |</td></tr>
<tr><td>6</td><td>rs6910071</td><td>32390832</td><td>G</td><td>1.84E-05</td><td>NOTCH4 | C6orf10 |</td></tr>
<tr><td>6</td><td>rs2894253</td><td>32453518</td><td>C</td><td>1.95E-05</td><td>HLA-DRA | C6orf10 | 646668 |</td></tr>
<tr><td>6</td><td>rs34330585</td><td>32498681</td><td>G</td><td>4.30E-05</td><td>HLA-DRA | C6orf10 | BTNL2 | 646668 |</td></tr>
<tr><td>7</td><td>rs2158767</td><td>17019311</td><td>G</td><td>7.51E-05</td><td></td></tr>
<tr><td>7</td><td>rs1178163</td><td>18754088</td><td>A</td><td>5.55E-06</td><td>HDAC9 |</td></tr>
<tr><td>7</td><td>rs11764116</td><td>18766938</td><td>A</td><td>2.26E-06</td><td>HDAC9 |</td></tr>
<tr><td>7</td><td>rs2389992</td><td>18903915</td><td>G</td><td>1.30E-05</td><td>HDAC9 |</td></tr>
<tr><td>7</td><td>rs929351</td><td>81695829</td><td>C</td><td>8.33E-06</td><td>CACNA2D1 |</td></tr>
<tr><td>8</td><td>rs2980654</td><td>6480608</td><td>G</td><td>6.62E-05</td><td>ANGPT2 | AGPAT5 | MCPH1 | 100131112 | 100132301 |</td></tr>
<tr><td>8</td><td>rs6474026</td><td>56956047</td><td>G</td><td>7.63E-05</td><td>LYN |</td></tr>
<tr><td>8</td><td>rs2383847</td><td>73166848</td><td>G</td><td>8.52E-05</td><td>TRPA1 |</td></tr>
<tr><td>8</td><td>rs2954870</td><td>75995015</td><td>G</td><td>8.76E-05</td><td>CRISPLD1 |</td></tr>
<tr><td>9</td><td>rs3118292</td><td>25133480</td><td>G</td><td>2.83E-05</td><td></td></tr>
<tr><td>9</td><td>rs1331501</td><td>92432152</td><td>G</td><td>9.55E-05</td><td>DIRAS2 | 340515 |</td></tr>
<tr><td>11</td><td>rs1783983</td><td>57177356</td><td>A</td><td>8.95E-05</td><td>UBE2L6 | CLP1 | ZDHHC5 | TMX2 | YPEL4 | C11orf31 |</td></tr>
<tr><td>11</td><td>rs1031232</td><td>57628857</td><td>G</td><td>6.93E-05</td><td>OR9L1P | OR9I3P | OR9I2P | OR5BL1P | OR9Q1 | OR9Q2 | 643402 |</td></tr>
<tr><td>11</td><td>rs6591765</td><td>62674829</td><td>A</td><td>4.62E-05</td><td>SLC22A24 |</td></tr>
<tr><td>11</td><td>rs7949840</td><td>62741273</td><td>G</td><td>6.67E-05</td><td>SLC22A24 | SLC22A25 | SLC22A10 |</td></tr>
<tr><td>11</td><td>rs11231409</td><td>62741444</td><td>G</td><td>8.18E-05</td><td>SLC22A24 | SLC22A25 | SLC22A10 |</td></tr>
<tr><td>12</td><td>rs2098102</td><td>5026839</td><td>A</td><td>9.72E-05</td><td>KCNA5 | 390282 |</td></tr>
</table>

FIG. 6C

| | | | | | |
|---|---|---|---|---|---|
| 12 | rs906724 | 126243850 | A | 5.15E-05 | 100132564 \| |
| 13 | rs4769736 | 28876751 | G | 7.36E-05 | KIAA0774 \| |
| 13 | rs10507842 | 75481600 | G | 8.61E-05 | |
| 13 | rs7319358 | 78448935 | A | 3.34E-06 | |
| 14 | rs1956388 | 28202628 | A | 2.23E-06 | |
| 14 | rs2179891 | 28215603 | A | 6.90E-05 | FOXG1 \| C14orf23 \| |
| 14 | rs8020281 | 94436179 | A | 7.28E-05 | |
| 16 | rs1421069 | 51755435 | G | 8.00E-05 | CHD9 \| |
| 16 | rs2388011 | 51770920 | G | 9.60E-05 | CHD9 \| |
| 16 | rs3815548 | 51879235 | G | 9.94E-05 | CHD9 \| 441770 \| 100132875 \| |
| 16 | rs1424203 | 59355718 | A | 3.55E-05 | |
| 17 | rs9898519 | 24865310 | G | 3.62E-05 | TAOK1 \| TP53I13 \| ANKRD13B \| 645942 \| |
| 17 | rs3744624 | 24885455 | G | 1.48E-05 | TAOK1 \| TP53I13 \| ANKRD13B \| 645942 \| |
| 18 | rs669924 | 38725419 | A | 7.79E-05 | RIT2 \| |
| 19 | rs2116941 | 10195443 | A | 3.25E-05 | DNMT1 \| ICAM1 \| ICAM4 \| ICAM5 \| S1PR2 \| MRPL4 \| 646106 \| |
| 20 | rs755171 | 31176251 | G | 9.70E-05 | C20orf71 \| C20orf70 \| 317716 \| 391242 \| |
| 20 | rs6059101 | 31182314 | A | 3.71E-06 | C20orf71 \| C20orf70 \| 317716 \| 391242 \| |
| 20 | rs6059104 | 31185354 | A | 9.73E-05 | C20orf71 \| C20orf70 \| 317716 \| 391242 \| |
| 21 | rs2831462 | 28370367 | A | 4.17E-05 | |
| 22 | rs916234 | 46165555 | G | 5.77E-05 | |
| 22 | rs2051594 | 47259952 | A | 5.43E-05 | 643266 \| 643325 \| |

FIG. 7A (Table 4)

<table>
<tr><th>Chr*</th><th>SNP</th><th>Position*</th><th>Minor Allele</th><th>P-value</th><th>Odds Ratio</th><th>Stat</th><th>Loci**</th></tr>
<tr><td>6</td><td>rs3132679</td><td>30183822</td><td>A</td><td>9.40E-05</td><td>0.5327</td><td>-3.906</td><td>TRIM31 | RNF39 | TRIM15 | TRIM40 |</td></tr>
<tr><td>6</td><td>rs9468692</td><td>30227869</td><td>A</td><td>6.64E-04</td><td>1.767</td><td>3.404</td><td>TRIM10 | TRIM31 | RNF39 | TRIM15 | TRIM40 |</td></tr>
<tr><td>6</td><td>rs1012411</td><td>30440534</td><td>C</td><td>2.98E-04</td><td>1.526</td><td>3.617</td><td>HCG18 | 646491 | 100129192 |</td></tr>
<tr><td>6</td><td>rs2040450</td><td>30442318</td><td>A</td><td>3.54E-04</td><td>1.65</td><td>3.572</td><td>HCG18 | 646491 | 100129192 | 100129772 |</td></tr>
<tr><td>6</td><td>rs2524211</td><td>30458639</td><td>A</td><td>4.75E-04</td><td>1.612</td><td>3.495</td><td>HCG18 | 646491 | 646520 | 100129192 | 100129772 |</td></tr>
<tr><td>6</td><td>rs9261761</td><td>30480966</td><td>A</td><td>2.28E-04</td><td>0.5646</td><td>-3.685</td><td>HLA-E | MICC | HCG18 | 646520 | 100129192 | 100129772 |</td></tr>
<tr><td>6</td><td>rs9261817</td><td>30486580</td><td>C</td><td>2.33E-04</td><td>0.565</td><td>-3.68</td><td>HLA-E | MICC | HCG18 | 646520 | 100129192 | 100129772 |</td></tr>
<tr><td>6</td><td>rs9261821</td><td>30487053</td><td>G</td><td>2.46E-04</td><td>0.5663</td><td>-3.667</td><td>HLA-E | MICC | HCG18 | 646520 | 100129192 | 100129772 |</td></tr>
<tr><td>6</td><td>rs9261846</td><td>30490419</td><td>G</td><td>2.42E-04</td><td>0.5662</td><td>-3.671</td><td>HLA-E | MICC | HCG18 | 646520 | 100129192 | 100129772 |</td></tr>
<tr><td>6</td><td>rs9261847</td><td>30490626</td><td>C</td><td>4.44E-04</td><td>0.5793</td><td>-3.512</td><td>HLA-E | MICC | HCG18 | 646520 | 100129192 | 100129772 |</td></tr>
<tr><td>6</td><td>rs9261860</td><td>30492482</td><td>A</td><td>4.17E-04</td><td>0.5742</td><td>-3.529</td><td>HLA-E | MICC | HCG18 | 646520 | 100129192 | 100129772 |</td></tr>
<tr><td>6</td><td>rs9261862</td><td>30492717</td><td>G</td><td>2.17E-04</td><td>0.5636</td><td>-3.698</td><td>HLA-E | MICC | HCG18 | 646520 | 100129192 | 100129772 |</td></tr>
<tr><td>6</td><td>rs9261871</td><td>30493873</td><td>G</td><td>2.27E-04</td><td>0.5646</td><td>-3.687</td><td>HLA-E | MICC | HCG18 | 646520 | 100129192 | 100129772 |</td></tr>
<tr><td>6</td><td>rs9261919</td><td>30499702</td><td>A</td><td>2.34E-04</td><td>0.5654</td><td>-3.679</td><td>HLA-E | MICC | HCG18 | 646520 | 100129192 | 100129772 |</td></tr>
<tr><td>6</td><td>rs9261923</td><td>30500139</td><td>A</td><td>2.17E-04</td><td>0.5636</td><td>-3.698</td><td>HLA-E | MICC | HCG18 | 646520 | 100129192 | 100129772 |</td></tr>
<tr><td>6</td><td>rs9261926</td><td>30500385</td><td>A</td><td>2.47E-04</td><td>0.5665</td><td>-3.665</td><td>HLA-E | MICC | HCG18 | 646520 | 100129192 | 100129772 |</td></tr>
<tr><td>6</td><td>rs9261947</td><td>30502607</td><td>A</td><td>2.60E-04</td><td>0.5601</td><td>-3.652</td><td>HLA-E | MICC | 646520 | 100129192 | 100129772 |</td></tr>
<tr><td>6</td><td>rs9501447</td><td>30505819</td><td>G</td><td>3.36E-04</td><td>0.5737</td><td>-3.586</td><td>HLA-E | MICC | 646520 | 100129772 |</td></tr>
<tr><td>6</td><td>rs1079541</td><td>30514735</td><td>A</td><td>2.13E-04</td><td>0.5634</td><td>-3.703</td><td>HLA-E | MICC | 646520 | 100129772 |</td></tr>
<tr><td>6</td><td>rs9501467</td><td>30516949</td><td>A</td><td>4.48E-04</td><td>0.5935</td><td>-3.51</td><td>HLA-E | MICC | 646520 | 100129772 |</td></tr>
</table>

FIG. 7B

| | | | | | | | |
|---|---|---|---|---|---|---|---|
| 6 | rs9295871 | 30519068 | G | 2.91E-04 | 0.5704 | -3.623 | HLA-E \| MICC \| 646520 \| 100129772 \| |
| 6 | rs9295873 | 30522214 | G | 2.18E-04 | 0.5638 | -3.698 | HLA-E \| MICC \| 646520 \| 100129772 \| |
| 6 | rs9918306 | 30527750 | A | 2.30E-04 | 0.5732 | -3.683 | HLA-E \| MICC \| 646520 \| 100129772 \| |
| 6 | rs9295886 | 30529376 | A | 3.91E-04 | 0.5751 | -3.546 | HLA-E \| MICC \| 646520 \| 100129772 \| |
| 6 | rs35407515 | 30531202 | G | 2.13E-04 | 0.5634 | -3.703 | HLA-E \| MICC \| 646520 \| 100129772 \| |
| 6 | rs34101875 | 30531337 | A | 1.96E-04 | 0.5615 | -3.724 | HLA-E \| MICC \| 646520 \| 100129772 \| |
| 6 | rs33986393 | 30532053 | G | 2.16E-04 | 0.5637 | -3.7 | HLA-E \| MICC \| 646520 \| 100129772 \| |
| 6 | rs9501336 | 30535489 | A | 2.17E-04 | 0.5639 | -3.698 | HLA-E \| PRR3 \| MICC \| 646520 \| 100129772 \| |
| 6 | rs11966619 | 30537012 | C | 2.49E-04 | 0.5668 | -3.663 | HLA-E \| PRR3 \| MICC \| 646520 \| 100129772 \| |
| 6 | rs35792611 | 30538854 | C | 6.53E-04 | 0.5875 | -3.409 | HLA-E \| PRR3 \| MICC \| 646520 \| 100129772 \| |
| 6 | rs3132585 | 30795593 | G | 2.04E-04 | 2.972 | 3.715 | DHX16 \| MDC1 \| FLOT1 \| NRM \| KIAA1949 \| TUBB \| |
| 6 | rs3132583 | 30796554 | C | 3.00E-04 | 2.915 | 3.616 | DHX16 \| MDC1 \| FLOT1 \| NRM \| KIAA1949 \| TUBB \| |
| 6 | rs2230365 | 31633427 | A | 1.54E-04 | 1.575 | 3.785 | AIF1 \| ATP6V1G2 \| LTA \| NFKBIL1 \| TNF \| BAT2 \| BAT1 \| LST1 \| APOM \| SNORA38 \| SNORD84 \| SNORD117 \| |
| 6 | rs2229092 | 31648736 | C | 7.30E-04 | 1.882 | 3.378 | AIF1 \| ATP6V1G2 \| CSNK2B \| LTA \| LTB \| TNF \| BAT2 \| BAT1 \| LST1 \| APOM \| LY6G5B \| SNORA38 \| SNORD84 \| SNORD117 \| |
| 6 | rs537160 | 32024379 | A | 1.55E-06 | 1.943 | 4.805 | CFB \| C2 \| C4A \| C4B \| NEU1 \| SKIV2L \| RDBP \| STK19 \| EHMT2 \| SLC44A4 \| ZBTB12 \| |
| 6 | rs2072633 | 32027557 | A | 3.04E-04 | 1.513 | 3.612 | CFB \| C2 \| C4A \| C4B \| NEU1 \| SKIV2L \| RDBP \| STK19 \| EHMT2 \| SLC44A4 \| ZBTB12 \| |
| 6 | rs437179 | 32036993 | A | 3.37E-09 | 2.336 | 5.912 | CFB \| C4A \| C4B \| DOM3Z \| NEU1 \| SKIV2L \| RDBP \| STK19 \| EHMT2 \| SLC44A4 \| ZBTB12 \| |
| 6 | rs386480 | 32054816 | G | 2.52E-09 | 2.355 | 5.96 | C4A \| C4B \| DOM3Z \| SKIV2L \| RDBP \| STK19 \| EHMT2 \| ZBTB12 \| |
| 6 | rs389883 | 32055439 | C | 2.66E-09 | 2.359 | 5.951 | C4A \| C4B \| DOM3Z \| SKIV2L \| RDBP \| STK19 \| EHMT2 \| ZBTB12 \| |
| 6 | rs2856448 | 32122553 | A | 1.87E-04 | 1.515 | 3.736 | DOM3Z \| RDBP \| |
| 6 | rs185819 | 32158045 | A | 2.73E-04 | 1.498 | 3.64 | RNF5 \| PPT2 \| EGFL8 \| 653033 \| |
| 6 | rs17207986 | 32187545 | G | 1.36E-16 | 3.953 | 8.268 | ATF6B \| RNF5 \| PPT2 \| EGFL8 \| 653033 \| |
| 6 | rs1053924 | 32228693 | A | 9.32E-04 | 1.45 | 3.31 | ATF6B \| RNF5 \| PPT2 \| FKBPL \| PRRT1 \| EGFL8 \| 653033 \| 100130536 \| |
| 6 | rs2269425 | 32231617 | A | 4.85E-04 | 1.649 | 3.489 | ATF6B \| RNF5 \| PPT2 \| FKBPL \| PRRT1 \| EGFL8 \| |

FIG. 7C

| | | | | | | | |
|---|---|---|---|---|---|---|---|
| | | | | | | | 401252 \| 653033 \| 100130536 \| |
| 6 | rs2269423 | 32253685 | A | 1.68E-04 | 1.492 | 3.762 | AGER \| ATF6B \| PBX2 \| RNF5 \| AGPAT1 \| FKBPL \| PRRT1 \| EGFL8 \| 401252 \| 653033 \| 100130536 \| |
| 6 | rs443198 | 32298384 | G | 5.76E-04 | 0.689 | -3.443 | AGER \| ATF6B \| NOTCH4 \| PBX2 \| AGPAT1 \| GPSM3 \| FKBPL \| PRRT1 \| 401252 \| 100130536 \| |
| 6 | rs2894252 | 32453421 | A | 2.67E-04 | 0.6137 | -3.646 | HLA-DRA \| C6orf10 \| 646668 \| |
| 6 | rs2894253 | 32453518 | C | 1.45E-05 | 1.965 | 4.337 | HLA-DRA \| C6orf10 \| 646668 \| |
| 6 | rs9405094 | 32454386 | A | 2.66E-04 | 0.6136 | -3.647 | HLA-DRA \| C6orf10 \| 646668 \| |
| 6 | rs2395157 | 32456123 | G | 2.65E-04 | 0.6136 | -3.648 | HLA-DRA \| C6orf10 \| 646668 \| |
| 6 | rs9268454 | 32457689 | G | 2.67E-04 | 0.6137 | -3.645 | HLA-DRA \| C6orf10 \| 646668 \| |
| 6 | rs9268456 | 32457924 | A | 2.92E-04 | 0.6155 | -3.622 | HLA-DRA \| C6orf10 \| 646668 \| |
| 6 | rs9268461 | 32459879 | A | 2.66E-04 | 0.6136 | -3.647 | HLA-DRA \| C6orf10 \| 646668 \| |
| 6 | rs17423649 | 32465111 | A | 3.07E-04 | 1.695 | 3.609 | HLA-DRA \| C6orf10 \| BTNL2 \| 646668 \| |
| 6 | rs12529049 | 32465693 | A | 3.15E-04 | 1.693 | 3.603 | HLA-DRA \| C6orf10 \| BTNL2 \| 646668 \| |
| 6 | rs16870123 | 32467438 | A | 3.37E-04 | 1.687 | 3.585 | HLA-DRA \| C6orf10 \| BTNL2 \| 646668 \| |
| 6 | rs2076524 | 32478662 | G | 2.64E-04 | 0.6135 | -3.648 | HLA-DRA \| C6orf10 \| BTNL2 \| 646668 \| |
| 6 | rs2076522 | 32479157 | G | 2.64E-04 | 0.6135 | -3.648 | HLA-DRA \| C6orf10 \| BTNL2 \| 646668 \| |
| 6 | rs3806156 | 32481676 | A | 6.24E-04 | 0.6757 | -3.421 | HLA-DRA \| C6orf10 \| BTNL2 \| 646668 \| |
| 6 | rs9268491 | 32482109 | G | 2.64E-04 | 0.6135 | -3.648 | HLA-DRA \| C6orf10 \| BTNL2 \| 646668 \| |
| 6 | rs2395163 | 32495787 | G | 3.17E-04 | 0.6026 | -3.601 | HLA-DRA \| C6orf10 \| BTNL2 \| 646668 \| |
| 6 | rs34330585 | 32498681 | G | 3.00E-04 | 1.74 | 3.615 | HLA-DRA \| C6orf10 \| BTNL2 \| 646668 \| |
| 6 | rs9268905 | 32540055 | G | 5.94E-07 | 0.5461 | -4.993 | C6orf10 \| BTNL2 \| |
| 6 | rs2395185 | 32541145 | A | 1.16E-06 | 0.5558 | -4.863 | C6orf10 \| BTNL2 \| |
| 6 | rs9368726 | 32546520 | G | 7.45E-07 | 0.5503 | -4.949 | C6orf10 \| BTNL2 \| |
| 6 | rs9405108 | 32546626 | A | 5.94E-07 | 0.5462 | -4.993 | C6orf10 \| BTNL2 \| |
| 6 | rs28772724 | 32617335 | A | 1.34E-08 | 0.4848 | -5.681 | HLA-DQA1 \| |
| 6 | rs28530648 | 32635057 | C | 3.55E-05 | 1.763 | 4.135 | HLA-DQA1 \| |
| 6 | rs28366298 | 32668837 | C | 2.72E-08 | 0.4843 | -5.559 | HLA-DQA1 \| |
| 6 | rs35265698 | 32669312 | G | 6.31E-05 | 0.5203 | -4.001 | HLA-DQA1 \| |
| 6 | rs28605404 | 32677665 | G | 1.42E-06 | 1.967 | 4.822 | HLA-DQA1 \| |
| 6 | rs2516049 | 32678378 | G | 9.52E-08 | 0.503 | -5.336 | HLA-DQA1 \| |
| 6 | rs9270856 | 32678817 | A | 1.30E-06 | 1.79 | 4.84 | HLA-DQA1 \| |

FIG. 7D

| | | | | | | | |
|---|---|---|---|---|---|---|---|
| 6 | rs9271100 | 32684456 | A | 1.45E-06 | 1.784 | 4.818 | HLA-DQA1 \| |
| 6 | rs660895 | 32685358 | G | 8.98E-05 | 0.5616 | -3.917 | HLA-DQA1 \| |
| 6 | rs9271170 | 32685867 | A | 1.45E-06 | 1.784 | 4.818 | HLA-DQA1 \| |
| 6 | rs9271488 | 32696978 | A | 3.08E-08 | 0.4876 | -5.537 | HLA-DQA1 \| |
| 6 | rs9272105 | 32707977 | G | 4.38E-05 | 0.6447 | -4.086 | HLA-DQA1 \| |
| 6 | rs9272143 | 32708781 | A | 2.55E-05 | 0.6415 | -4.211 | HLA-DQA1 \| |
| 6 | rs34276369 | 32722015 | A | 6.62E-08 | 0.4968 | -5.401 | HLA-DQA1 \| HLA-DQA2 \| |
| 6 | rs2647025 | 32743927 | A | 8.19E-06 | 0.5545 | -4.46 | HLA-DQA2 \| HLA-DQB1 \| 646686 \| |
| 6 | rs2858331 | 32789255 | G | 1.25E-04 | 1.505 | 3.837 | HLA-DQA2 \| HLA-DQB1 \| 646686 \| |

METHODS OF PREDICTING MEDICALLY REFRACTIVE ULCERATIVE COLITIS (MR-UC) REQUIRING COLECTOMY

CROSS-REFERENCE TO RELATED APPLICATIONS

This application is the National Phase of International Application PCT/US09/69531, filed Dec. 24, 2009, which designated the U.S. and that International Application was published under PCT Article 21(2) in English, which claims priority under 35 U.S.C. §119(e) to U.S. provisional patent application No. 61/140,794, filed Dec. 24, 2008 and U.S. provisional patent application No. 61/182,598, filed May 29, 2009.

GOVERNMENT RIGHTS

This invention was made with government support under Grant Nos. DK046763, DK063491 and RR00425 awarded by the National Institutes of Health. The government has certain rights in the invention.

FIELD OF THE INVENTION

The invention relates generally to the fields of genetics and inflammatory disease, specifically ulcerative colitis.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Crohn's disease (CD) and ulcerative colitis (UC), the two common forms of idiopathic inflammatory bowel disease (IBD), are chronic, relapsing inflammatory disorders of the gastrointestinal tract. Each has a peak age of onset in the second to fourth decades of life and prevalences in European ancestry populations that average approximately 100-150 per 100,000 (D. K. Podolsky, N Engl J Med 347, 417 (2002); E. V. Loftus, Jr., Gastroenterology 126, 1504 (2004)). Although the precise etiology of IBD remains to be elucidated, a widely accepted hypothesis is that ubiquitous, commensal intestinal bacteria trigger an inappropriate, overactive, and ongoing mucosal immune response that mediates intestinal tissue damage in genetically susceptible individuals (D. K. Podolsky, N Engl J Med 347, 417 (2002)). Genetic factors play an important role in IBD pathogenesis, as evidenced by the increased rates of IBD in Ashkenazi Jews, familial aggregation of IBD, and increased concordance for IBD in monozygotic compared to dizygotic twin pairs (S. Vermeire, P. Rutgeerts, Genes Immun 6, 637 (2005)). Moreover, genetic analyses have linked IBD to specific genetic variants, especially CARD15 variants on chromosome 16q12 and the IBDS haplotype (spanning the organic cation transporters, SLC22A4 and SLC22A5, and other genes) on chromosome 5q31 (S. Vermeire, P. Rutgeerts, Genes Immun 6, 637 (2005); J. P. Hugot et al., Nature 411, 599 (2001); Y. Ogura et al., Nature 411, 603 (2001); J. D. Rioux et al., Nat Genet 29, 223 (2001); V. D. Peltekova et al., Nat Genet 36, 471 (2004)). CD and UC are thought to be related disorders that share some genetic susceptibility loci but differ at others.

Thus, there is a need in the art to identify genes, allelic variants and/or haplotypes that may assist in explaining the genetic risk, prognosing, diagnosing and/or predicting susceptibility for or protection against inflammatory bowel disease, and specifically, for using such genes, allelic variants and/or haplotypes to identify those at risk for medically refractive ulcerative colitis (MR-UC) requiring colectomy.

BRIEF DESCRIPTION OF THE FIGURES

Exemplary embodiments are illustrated in referenced figures. It is intended that the embodiments and figures disclosed herein are to be considered illustrative rather than restrictive.

FIG. 2B) Higher risk score categories are associated with an earlier progression to colectomy at 24 and 60 months. Risk score was divided into quarters: scores 28-38 (risk-A); scores 39-45 (risk-B); scores 46-52 (risk-C); and scores 53-60 (risk-D). At 24 months, risk of colectomy was 3.1%, 19.1% and 62% for risk-B, -C, and -D, respectively. Risk of colectomy at 60 months increased to 8.3%, 48.4%, 84% for risk-B, -C, and -D, respectively. Total number of UC subjects in each risk category is given.

FIGS. 3A-3B depict, in accordance with an embodiment herein, a table (Table 1) listing the 46 SNPs implicated in the 46 SNP risk model for MR-UC referenced herein. Also described herein as SEQ. ID. NOS.: 1-46.

FIG. 4 depicts, in accordance with an embodiment herein, sensitivity, specificity, and hazard ratio of original data and following 10-fold cross-validation and bootstrapping.

FIGS. 5A-5D depict, in accordance with an embodiment herein, a table (Table 2) listing the top 100 SNPs from Analysis I, referenced herein.

FIGS. 6A-6C depict, in accordance with an embodiment herein, a table (Table 3) listing the top 65 associated SNPs from Analysis II, referenced herein.

FIGS. 7A-7D depict, in accordance with an embodiment herein, a table (Table 4) listing MHC region associated SNPs from Analysis III, referenced herein.

SUMMARY OF THE INVENTION

Figure 1:
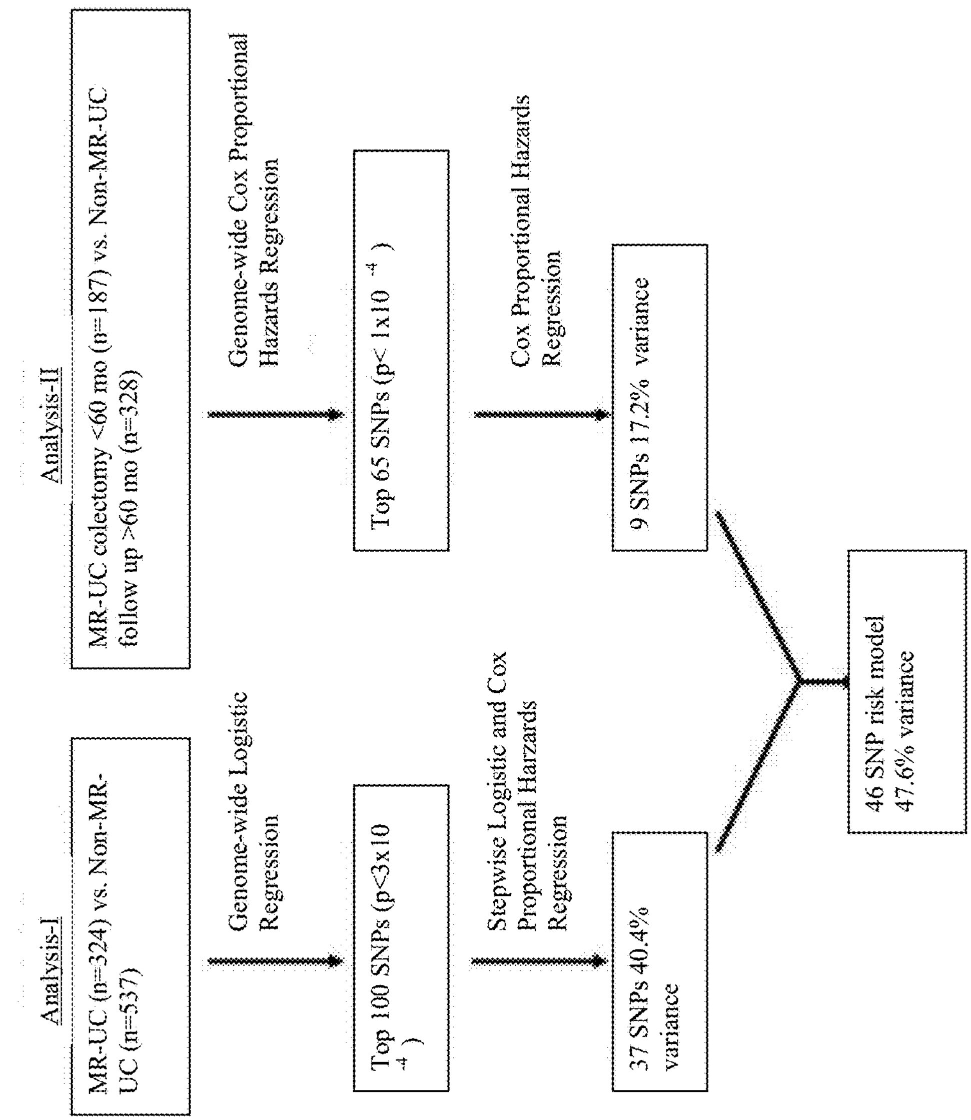
FIG. 1 depicts, in accordance with an embodiment herein, schematic describing MR-UC vs. Non-MR-UC survival analysis and risk modeling.

Various embodiments include a method of prognosing inflammatory bowel disease (IBD) in an individual, comprising obtaining a sample from the individual, assaying the sample to determine the presence or absence of one or more medically refractive ulcerative colitis (MR-UC) genetic risk variants, and prognosing an aggressive and/or severe form of IBD in the individual based on the presence of one or more MR-UC ulcerative colitis genetic risk variants. In another embodiment, the aggressive and/or severe form of IBD comprises MR-UC. In another embodiment, the individual is diagnosed with ulcerative colitis. In another embodiment, the aggressive and/or severe form of IBD comprises an earlier progression to conditions requiring colectomy. In another embodiment, the aggressive and/or severe form of IBD comprises progression to MR-UC within 10 months. In another embodiment, the aggressive and/or severe form of IBD comprises progression to MR-UC within 20 to 40 months. In another embodiment, the aggressive and/or severe form of IBD comprises progression to MR-UC within 50 to 70 months. In another embodiment, the one or more MR-UC genetic risk variants are described in FIGS. 3A-3B, FIGS. 5A-5D, FIGS. 6A-6C, and/or FIGS. 7A-7D herein. In another embodiment, the one or more MR-UC genetic risk variants comprise SEQ. ID. NOS.: 1-46.

Other embodiments include a kit for prognostic use, comprising a single prognostic panel comprising one or more medically refractive ulcerative colitis (MR-UC) genetic risk variants described in FIGS. 3A-3B, FIGS. 5A-5D, FIGS. 6A-6C, and/or FIGS. 7A-7D herein.

Other embodiments include a method of diagnosing susceptibility to medically refractive ulcerative colitis (MR-UC) in an individual, comprising obtaining a sample from the individual, assaying the sample to determine the presence or absence of one or more MR-UC genetic risk variants, and diagnosing susceptibility to MR-UC in the individual based on the presence of one or more MR-UC genetic risk variants. In another embodiment, the one or more MR-UC genetic risk variants are described in FIGS. 3A-3B, FIGS. 5A-5D, FIGS. 6A-6C, and/or FIGS. 7A-7D herein. In another embodiment, the one or more MR-UC genetic risk variants comprise SEQ. I.D. NOS.: 1-46. In another embodiment, the one or more MR-UC genetic risk variants comprise 20 to 70 MR-UC genetic risk variants.

Various embodiments include methods of treating ulcerative colitis in an individual, comprising determining the presence of one or more risk variants described in FIGS. 3A-3B, FIGS. 5A-5D, FIGS. 6A-6C, and/or FIGS. 7A-7D herein, and treating the ulcerative colitis. In another embodiment, treating the ulcerative colitis comprises colectomy.

Other embodiments include a method of diagnosing an ulcerative colitis subtype in an individual, comprising obtaining a sample from the individual, assaying the sample to determining the presence or absence of one or more medically refractive ulcerative colitis (MR-UC) genetic risk variants, and diagnosing the ulcerative colitis subtype in the individual based upon the presence of one or more MR-UC genetic risk variants. In another embodiment, the one or more MR-UC genetic risk variants are described in FIGS. 3A-3B, FIGS. 5A-5D, FIGS. 6A-6C, and/or FIGS. 7A-7D herein. In another embodiment, the ulcerative colitis subtype comprises MR-UC. In another embodiment, the one or more MR-UC genetic risk variants comprise SEQ. ID. NOS.: 1-46.

Other features and advantages of the invention will become apparent from the following detailed description, taken in conjunction with the accompanying drawings, which illustrate, by way of example, various embodiments of the invention.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ *ed*., J. Wiley & Sons (New York, N.Y. 2001); March, *Advanced Organic Chemistry Reactions, Mechanisms and Structure* 5$^{th}$ *ed*., J. Wiley & Sons (New York, N.Y. 2001); and Sambrook and Russel, Molecular Cloning: A Laboratory Manual 3$^{rd}$ *ed*., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

"IBD" as used herein is an abbreviation of inflammatory bowel disease.

"CD" as used herein is an abbreviation of Crohn's Disease.

"UC" as used herein is an abbreviation of ulcerative colitis.

"GWAS" as used herein is an abbreviation of genome wide association study.

"MR-UC" as used herein is defined as ulcerative colitis requiring colectomy for symptoms uncontrolled by medical therapy.

As used herein, the term "MR-UC genetic risk variant" refers to genetic variants, or SNPs, that have an association with the MR-UC, or ulcerative colitis requiring colectomy, phenotype.

As readily apparent to one of skill in the art, various examples of the MR-UC genetic risk variants, or single nucleotide polymorphisms, or "SNPs" referenced may be used in conjunction with embodiments described herein. For example, various versions of sequences, including the complement, may be used for genetic variants rs746503, rs2275612, rs7550055, rs7367845, rs1448901, rs4487082, rs900569, rs924022, rs9843732, rs2286461, rs12650313, rs1399403, rs7675371, rs3846599, rs6596684, rs1536242, rs17207986, rs777649, rs11764116, rs4722456, rs929351, rs2980654, rs6994721, rs4734754, rs7861972, rs3118292, rs10817934, rs2403456, rs1461898, rs6591765, rs887357, rs526058, rs7319358, rs1956388, rs11156667, rs10133064, rs8020281, rs965353, rs305087, rs759258, rs2967682, rs2293683, rs6034134, rs10485594, rs6059104 and rs2831462, described herein as SEQ. ID. NOS. 1-46, respectively, and in FIGS. 3A-3B herein, and the invention is not in any way limited to only these specific sequences when referring to the referenced MR-UC genetic risk variant.

As used herein, the term "biological sample" means any biological material from which nucleic acid molecules can be prepared. As non-limiting examples, the term material encompasses whole blood, plasma, saliva, cheek swab, or other bodily fluid or tissue that contains nucleic acid.

Acute severe ulcerative colitis (UC) remains a significant clinical challenge and the ability to predict, at an early stage, those individuals at risk of colectomy for medically refractory UC (MR-UC) would be a major clinical advance. As disclosed herein, the inventors used a genome-wide association study (GWAS) in a well characterized cohort of UC patients to identify genetic variation that contributes to MR-UC. A GWAS comparing 324 MR-UC patients with 537 Non-MR-UC patients was analyzed using logistic regression and Cox proportional hazards methods. In addition, the MR-UC patients were compared with 2601 healthy controls.

As further disclosed herein, MR-UC was associated with more extensive disease ($p=2.7\times10^{-6}$) and a positive family history of UC ($p=0.004$). A risk score based on the combination of 46 SNPs associated with MR-UC explained 48% of the variance for colectomy risk in the cohort. Risk scores divided into quarters showed the risk of colectomy to be 0%, 17%, 74% and 100% in the four groups. Comparison of the MR-UC subjects with healthy controls confirmed the contribution of the major histocompatibility complex to severe UC (peak association: rs17207986, p=1.4×10−16) and provided genome-wide suggestive association at the TNFSF15 (TL1A) locus (peak association: rs11554257, p=1.4×10−6). A SNP-based risk scoring system, identified herein by GWAS analyses, can provide a useful adjunct to clinical parameters for predicting natural history in UC. Furthermore, discovery of genetic processes underlying disease severity can help to identify pathways for novel therapeutic intervention in severe UC.

In one embodiment, the present invention provides a method of diagnosing ulcerative colitis in an individual by determining the presence or absence of a MR-UC risk variant, where the presence of the MR-UC genetic risk variant is indicative of ulcerative colitis in the individual. In another embodiment, the MR-UC genetic risk variant is described in FIGS. 3A-3B, FIGS. 5A-5D, FIGS. 6A-6C, and/or FIGS. 7A-7D herein.

In another embodiment, the present invention provides a method of diagnosing susceptibility to an ulcerative colitis subtype in an individual by determining the presence or absence of a MR-UC genetic risk variant, where the presence of the MR-UC genetic risk variant is indicative of susceptibility to the ulcerative colitis subtype in the individual. In another embodiment, the ulcerative colitis subtype is medically refractive ulcerative colitis (MR-UC) requiring colectomy.

In another embodiment, the present invention provides a method of prognosing ulcerative colitis in an individual by determining the presence or absence of one or more MR-UC genetic risk variants, where the presence of one or more MR-UC genetic risk variants is indicative of a severe and/or aggressive form of ulcerative colitis. In another embodiment, the ulcerative colitis is MR-UC. In another embodiment, the one or more MR-UC genetic risk variants are described in FIGS. 3A-3B, FIGS. 5A-5D, FIGS. 6A-6C, and/or FIGS. 7A-7D herein. In another embodiment, the one or more MR-UC genetic risk variants have an additive effect, where the presence of each additional MR-UC genetic risk variant is indicative of greater risk of a severe and/or aggressive form of ulcerative colitis for the individual. In another embodiment, the presence of each additional MR-UC genetic risk variant is indicative of an earlier progression to colectomy for the individual.

In another embodiment, the present invention provides a method of treating ulcerative colitis in an individual by determining the presence of one or more MR-UC genetic risk variants and treating the ulcerative colitis. In another embodiment, the MR-UC genetic risk variant is described in FIGS. 3A-3B, FIGS. 5A-5D, FIGS. 6A-6C, and/or FIGS. 7A-7D herein.

A variety of methods can be used to determine the presence or absence of a variant allele or haplotype. As an example, enzymatic amplification of nucleic acid from an individual may be used to obtain nucleic acid for subsequent analysis. The presence or absence of a variant allele or haplotype may also be determined directly from the individual's nucleic acid without enzymatic amplification.

Analysis of the nucleic acid from an individual, whether amplified or not, may be performed using any of various techniques. Useful techniques include, without limitation, polymerase chain reaction based analysis, sequence analysis and electrophoretic analysis. As used herein, the term "nucleic acid" means a polynucleotide such as a single or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule.

The presence or absence of a variant allele or haplotype may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

A TaqmanB allelic discrimination assay available from Applied Biosystems may be useful for determining the presence or absence of a variant allele. In a TaqmanB allelic discrimination assay, a specific, fluorescent, dye-labeled probe for each allele is constructed. The probes contain different fluorescent reporter dyes such as FAM and VICTM to differentiate the amplification of each allele. In addition, each probe has a quencher dye at one end which quenches fluorescence by fluorescence resonant energy transfer (FRET). During PCR, each probe anneals specifically to complementary sequences in the nucleic acid from the individual. The 5' nuclease activity of Taq polymerase is used to cleave only probe that hybridize to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Improved specificity in allelic discrimination assays can be achieved by conjugating a DNA minor grove binder (MOB) group to a DNA probe as described, for example, in Kutyavin et al., "3'-minor groove binder-DNA probes increase sequence specificity at PCR extension temperature, "Nucleic Acids Research 28: 655-661 (2000)). Minor grove binders include, but are not limited to, compounds such as dihydrocyclopyrroloindole tripeptide (DPI,).

Sequence analysis also may also be useful for determining the presence or absence of a variant allele or haplotype.

Restriction fragment length polymorphism (RFLP) analysis may also be useful for determining the presence or absence of a particular allele (Jarcho et al. in Dracopoli et al., Current Protocols in Human Genetics pages 2.7.1-2.7.5, John Wiley & Sons, New York; Innis et al., (Ed.), PCR Protocols, San Diego: Academic Press, Inc. (1990)). As used herein, restriction fragment length polymorphism analysis is any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Allele-specific oligonucleotide hybridization may also be used to detect a disease-predisposing allele. Allele-specific oligonucleotide hybridization is based on the use of a labeled oligonucleotide probe having a sequence perfectly complementary, for example, to the sequence encompassing a disease-predisposing allele. Under appropriate conditions, the allele-specific probe hybridizes to a nucleic acid containing the disease-predisposing allele but does not hybridize to the one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a disease-predisposing allele by using an allele-specific oligonucleotide primer that is perfectly complementary to the nucleotide sequence of the disease-predisposing allele but which has one or more mismatches as compared to other alleles (Mullis et al., supra, (1994)). One skilled in the art understands that the one or more nucleotide mismatches that distinguish between the disease-predisposing allele and one or more other alleles are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the disease-associated and other alleles at the 3' end of the primer.

A heteroduplex mobility assay (HMA) is another well known assay that may be used to detect a SNP or a haplotype. HMA is useful for detecting the presence of a polymorphic sequence since a DNA duplex carrying a mismatch has reduced mobility in a polyacrylamide gel compared to the mobility of a perfectly base-paired duplex (Delwart et al., Science 262: 1257-1261 (1993); White et al., Genomics 12: 301-306 (1992)).

The technique of single strand conformational, polymorphism (SSCP) also may be used to detect the presence or absence of a SNP and/or a haplotype (see Hayashi, K., Methods Applic. 1: 34-38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also may be used to detect a SNP and/or a haplotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for determining the presence or absence of a SNP and/or a haplotype are known in the art and useful in the methods of the invention. Other well-known approaches for determining the presence or absence of a SNP and/or a haplotype include automated sequencing and RNAase mismatch techniques (Winter et al., Proc. Natl. Acad. Sci. 82: 7575-7579 (1985)). Furthermore, one skilled in the art understands that, where the presence or absence of multiple alleles or haplotype(s) is to be determined, individual alleles can be detected by any combination of molecular methods. See, in general, Birren et al. (Eds.) Genome Analysis: A Laboratory Manual Volume 1 (Analyzing DNA) New York, Cold Spring Harbor Laboratory Press (1997). In addition, one skilled in the art understands that multiple alleles can be detected in individual reactions or in a single reaction (a "multiplex" assay). In view of the above, one skilled in the art realizes that the methods of the present invention may be practiced using one or any combination of the well known assays described above or another art-recognized genetic assay.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Overall

Acute severe ulcerative colitis (UC) remains a significant clinical challenge and the ability to predict, at an early stage, those individuals at risk of colectomy for medically refractory UC (MR-UC) would be a major clinical advance. As disclosed herein, the inventors used a genome-wide association study (GWAS) in a well characterized cohort of UC patients to identify genetic variation that contributes to MR-UC. A GWAS comparing 324 MR-UC patients with 537 Non-MR-UC patients was analyzed using logistic regression and Cox proportional hazards methods. In addition, the MR-UC patients were compared with 2601 healthy controls.

As further disclosed herein, MR-UC was associated with more extensive disease ($p=2.7\times10-6$) and a positive family history of UC ($p=0.004$). A risk score based on the combination of 46 SNPs associated with MR-UC explained 48% of the variance for colectomy risk in the cohort. Risk scores divided into quarters showed the risk of colectomy to be 0%, 17%, 74% and 100% in the four groups. Comparison of the MR-UC subjects with healthy controls confirmed the contribution of the major histocompatibility complex to severe UC (peak association: rs17207986, $p=1.4\times10-16$) and provided genome-wide suggestive association at the TNFSF15 (TL1A) locus (peak association: rsl 1554257, $p=1.4\times10-6$). A SNP-based risk scoring system, identified herein by GWAS analyses, can provide a useful adjunct to clinical parameters for predicting natural history in UC. Furthermore, discovery of genetic processes underlying disease severity can identify pathways for novel therapeutic intervention in severe UC.

Example 2

UC Cases

Ulcerative Colitis (UC) subjects (n=929) were recruited at Cedars Sinai-Medical Center Inflammatory Bowel Disease Center following informed consent after approval by the Institutional Review Board. UC diagnosis was based on standard criteria 31. UC subjects requiring colectomy for severe disease refractory to medical therapies (including intravenous corticosteroids, cyclosporine, and biologic therapies) were classified as medically refractory UC (MR-UC). Subjects requiring colectomy where the indication was for treatment of cancer/dysplasia, in addition to subjects not requiring colectomy, were classified as Non-MR-UC. Subjects who required colectomy for MR-UC and were subsequently found to have evidence of dysplasia or carcinoma in the resected colon were classified as MR-UC (n=3). For the MR-UC cohort, time from diagnosis to date of colectomy was collected; time from diagnosis to last follow-up visit was obtained for the Non-MR-UC cohort. Samples which did not genotype successfully (n=16), exhibited gender mismatch (n=9) or cryptic relatedness (n=13), or were considered outliers by principal components analysis (n=30) were excluded. Following these measures, 861 UC subjects (MR-UC n=324; Non-MR-UC n=537) were included in the analyses.

Example 3

Non-IBD Controls

Controls were obtained from the Cardiovascular Health Study (CHS), a population-based cohort study of risk factors for cardiovascular disease and stroke in adults 65 years of age or older, recruited at four field centers. 5,201 predominantly Caucasian individuals were recruited in 1989-1990 from random samples of Medicare eligibility lists, followed by an additional 687 African-Americans recruited in 1992-1993 (total n=5,888). CHS was approved by the institutional Review Board at each recruitment site, and subjects provided informed consent for the use of their genetic information. A total of 2,601 Caucasian non-IBD control subjects who underwent GWAS were included in these analyses. African-American CHS participants were excluded from analysis due to insufficient number of ethnically-matched cases.

Example 4

Genotyping

All genotyping was performed at the Medical Genetics Institute at Cedars-Sinai Medical Center using Infinium technology (Illumina, San Diego, Calif.). UC cases were genotyped with either the HumanCNV370-Quad or Human610-Quad platform; controls were genotyped with the HumanCNV370-Duo platform. Identity-by-descent was used to exclude related individuals (Pi-hat scores >0.5; PLINK). Average genotyping rate among cases and controls retained in the analysis was >99.8% and >99.2%, respectively. Single nucleotide polymorphisms (SNPs) were excluded based on: test of Hardy-Weinberg Equilibrium p<10-3; SNP failure rate>10%; MAF<3%; SNPs not found in dbSNP Build 129. 313,720 SNPs passed quality control measures and were common in all data sets.

Example 5

Population Stratification

Principal components analysis (Eigenstrat as implemented in Helix Tree) (Golden Helix, Bozeman, Mont.) was conducted to examine population stratification. Extreme outliers, defined as subjects more than two standard deviations (SD) away from the distribution of the rest of the samples for any component, were removed. All African-American participants identified by principal components analysis were excluded from these analyses. Genetic heterogeneity following correction for population sub-structure was low, with estimated genomic inflation factors ($\lambda GC$) of 1.04 and 1.06 for MR-UC vs. Non-MR-UC, and MR-UC cases vs. Non-IBD controls analyses, respectively.

Example 6

MR-UC vs. Non-MR-UC: Survival Analysis and Risk Modeling

Single marker association analysis of MR-UC vs. Non-MR-UC (analysis-1) was performed using a logistic regression model correcting for population stratification using 20 principal components as covariates (PLINK v1.06). Association between medically refractory disease (MR-UC) and the top 100 SNPs together (as determined by the lowest corrected p-values) from analysis-1 were tested using a stepwise logistic regression model. SNPs were further analyzed by Cox proportional hazards regression utilizing time-to information, as described for UC cases (using the step and glm, and coxph functions, respectively, in R v2.9.0). 37 SNPs identified with logistic regression p<0.05 and Cox proportional hazards p<0.1 were retained in the risk model. The 100 SNPs ($p<3\times10-4$) evaluated from analysis-1 are listed herein. A genome-wide Cox proportional hazards regression analysis (analysis-11) was then performed on a subset of the UC cohort (MR-UC subjects with colectomy <60 months, n=187; Non-MR-UC followed up >60 months, n=328) correcting for population stratification using two principal components as covariates (PLINK). The top 65 SNPs (8 of which overlap with the 100 SNPs from analysis-1 above) were tested together (using coxph function in R). The 65 SNPs ($p<1\times10-4$) from analysis-11 are listed herein. From these 65 SNPs, 9 SNPs were identified ($p<3\times10-4$) and combined with the 37 SNPs from analysis-1 to identify a final risk model consisting of 46 SNPs (see FIG. 1 for schematic). A genetic risk score was calculated from the total number of risk alleles (0, 1, or 2) across all 46 risk SNPs (theoretical range: 0-92). Risk score (observed range: 28-60) was divided into quarters: scores 28-38 (risk-A); scores 39-45 (risk-B); scores 46-52 (risk-C); and scores 53-60 (risk-D). Receiver operating characteristic (ROC) curve and area under the ROC curve (AUC) were calculated using R software v2.9.0, including packages survival and survivalROC 39-41. Sensitivity and specificity curves, positive and negative predictive values, positive (sensitivity/(1-specificity) and negative likelihood ratio (1-sensitivity/specificity) were all calculated using the R package ROCR 42. 1000-fold replication of 10-fold cross-validation was implemented to validate the fitted logistic regression model. Mean sensitivity and specificity were then re-calculated using the 1000 replicated samples. Bootstrap method with 1000-fold replication was utilized for estimating variability of hazard ratio estimated from the Cox regression model. The hazard ratio in survival analysis is the effect of an explanatory variable on the hazard or risk of an event.

Example 7

MR-UC vs. Non-IBD Controls: Regression Analysis

Single marker analysis of genome-wide data for MR-UC cases vs. Non-IBD Caucasian controls from CHS (analysis- III) was performed as before, using logistic regression correcting for 20 principal components (PLINK).

Example 8

UC Subject Demographics

Complete temporal data was available on 861 UC subjects (MR-UC n=324; Non-MRUC n=537). The demographic data of the cohort is summarized herein. The inventors observed no differences in gender, median age of onset of disease, and smoking status between the medically refractory and Non-MR-UC subjects. There was a significant difference in our median disease duration ($p=7.4\times10-9$), with the time from diagnosis to last follow-up in the Non-MR-UC cohort nearly double the time from diagnosis to colectomy in our MR-UC subjects. Additionally, there was a significantly higher incidence of disease that extended proximal to the splenic flexure ($p=2.7\times10-6$) in the MR-UC group when compared to Non-MR-UC, consistent with previously published data. The inventors identified a novel association between a family history (first or second degree relative) of UC and the development of MR-UC (p=0.004).

Example 9

Forty-Six SNP Risk Model is Associated with AIR-UC and Predicts Earlier Progression to Colectomy The inventors performed a GWAS on 324 MR-UC and 537 Non-MR-UC subjects. Results of this analysis (analysis-I) are given herein and discussed below. Following identification of single markers associated with MR-UC, the inventors proceeded to a multivariate approach. Beginning with the top 100 results from analysis-1 ($p<3\times10-4$), the inventors performed a stepwise logistic regression and identified 64 SNPs ($p<0.05$) that together were associated with medically refractory disease (MR-UC) and were carried forward to survival analysis. Of these 64 SNPs, 37 SNPs remained (Cox proportional hazards regression $p<0.1$; OR 1.2-1.8), which explained 40% of the variance for MR-UC. In order to elucidate the maximum discrimination, i.e. greatest percentage of the variance, the inventors further performed a genome-wide Cox proportional hazards regression analysis (analysis-11) on a subset of the UC cohort to identify SNPs involved in earlier progression to colectomy. Testing together the top 65 SNPs from this analysis ($p<1\times10-4$), the inventors identified nine SNPs with Cox proportional hazards $p<3\times10-4$ (individual OR ranged from 1.4-1.6), explaining 17% of the variance. Beginning with the previously identified 37 risk SNP model, these 9 SNPs were added sequentially to the model. This analysis resulted in the final risk model of 46 SNPs (OR for MR-UC for each individual SNP ranged from 1.2-1.9), which explained 48% of the variance for colectomy in the MR-UC cohort.

The inventors calculated a genetic risk score from the total number of risk alleles across all 46 risk SNPs (theoretical range: 0-92). The observed risk score ranged from 28-60, and was significantly associated with MR-UC (logistic regression and Cox proportional hazards pvalues <10-16). An ROC curve using this risk score gave an AUC of 0.91. The sensitivity of the fitted model for MR-UC was 0.793, with a specificity of 0.858. Using 1000 replicates of the 10-fold cross-validation data, they obtained a mean sensitivity of 0.789 (SD=0.0067) and mean specificity of 0.859 (SD=0.002; Table 3). This indicates that the fitted model was robust and only ~0.4% over-fitting was observed. The hazard ratio was estimated to be 1.313 from the Cox regression model. 1000 replicates of bootstrapped samples gave an estimated hazard ratio of 1.314 (SD=0.017).

Figure 2A:
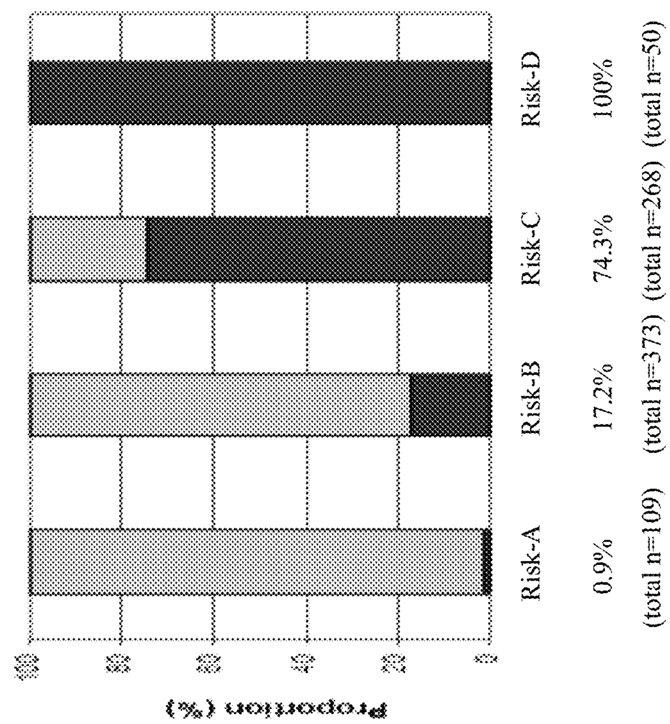
FIGS. 2A-2B depict, in accordance with an embodiment herein, FIG. 2A) Higher risk score categories are associated with MR-UC ($\chi 2$ test for trend $p<2.2\times10-16$). Risk score (observed range: 28-60) was divided into quarters: scores 28-38 (risk-A); scores 39-45 (risk-B); scores 46-52 (risk-C); and scores 53-60 (risk-D). Percentage of MR-UC is noted, along with the total number of UC subjects in each risk category.
Figure 2B:
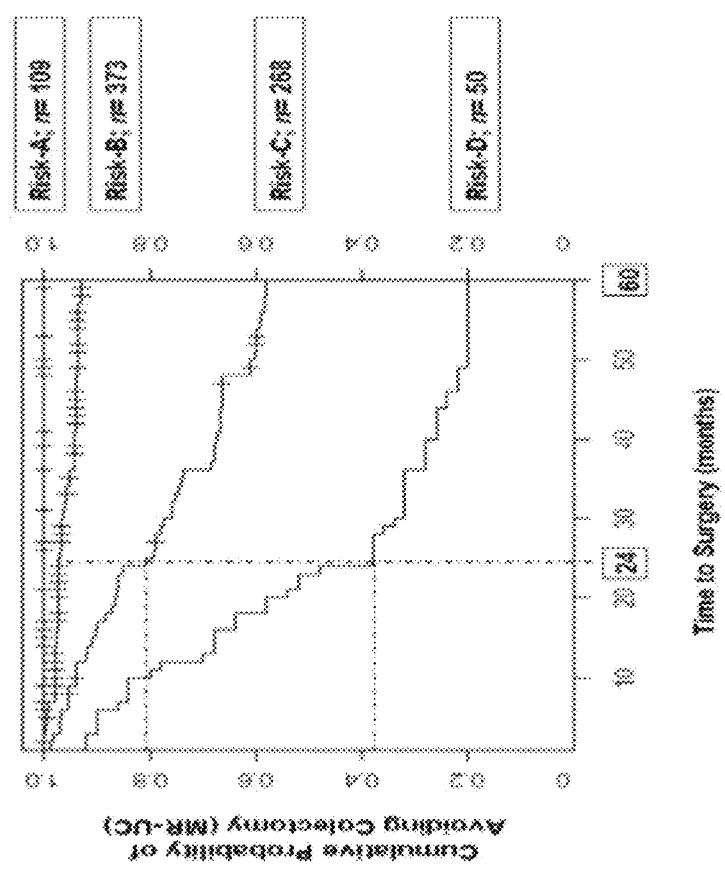

Based on the genetic risk scores, the inventors grouped the UC cohort into four risk categories; less than 1% of cases in the lowest risk category (risk-A) were MR-UC and the percentage of MR-UC increased to ~17%, ~74% and 100% in risk-B, -C and -D groups, respectively ($\chi2$ test for trend $p<2.2\times10-16$). The median time to colectomy for risk-C and -D categories was 72 months and 23 months, respectively. Progression to colectomy within 2 and 5 years of diagnosis may be more clinically relevant and while no individuals in the risk-A category had undergone colectomy at either 2 or 5 years after diagnosis, the respective incidence of MR-UC at 2 years for risk groups-B, -C and -D was 3.1%, 19.1%, and 62%, respectively, and at 5 years was 8.3%, 50%, and 80%, respectively (FIG. 2B). At five years from diagnosis, either the total risk score (AUC 0.86) or the risk category (AUC 0.82) are able to predict patients that will require surgery. The operating characteristics of the risk score system are shown herein. A score of 44 and 47 can be used to generate a test with a sensitivity (to exclude a diagnosis of colectomy) and specificity (to include a diagnosis) of over 90%, respectively. Loci corresponding to the 46 SNPs in the risk model include several compelling candidate genes for UC severity and suggest potential biological pathways for further avenues of study. As each risk SNP contributes modestly to the overall risk of MR-UC (OR 1.2-1.9), this work supports the paradigm that a group of SNPs, identified by GWAS and combined together may account for a large proportion of the genetic contribution to a complex phenotype (48% of the variance for risk in this study) to provide a risk score with clinical utility.

Example 10

MHC Region and TL1A (TNFSF15) Contribute to UC Severity

Association analyses between 324 UC subjects with MR-UC and 2,601 population matched controls confirmed a major contribution of the major histocompatibility (MHC) on chromosome 6p to the development of severe UC (analysis-III). Ten SNPs in MHC reached a priori defined level of genome-wide significance ($p\leq5\times10-7$; 87 SNPs with $p<1\times10-3$), with peak association at rs17207986 ($p=1.4\times10-16$). Three SNPs on chromosome 9q, a locus which contains the known IBD susceptibility gene TNFSF15 (TL1A), achieved genome-wide suggestive significance ($p<5\times10-5$), with the most significant association seen at rs11554257 ($p=1.4\times10-6$).

Example 10

Discussion

Utilizing a GWAS approach of a well-characterized UC cohort and a large healthy control group, the inventors confirmed the contribution of the MHC to severe UC at a genome-wide level of significance and observed more than one 'signal' from this locus. The inventors also implicated TNFSF15 (TL1A) in UC severity, with potential therapeutic implications. It was confirmed an association between extensive disease and colectomy, and also demonstrated, for the first time, that a family history of UC is associated with the need for surgery. These observations support the concept that genetic variation contributes to the natural history of UC. The regression model of 46 SNPs presented herein discriminates patients at risk of MR-UC and explains approximately 50% of the genetic contribution to the risk of surgery in the cohort. When the risk score was divided into four categories, higher risk score categories had a higher percentage of MR-UC subjects ($p<2.2\times10^{-16}$) and predicted earlier colectomy.

The predictive power of diagnostic tests can be evaluated by the area under the curve (AUC), an ROC summary index, which evaluates the probability that one's test correctly identifies a diseased subject from a pair of affected and unaffected individuals. A perfect test has an AUC of 1.0, while random chance gives an AUC of 0.5. Screening programs attempting to identify high-risk groups generally have an AUC of ~0.80 48. The genetic risk score reported herein yielded an AUC of 0.91.

The inventors calculated operating characteristics in an attempt to determine whether a prognostic test based on these genetic data would be clinically useful. The score of 44 and 47 (out of a possible score of 60) can be used to generate a test with a sensitivity and specificity of over 90%, respectively. The fitted model was robust, given the comparable mean sensitivity and specificity following cross-validation. In addition, likelihood ratios can be used with differing pre-test probabilities to calculate relevant post-test probabilities and are therefore much more generalizable. The Cochrane collaboration has suggested that positive likelihood ratios of greater than 10 and negative likelihood ratios of less than 0.1 are likely to make a significant impact on health care. As can be seen from the data presented herein, these ratios are met with a risk score of 47 and 43, respectively. For example, in a newly diagnosed patient with ulcerative colitis, if the pre-test probability of colectomy was approximately 20% (based on epidemiological and clinical data) and the patient had a genetic risk score of 47 (positive likelihood ratio of approximately 10), then utilizing Bayesian principles, this equates to a post-test probability of colectomy of approximately 75%. If patients at high risk for colectomy could be identified early in their course of disease, then this could have significant consequences for clinicians. Clinicians may suggest earlier introduction of more potent medication for the high risk patients and choose to clinically and endoscopically monitor these patients more intensively. Stressing the mportance of compliance with therapy and even monitoring compliance in high-risk patients may also be considered by clinicians.

The inventors have confirmed the association with the MHC and disease severity in UC and the data shows that there may be more than one 'signal' from this locus. Furthermore, the inventors have also implicated a realistic therapeutic target and known IBD locus, TNFSF15 (TL1A), suggesting that interference with this pathway is important in severe UC. In addition, the inventors have demonstrated the utility of a model based on GWAS data for predicting the need for surgery in UC. These data demonstrate that the effect of these variants cumulatively they may provide adequate discriminatory power for clinical use. These findings allow a more tailored approach to the management of UC patients and also identify additional targets for early therapeutic intervention in more aggressive UC.

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations,"

without other modifiers, typically means at least two recitations, or two or more recitations).

Accordingly, the invention is not limited except as by the appended claims.

REFERENCES

1. Franke A, Balschun T, Karlsen T H, et al. Replication of signals from recent studies of Crohn's disease identifies previously unknown disease loci for ulcerative colitis. Nat Genet 2008; 40:713-5.
2. Fisher S A, Tremelling M, Anderson C A, et al. Genetic determinants of ulcerative colitis include the ECM1 locus and five loci implicated in Crohn's disease. Nat Genet 2008; 40:710-2.
3. Franke A, Balschun T, Karlsen T H, et al. Sequence variants in IL10, ARPC2 and multiple other loci contribute to ulcerative colitis susceptibility. Nat Genet 2008; 40:1319-23.
4. Silverberg M S, Cho J H, Rioux J D, et al. Ulcerative colitis-risk loci on chromosomes 1p36 and 12q15 found by genome-wide association study. Nat Genet 2009; 41:216-20.
5. Anderson C A, Massey D C, Barrett J C, et al. Investigation of Crohn's disease risk loci in ulcerative colitis further defines their molecular relationship, Gastroenterology 2009; 136:523-9.
6. Barrett J C, Lee J C, Lees C W, et al. Genome-wide association study of ulcerative colitis identifies three new susceptibility loci, including the HNF4A region. Nat Genet 2009; 41:1330-4.
7. Imielinski M, Baldassano R N, Griffiths A, et al. Common variants at five new loci associated with early-onset inflammatory bowel disease, Nat Genet 2009; 41:1335-40.
8. Asano K, Matsushita T, Umeno J, et al. A genome-wide association study identifies three new susceptibility loci for ulcerative colitis in the Japanese population. Nat Genet 2009; 41:1325-9.
9, Barrett J C, Hansoul S, Nicolae D L, et al. Genome-wide association defines more than 30 distinct susceptibility loci for Crohn's disease. Nat Genet 2008; 40:955-62.
10. Farmer R G, Easley K A, Rankin G B. Clinical patterns, natural history, and progression of ulcerative colitis. A long-term follow-up of 1116 patients. Dig Dis Sci 1993; 38:1137-46.
11. Henriksen M, Jahnsen J, Lygren I, et al. Ulcerative colitis and clinical course: results of a 5-year population-based follow-up study (the IBSEN study). Inflamm Bowel Dis 2006; 12:543-50.
12. Hendriksen C, Kreiner S, Binder V. Long term prognosis in ulcerative colitis—based on results from a regional patient group from the county of Copenhagen. Gut 1985; 26:158-63.
13. Fraga X F, Vergara M, Medina C, et al. Effects of smoking on the presentation and clinical course of inflammatory bowel disease. Eur J Gastroenterol Hepatol 1997; 9:683-7.
14. Mokbel M, Carbonnel F, Beaugerie L, et al. [Effect of smoking on the long-term course of ulcerative colitis]. Gastroenterol Clin Biol 1998; 22:858-62.
15. Basu D, Lopez I, Kulkarni A, et al. Impact of race and ethnicity on inflammatory bowel disease. Am J Gastroenterol 2005; 100:2254-61.
16. Nguyen G C, Torres E A, Regueiro M, et al. Inflammatory bowel disease characteristics among African Americans, Hispanics, and non-Hispanic Whites: characterization of a large North American cohort. Am J Gastroenterol 2006; 101:1012-23.
17. Roussomoustakaki M, Satsangi J, Welsh K, et al. Genetic markers may predict disease behavior in patients with ulcerative colitis. Gastroenterology 1997; 112:1845-53.
18. Bouma G, Crusius J B, Garcia-Gonzalez M A, et al. Genetic markers in clinically well defined patients with ulcerative colitis (UC). Clin Exp Immunol 1999; 115:294-300.
19. de la Concha E G, Fernandez-Arquero M, Lopez-Nava G, et al. Susceptibility to severe ulcerative colitis is associated with polymorphism in the central MHC gene 1KBL. Gastroenterology 2000; 119:1491-5.
20. Yamamoto-Furusho J K, Uscanga L F, Vargas-Alarcon G, et al. Clinical and genetic heterogeneity in Mexican patients with ulcerative colitis. Hum Immunol 2003; 64:119-23.
21. Ahmad T, Armuzzi A, Neville M, et al. The contribution of human leucocyte antigen complex genes to disease phenotype in ulcerative colitis. Tissue Antigens 2003; 62:527-35.
22. Fernandez L, Nunez C, Mendoza J L, et al. A recombined haplotype in the major histocompatibility region contains a cluster of genes conferring high susceptibility to ulcerative colitis in the Spanish population. Inflamm Bowel Dis 2005; 1.1:785-91.
23. Brant S R, Panhuysen C I, Nicolae D, et al. MDR1 Ala893 polymorphism is associated with inflammatory bowel disease. Am J Hum Genet 2003; 73:1282-92.
24. Ho G T, Gaya D R, Satsangi J. Multidrug resistance (MDR1) gene in inflammatory bowel disease: a key player? Inflamm Bowel Dis 2005; 11:1013-9.
25. Ho G T, Soranzo N, Nimmo E R, et al. ABCB1/MDR1 gene determines susceptibility and phenotype in ulcerative colitis: discrimination of critical variants using a gene-wide haplotype tagging approach. Hum Mol Genet 2006; 15:797-805.
26. Weedon M N, McCarthy M I, Hitman G, et al. Combining information from common type 2 diabetes risk polymorphisms improves disease prediction. PLoS Med 2006; 3: e374.
27. Lu Q, Elston R C. Using the optimal receiver operating characteristic curve to design a predictive genetic test, exemplified with type 2 diabetes. Am J Hum Genet 2008; 82:641-51.
28. Evans D M, Visscher P M, Wray N R. Harnessing the information contained within Genome-wide Association Studies to improve individual prediction of complex disease risk. Hum Mol Genet 2009; doi: 10.1093/hmg/ddp295
29. Henckaerts L, Van Steen K, Verstreken I, et al. Genetic risk profiling and prediction of disease course in Crohn's disease patients. Clin Gastroenterol 1-lepatol 2009; 7:972-980 e2.
30. Dubinsky M, Ling M, Friedman M, et al. Genome Wide Association (GWA) Predictors Of Anti-Tnfα Therapeutic Responsiveness In Pediatric Inflammatory Bowel Disease (IBD). AGA DDW #76, Chicago, Ill., 2009.
31. Lennard-Jones J E, Ritchie J K, Zohrab W J. Proctocolitis and Crohn's disease of the colon: a comparison of the clinical course. Gut 1976; 17:477-82.
32. Fried L P, Borhani N O, Enright P, et al. The Cardiovascular Health Study: design and rationale. Ann Epidemiol 1991; 1:263-76.
33. Psaty B M, O'Donnell C J, Gudnason V, et al. Cohorts for Heart and Aging Research in Genomic Epidemiology (CHARGE) Consortium: Design of Prospective Meta-Analyses of Genome-Wide Association Studies From 5 Cohorts. Circ Cardiovasc Genet 2009; 2:73-80.
34. Gunderson K L, Steemers F J, Ren H, et al. Whole-genome genotyping. Methods Enzymol 2006; 410:359-76.

35. Gunderson K L, Steemers F J, Lee G, et al. A genome-wide scalable SNP genotyping assay using microarray technology. Nat Genet 2005; 37:549-54.

36. Purcell S, Neale B, Todd-Brown K, et al. PLINK: a tool set for whole-genome association and population-based linkage analyses. Am J Hum Genet 2007; 81:559-75.

37. Price A L, Patterson N J, Plenge R M, et al. Principal components analysis corrects for stratification in genome-wide association studies. Nat Genet 2006; 38:904-9.

38. Devlin B, Roeder K. Genomic control for association studies. Biometrics 1999; 55:997-1004.

39. RDC T. R: A language and environment for statistical computing. In: Computing RFfS, ed. 2.9.0 ed. Vienna, Austria, 2006.

40. Heagerty P J, Lumley T, Pepe M S. Time-dependent ROC curves for censored survival data and a diagnostic marker. Biometrics 2000; 56:337-44.

41. Lasko T A, Bhagwat J G, Zou K H, et al. The use of receiver operating characteristic curves in biomedical informatics. J Biomed Inform 2005; 38:404-15.

42. Sing T, Sander O, Beerenwinkel N, et al. ROCR: visualizing classifier performance in R. Bioinformatics 2005; 21:3940-1.

43. Efron B. Bootstrap Methods: Another look at the jackknife. The Annals of Statistics 1979; 7:1-26.

44. Zhu H, Rohwer R. No free lunch for cross-validation. Neural Computation 1996; 8:1421-1426.

45. Solberg I C, Lygren I, Jahnsen J, et al. Clinical course during the first 10 years of ulcerative colitis: results from a population-based inception cohort (IBSEN Study). Scand J Gastroenterol 2009; 44:431-40.

46. Takedatsu H, Michelsen K S, Wei B, et al. TL1A (TNFSF15) regulates the development of chronic colitis by modulating both T-helper 1 and T-helper 17 activation. Gastroenterology 2008; 135:552-67.

47. Hanley J A, McNeil B J. The meaning and use of the area under a receiver operating characteristic (ROC) curve. Radiology 1982; 143:29-36.

48. Wilson P W, D'Agostino R B, Levy D, et al. Prediction of coronary heart disease using risk factor categories. Circulation 1998; 97:1837-47.

49. McGovern D P B, Summerskill W S M, McManus R, et al. Evidence-Based Medicine in General Practice. BIOS Scientific Publishers Ltd, 2001.

50. Matanis T, Akhmanova A, Wulff P, et al. Bicaudal-D regulates COPI-independent Golgi-ER transport by recruiting the dynein-dynactin motor complex. Nat Cell Biol 2002; 4:986-92.

51. Moorhead A R, Rzomp K A, Scidmore M A. The Rab6 effector Bicaudal DI associates with Chlamydia trachomatis inclusions in a biovar-specific manner. Infect Immun 2007; 75:781-91.

52. Ide N, Hata Y, Nishioka H, et al. Localization of membrane-associated guanylate kinase (MAGI)-I/BAI-associated protein (BAP) 1 at tight junctions of epithelial cells. Oncogene 1999; 18:7810-5.

53. van Bodegraven A A, Curley C R, Hunt K A, et al. Genetic variation in myosin IXB is associated with ulcerative colitis. Gastroenterology 2006; 131:1768-74.

54. McGovern D P, Taylor K D, Landers C, et al. MAGI2 genetic variation and inflammatory bowel disease. Inflamm Bowel Dis 2009; 15:75-83.

55. Wapenaar M C, Monsuur A J, van Bodegraven A A, et al. Associations with tight junction genes PARD3 and MAGI2 in Dutch patients point to a common barrier defect for coeliac disease and ulcerative colitis. Gut 2008; 57:463-7.

56. Jetten A M. Retinoid-related orphan receptors (RORs): critical roles in development, immunity, circadian rhythm, and cellular metabolism. Nucl Recept Signal 2009; 7: e003.

57. Yang X O, Pappu B P, Nurieva R, et al. T helper 17 lineage differentiation is programmed by orphan nuclear receptors ROR alpha and ROR gamma. Immunity 2008; 28:29-39.

58. Ogawa K, Tanaka K, Ishii A, et al. A novel serum protein that is selectively produced by cytotoxic lymphocytes. J Immunol 2001; 166:6404-12.

59. Kuepper M, Bratke K, Julius P, et al. Increase in killer-specific secretory protein of 37 kDa in bronchoalveolar lavage fluid of allergen-challenged patients with atopic asthma. Clin Exp Allergy 2005; 35:643-9.

60. Yang H, Rotter J I, Toyoda H, et al. Ulcerative colitis: a genetically heterogeneous disorder defined by genetic (HLA class 11) and subclinical (antineutrophil cytoplasmic antibodies) markers. J Clin Invest 1993; 92:1080-4.

61. Stokkers P C, Reitsma P H, Tytgat G N, et al. HLA-DR and -DQ phenotypes in inflammatory bowel disease: a meta-analysis. Gut 1999; 45:395-401.

62. Yamazaki K, McGovern D, Ragoussis J, et al. Single nucleotide polymorphisms in TNFSF15 confer susceptibility to Crohn's disease. Hum Mol Genet 2005; 14:3499-506.

63. Picornell Y, Mei L, Taylor K, et al. TNFSFI5 is an ethnic-specific IBD gene. Inflamm Bowel Dis 2007:13: 1333-8.

64. Tremelling M, Berzuini C, Massey D, et al. Contribution of TNFSF15 gene variants to Crohn's disease susceptibility confirmed in UK population. Inflamm Bowel Dis 2008; 14:733-7.

65. Thiebaut R. Kotti S, Jung C. et al. TNFSFI5 polymorphisms are associated with susceptibility to inflammatory bowel disease in a new European cohort. Am J Gastroenterol 2009; 104:384-91.

66. Bamias G, Martin C, 3rd, Marini M, et al. Expression, localization, and functional activity of TL1A, a novel ThI-polarizing cytokine in inflammatory bowel disease. J Immunol 2003; 171:4868-74.

67. Prehn J L, Mehdizadeh S, Landers C J, et al. Potential role for TL1A, the new TNF-family member and potent costimulator of IFN-gamma, in mucosal inflammation. Clin Immunol 2004; 112:66-77.

68. Zini N, Lisignoli G, Solimando L, et al. IL1-beta and TNF-alpha induce changes in the nuclear polyphosphoinositide signalling system in osteoblasts similar to that occurring in patients with rheumatoid arthritis: an immunochemical and immunocytochemical study. Histochem Cell Biol 2003; 120:243-50.

69. McGraw D W, Almoosa K F, Paul R J, et al. Antithetic regulation by betaadrenergic receptors of Gq receptor signaling via phospholipase C underlies the airway beta-agonist paradox. J Clin Invest 2003; 112:619-26.

70. Shi G P, Bryant R A, Riese R, et al. Role for cathepsin F in invariant chain processing and major histocompatibility complex class II peptide loading by macrophages. J Exp Med 2000; 191:1177-86.

71. Barrett J C, Fry B, Maller J, et al. Haploview: analysis and visualization of LD and haplotype maps. Bioinformatics 2005; 21:263-5.

The invention claimed is:

1. A method of treating ulcerative colitis (UC) in a human subject, comprising:

obtaining a sample from the human subject with UC;

contacting the sample with an oligonucleotide probe specific to an “A” allele at nucleotide 465 of SEQ ID NO:1, an oligonucleotide probe specific to an “A” allele at nucleotide 301 of SEQ ID NO:2, an oligonucleotide probe specific to a “C” allele at nucleotide 301 of SEQ ID NO:3, an oligonucleotide probe specific to an “A” allele at nucleotide 3412 of SEQ ID NO:4, an oligonucleotide probe specific to a variant allele at any one of nucleotides 4505-4604 of SEQ ID NO:4, an oligonucleotide probe specific to a “G” allele at nucleotide 364 of SEQ ID NO:5, an oligonucleotide probe specific to an “A” allele at nucleotide 251 of SEQ ID NO:6, an oligonucleotide probe specific to a “G” allele at nucleotide 239 of SEQ ID NO:7, an oligonucleotide probe specific to an “A” allele at nucleotide 250 of SEQ ID NO:8, an oligonucleotide probe specific to a “G” allele at nucleotide 501 of SEQ ID NO:9, an oligonucleotide probe specific to a “G” allele at nucleotide 301 of SEQ ID NO:10, an oligonucleotide probe specific to an “A” allele at nucleotide 501 of SEQ ID NO:11, an oligonucleotide probe specific to an “A” allele at nucleotide 501 of SEQ ID NO:12, an oligonucleotide probe specific to a “G” allele at nucleotide 201 of SEQ ID NO:13, an oligonucleotide probe specific to an “A” allele at nucleotide 244 of SEQ ID NO:14, an oligonucleotide probe specific to a “G” allele at nucleotide 501 of SEQ ID NO:15, an oligonucleotide probe specific to a “G” allele at nucleotide 195 of SEQ ID NO:16, an oligonucleotide probe specific to a “G” allele at nucleotide 101 of SEQ ID NO:17, an oligonucleotide probe specific to an “A” allele at nucleotide 582 of SEQ ID NO:18, an oligonucleotide probe specific to an “A” allele at nucleotide 301 of SEQ ID NO:19, an oligonucleotide probe specific to a “G” allele at nucleotide 324 of SEQ ID NO:20, an oligonucleotide probe specific to an “A” allele at nucleotide 301 of SEQ ID NO:21, an oligonucleotide probe specific to a “G” allele at nucleotide 1394 of SEQ ID NO:22, an oligonucleotide probe specific to an “A” allele at nucleotide 251 of SEQ ID NO:23, an oligonucleotide probe specific to an “A” allele at nucleotide 201 of SEQ ID NO:24, an oligonucleotide probe specific to an “A” allele at nucleotide 301 of SEQ ID NO:25, an oligonucleotide probe specific to a “G” allele at nucleotide 301 of SEQ ID NO:26, an oligonucleotide probe specific to a “G” allele at nucleotide 1124 of SEQ ID NO:27, an oligonucleotide probe specific to an “A” allele at nucleotide 501 of SEQ ID NO:28, an oligonucleotide probe specific to a “G” allele at nucleotide 2000 of SEQ ID NO:29, an oligonucleotide probe specific to a “G” allele at nucleotide 351 of SEQ ID NO:30, an oligonucleotide probe specific to an “A” allele at nucleotide 301 of SEQ ID NO:31, an oligonucleotide probe specific to a “G” allele at nucleotide 380 of SEQ ID NO:32, an oligonucleotide probe specific to an “A” allele at nucleotide 201 of SEQ ID NO:33, an oligonucleotide probe specific to a “G” allele at nucleotide 1158 of SEQ ID NO:34, an oligonucleotide probe specific to a “G” allele at nucleotide 371 of SEQ ID NO:35, an oligonucleotide probe specific to a “C” allele at nucleotide 201 of SEQ ID NO:36, an oligonucleotide probe specific to an “A” allele at nucleotide 501 of SEQ ID NO:37, an oligonucleotide probe specific to a “G” allele at nucleotide 50 of SEQ ID NO:38, an oligonucleotide probe specific to an “A” allele at nucleotide 201 of SEQ ID NO:39, an oligonucleotide probe specific to an “A” allele at nucleotide 501 of SEQ ID NO:40, an oligonucleotide probe specific to a “C” allele at nucleotide 201 of SEQ ID NO:41, an oligonucleotide probe specific to a “G” allele at nucleotide 401 of SEQ ID NO:42, an oligonucleotide probe specific to a “C” allele at nucleotide 401 of SEQ ID NO:43, an oligonucleotide probe specific to an “A” allele at nucleotide 101 of SEQ ID NO:44, an oligonucleotide probe specific to a “G” allele at nucleotide 307 of SEQ ID NO:45, and an oligonucleotide probe specific to an "A" allele at nucleotide 251 of SEQ ID NO:46, to form allele-specific hybridization complex(es) between the oligonucleotide probes and target alleles in the sample;

assessing the binding between the oligonucleotide probes and the target alleles thereof, by detecting the allele-specific hybridization complexes;

prognosing the human subject with UC with an earlier progression to colectomy based on the allele-specific hybridization complex(es) detected; and treating the human subject with UC prognosed with an earlier progression to colectomy by performing a surgical procedure comprising colectomy.

2. The method of claim 1, wherein UC comprises MR-UC.

3. The method of claim 1, wherein the subject treated has a higher incidence of MR-UC.

4. The method of claim 1, wherein colectomy is performed within about 10 months from UC prognosis.

5. The method of claim 1, wherein colectomy is performed within 10 to 40 months from UC prognosis.

6. The method of claim 1, wherein colectomy is performed within 40 to 72 months from UC prognosis.

* * * * *

SEQUENCE LISTING

<160> NUMBER OF SEQ ID NOS: 46

<210> SEQ ID NO 1
<211> LENGTH: 844
<212> TYPE: DNA
<213> ORGANISM: Homo sapiens

<400> SEQUENCE: 1

```
ctggcagagc ttaggtctcc tgtaagcgcg tgcctgctgg ctgccccgat ccctgcagtg     60

atcactgcag aagaacagag agggaggaag tgcctggtca gacagcagca gacctgagtg    120

gttgagaaca ggaagggggg caggcaggag agaagaatct aggggttctc gactccaggc    180

cctgcagggg tgggtacgtt tccataactg gactggtttc ttgatctcac ccaattcttt    240

gaagagatct ttttttgaca taagtggtgt gggagagttc ttgttgcttg ccattagcca    300

cctctggctc agatgagaaa ggaaaattgg gtgggtgggg tcagctacct gactgatctc    360

cgaggacagc acccagttgt ccttggccac aagcatcttc aaggaggaga cgttattgta    420

gctcaggtac acctgaaaga gtacacaggt gctaccacta ccccrccccc ttccttcagg    480

gcccctgagc caaggccaag ggtgtgccag agaggaacct gggccaggaa tgggttgggc    540

ggtgggtggg tggtgcggca ggtgctgtgg aaagagtcct gggcgttgag aagggaggtc    600

caggcttggg cttggctaga cccactgtgt gaacctagac aagctactct gcctctccag    660

gtctccgctt cacctaccaa acagggacgc aggccagctc tttgctaatg gtagcaatca    720

tgaggcgtgt cattatatcc tgctctcccc gggcttcttc aaacccgttc tgacaagcag    780

ggaaggttgg ggcccggtgg gtctgaagac tgtctttcga gcagagagcc ttacctggtg    840

ctag                                                                 844
```

<210> SEQ ID NO 2
<211> LENGTH: 601
<212> TYPE: DNA
<213> ORGANISM: Homo sapiens

<400> SEQUENCE: 2

```
cccagtacta tagtacttct atctattctt aggagaggct taatattttg catggtgaga     60

attaatcata ttgaataagt aattgaataa gcaacaccac attacttacc tgcagaccaa    120

ttacactttg gccagctttt aattttcctt catcaaaacg tcttgtttgt ttttctgcat    180

acttaactcc aatgtcaatg gttgtatgga atccttttgt tttagcctag acagaaacat    240

gcacactaac tgaaaaggcc aacagagttt cacagaagga acaacaaaga aatgatatgt    300

ycatagacaa aggggcccaa actagagata aaaagtattt aaggctgttc aataatatac    360

tgcatcattt gaaatgtgag tgttctaagt aagctatcta gtacgatgca gctgatgtca    420

gcagcctttc cacaaagcta ctaattacag aagagacagg ccccgcccca cctggtctga    480

acccccatga aaaagcaatg atgcaattca tcaccaatgt ggtgggaatc tgttaaccag    540

ccattaaaga catgtacgta ccagacctgc tagagccacc agagtagtct gaacctgggt    600

c                                                                    601
```

<210> SEQ ID NO 3
<211> LENGTH: 601
<212> TYPE: DNA
<213> ORGANISM: Homo sapiens

<400> SEQUENCE: 3

```
tcaggatacc tccatagagt cccaaaatga gcacaaagtt gcaaccagtg gccacaccaa     60
```

```
tcactgtgcc atgggcccta gcatgccagc ttgtgtccac acatgccaac cgcattagtg    120

gtgccaagtc acaaaagtaa tgggccacct ctttcaagca gaagggcaga gtggcagtga    180

gggtggctgg cacaagtgca gctgagaagc cagccaccca actggcccca gctagtcgta    240

actgtacctg tctgctcatg agtgcgtggt agtggagtgg gtggcagatg ataaggtagc    300

katccagtgc catgacaccc agcaggtagc actcagtcat ccctaaggaa tgaaagacat    360

agctgaataa agcatacagc tgatgagacg ggtgaacacc cttggagcaa ggtgtgcagc    420

agcatgggca ctgtggtgct gacataccac acctctacaa aggagaggac actgataaat    480

aagtacatgg gcgtgaacag tccagaatct aactgtacca ggacaatgat gagaatgttc    540

cctgcaagtg tgaggagata gatgcatagg gtccccaaga aggcaagagg ttgtagggtc    600

c                                                                    601


<210> SEQ ID NO 4
<211> LENGTH: 9326
<212> TYPE: DNA
<213> ORGANISM: Homo sapiens
<220> FEATURE:
<221> NAME/KEY: misc_feature
<222> LOCATION: (4505)..(4604)
<223> OTHER INFORMATION: n is a, c, g, or t

<400> SEQUENCE: 4

taacttttat ttttacctct taagtatctt aaaataatag tggaagtagt attttaacta     60

ggctttacat atagattata aattttaaat taagtactaa aatcaaatac atagactttc    120

agtttacagt ctgggatata agaagctggg aaggtgctac tccatcctaa caccaggtaa    180

aaagctgaca tacttaaaaa aatcaatgac acttggccag gcgcggtggc tcacgcctgt    240

aatcccagca ctttgggagg acgagacggg cggatcacga ggtcaggaga tcgagaccat    300

cctggctaac acggtgaaac cccatctcta ctaaaaatac aaaaaattag ccgggcgtag    360

tggagggtga ctgtagtccc agctactcgg gaggctgagg cagaagaatg gcgtgaaccc    420

ggaaggcgga gcttgcagtg agctgagatc gtgccactac actcttgcct gggcgacaga    480

gcgagactct gtctcaaaaa aaaaaaaaaa aaaaaaagtc aacgacactt cttagatctc    540

taagaaaatt gagggccaag gcaaactgtt cacaaaattg gaaagaatga aaggcaagta    600

tgtagaatca caatttactg gagcagaaac ccatgagcaa aaacctctag gaaccagtgc    660

ttgggtaggg aaaactgaac tgtaatatat gtggtaggtg cattaagcat ttactctacg    720

ggacccagtt aggaggcttt tttgaaaagc atactttgtg agttttactt ccaggggctt    780

aatctggttc ttagtgaata ctgcagaaat actccctctt gcttcctgca aggggaagga    840

aaactaacga ttttgaatta agatggagca ttctgttctt agcaaggcct gccctcagga    900

aaaactattt aaccagaagc taacatgcta gggttttatc agaggcttac tgacctgggg    960

gaagagaaaa acccaacccc agcccactct agccaccccg taccacataa gaggaggaaa   1020

aactgaggtg catttgtgaa gttcatagtc cagaggctca ggctgacaca gttcctttta   1080

catagtacat catgtttggc aattaagaaa aaattacaag gtacgccagg aggcaaaaaa   1140

aaacatagtt tgaagagaca aagcaagcat aaaaaccagc cttagatatg gcagggatgt   1200

tgaaatttga aagaactatg agtaataagc taaggcctct aatggataaa atagcatgca   1260

agaacagatg ggcaatgcaa gcaaagagat gaaaatttct cgagcttgag gatatattat   1320

ttatttttct tttttttctt ccacaacagt tatctcagaa gaggatatat taataggaac   1380
```

```
ttccaaaact aaaaaacaaa gagaacaaag actgaaaaaa tcagcacaga atgtccaagg   1440
attgtgggac aactacaaaa ggtataactt atgcattaat ggaaatacaa ggagaggaaa   1500
gagagaaaaa aaggaagaac tatctgaaat ataatgaatg agaatttccc caatttaatg   1560
tcaaatacca aagcaaagat ctaagaatct cagagaatac caagcagaag aaacaccaca   1620
aaaacctcta gatttacaca tatcatattc aaactacaga aaatccaaga taaagaaaaa   1680
ttctggtcca gctatggtgg ctcacacctc taatcccagc actttgggag gctaaggcgg   1740
gcagactgct tgagcctagc agctcgagac cagcctggac aacatggcaa aaccccatct   1800
ctacatacta aaaaaaagga aaaaaaaatc ctgaaagaaa acactttacc gatagaggag   1860
caaagataag aacttcatct gacttcttct tagaaaccag gcaagcaaga ggagactgga   1920
gtgaaatatc ttgcgttgag aaaaaaaatc tggcaatcta aacctctgca ccctatgaaa   1980
ttatcattca aaagtaaaac aggactgggc atcatagctc acgcctgtaa tctcagcact   2040
ttggaaggcc aagagggagg actgcttaag cccaggagtt gtgcagcagc ctgagaaaca   2100
ccgccagacc ttatctctac aataataaat aaaataaata tatatatata tatatttttt   2160
tgagacagag tctcgctctg tcacccaggc tggagtgcag tggtgcgatc ttggctcact   2220
gcaagctccg cctcctgggt tcacaacagt ctcctgcctc agcctcccga gtagctggga   2280
ctacaggcgc ccaccaccat gcccagctaa tttttgtat ttttagtaga gacagggttt   2340
caccatgtta gtcaggatgg tctggatctc ctgacctcgt gatctgccca cctggcctcc   2400
caaagtgctg ggattacagg catgagccac cgcacccggc caataaaata aaattttttt   2460
taagtgaaag aaaaatactt tctcagagaa aaaaacttga gaaaatctgt cgccagtagg   2520
actgccttgt aagaaatgat ttttttcttt ttttctgaga cggaatcttg ctctgttgcc   2580
caggctggag tgcaatggag cgattttggc tccctgcagc ctccacctcc caggtccaag   2640
cgattctcgt gcctcagcct cccaagtagc tgggactata aatgccacca ggcccggcta   2700
atttttgtat ttttagtaga gacggggttt caccatgttg gccaggctgg tctcgaactc   2760
ctgacctcaa gtgatctacc cacctcagcc tcccaaagtg ctaggatcac aggcgtgagc   2820
caccacacct ggccagaaat gttaaatgat gttctttaaa gaaaaagaaa attttatatg   2880
tcagaaactc agatataaat aaaggaaatg tatcaaagaa agaatacgtt gaaggtaaaa   2940
tacaaacttt tattttcctt attcctaatt gttccaacag ataacagttt gttcaaaata   3000
ataacagcaa cagcatattt gattatatat gattatgtgt atatatgctt atgcatgctt   3060
aggtataaat aaaataatga gagcaatgat acaaaggaaa ggagggatga attaggatta   3120
ttttgttatt atcaggtact agcactaccc atgaagctgt acagtgttat ttgaaagtgg   3180
atatggatta gttgtaaaag tatataatgt aaactctagg gcaaccatta aagaaagcta   3240
aaagaaaaaa aagtataacc tatatgctaa gaaagcagag aaaaatggaa ttatataaag   3300
taaaccataa aacacaaaaa aagagtggaa tataaaaata gaaataaaga atatgagcaa   3360
caaatagaac atagtaataa acacggtaga tatttattac tatatgataa tmcaactaca   3420
tcaacaacca ctttgaaatc tactttaaac ataaagacac agatagatta aaagtaaatg   3480
gatgaaggcc aggtgtggtg gctcatgcct ataatcccag tactttggga ggccgaggtg   3540
ggtcccatcg cttgagccaa ggagttcaag accagcctgg ggtacactga caccccatgt   3600
ctatacaaaa aatacaaaaa ttagcaggtg tggtgtcttg tgcctgtagt cccagctact   3660
tgggaggctg aggtgggagg attgcttaag tccaggaggt tgaggctgta gtgagccacc   3720
gcactccagc ctaggctaca gagggagacc ctgttctcaa aaacaaacaa acaaacaaac   3780
```

-continued

```
aaacaaacaa acaaacaaaa cagggctagt ctcagtggct gacacttgta attccagcac   3840
tttgggaggc tgaggcaggc agatttcttg tggtcaggag ttccagacca gcctggccaa   3900
catggtgaaa acctgtctct actaaaaata ctaatattag ccagatgtgg tggaggacgc   3960
atgtaatcct agctacttgg gaggctgagg catgagaatc atttgaaccc aggaggcaga   4020
ggctgcctgg gtgacagagc aagactttgt ctcaaaaaaa aaaaaaaaaa gtaaatggat   4080
aaagaatatg ccatgctaac actaatcaaa agaaagcagg agcagttata tcaatttcag   4140
acaaagctga ctccagagca agaaaaggtg tcaggaataa aaaggggcat tatggctggg   4200
tgtggtggct cacacctgta atcccagcac tttgggaggc tgatgcgagc ggatcacaag   4260
gtcaggagat cgagactgtc ctggctaaca cggtgaaacc ccgtctctac taaaaataca   4320
aaaaaattag ccgggcatgg tggcgggcac ctgtagtccc agctactcag gagactgagg   4380
caggagaatg gcatgaacct gggatgtgga gcttgcagtg agccgagatc acgccactgc   4440
actccagcca agggtgacag agcaagactc tgtctcaaca aaaaaaaaaa aaaaaaaaaa   4500
aaaannnnnn nnnnnnnnnn nnnnnnnnnn nnnnnnnnnn nnnnnnnnnn nnnnnnnnnn   4560
nnnnnnnnnn nnnnnnnnnn nnnnnnnnnn nnnnnnnnnn nnnnataatg agaaaggggt   4620
caatgttcca agaagacata ataatttttt tttttttttt gagacagagt cttgctctgt   4680
cacccaggcc agagggcagt gttgcaatgt cagctcacgc ctcctgggtt caagcaattc   4740
tcctgtctca gcctcccaag tagctgggat tacaggtgtc tgccaccaca cctagctaat   4800
tttgtatttt tagtagagac ggggtttcac cacattggcc aggctggtct cgaattcctg   4860
acctcaagtg atctgcccgc ctaagcttcc caaagggctg ggattacagg ggtgagccac   4920
cacacccggc caacaatact taatatttat atgcctaata acagaacatc aaaacatgag   4980
gcaaaatgat taactattga caaatagatc aatccaccat tatagttgga gattttgata   5040
cccctctatc agaaatgaac agattcaatg ggcagaaaat cagcaaggac ataaactcaa   5100
caataccatc aattaactgg atataattgg tatctataga ctacttcatc caacaaccat   5160
agaatatact ttctactcaa ggtcgtgcgg aaaattcatg aagagctcat tctgggccac   5220
aaaacatacc ttaacaaaat taaaacaata gaaatcatac aatgtatgct cttacaccac   5280
aatgaacttc tactagaaat caataacaaa gaaagctgta aaatccgaag atatgtctaa   5340
ataatacgag tcaaaaaagc aatctaaaag aagaaatgaa aaaatattct gaactagata   5400
aaaataaaaa gacaacttgt caaaatttgt gtgatgcagc caaagcagtg cttagtggga   5460
aacttgtagt atcgaatgca tatattagta aagaagactt aaaatcagta atttaagctt   5520
ccaccttagg aaactaaaaa aaaaaaatag gaaattaaat acaaagtaat cagaataata   5580
taaactagag cagaaatcaa taaaattgaa aacagaaaat agaaaaaaat caacaaaacc   5640
aaaagctggt tgtttaaaaa gatcaatgat actgataagc ctctagctag gctaagaaaa   5700
aagagagagg acacaaatta ttaatttcag aaatgaaaaa ggggcatcac tacagatcct   5760
atggacttta aaaagataaa ctccttgaaa tttctaaatt tgcacaagaa aaaaatggaa   5820
ggctctgaat aggcttatat ctactaaata aattgagtca ataattaacc ttccaaaaca   5880
gatagcacca ggcccagatg ggttcactaa ggaattctac taaacatttg aggaagaaat   5940
tatacccaac ctctgttatg ttttagagga tagaagcaga ggaaatactt cctaactctt   6000
ctccaaggtt agcattacct taataccaaa atctgacaaa gacacagtga aagaaaacta   6060
taagccaggc acaatggaat gtactcatag tcctagctac tgggaggctg aagtgggagg   6120
```

-continued

```
atcacttgaa cccaggagtc tgcgcctagc ctgggcaaca tagatcccct gtccaaacat   6180
gaaaagaaaa aaactataga tcagtatctt tcataaacac agatgcaaaa atcctcaata   6240
aaatattagc aaattgaatc caatgatgta taaaagaatt taagatcacg gccaaatgag   6300
ttttttttt ttttttttt ttttttttt ttttgagaca gtgtcttgct ctgtcaccca   6360
ggccggagtg cagtggcacg aactcggctc actgcaagct ccgcctccca ggttcacgcc   6420
agtctcctgt ctcagcctcc cgagtaactg ggactacagg cactggccac cacgcctggc   6480
taattttttt gtatttttag tagagacggg gtttcaccat gttagccagg atggtctcga   6540
tctcctgacc tcgtgatctg cctgcctcgg cctcccaaag tgctgggatt acaggcgtga   6600
gccaccgcac ccggccccaa gtgagattta cctgaagtat gcaaggctga ttcaatgttt   6660
gaaaattaat taatataatc catcacatca gtaggctaaa gaagaaaaat atgatcagat   6720
tgatagaggc aaagtatttg acaaaattca acactcattc atgataaaaa ctctcagtaa   6780
gctaggaata gacaacgtcc tcaacctgat aaaaaaaaaa aaaatctaca aaaaaacctc   6840
atgtctaata tcatacttaa tggtgagaaa ctagaagttt tcccactaag atcaggaaga   6900
aggcaacaat gtcctctctt atcactcttt tcaacatcat actggaagtc ctagctaatg   6960
caataagata agaaagagaa attaaaggta gaattgggaa ggaaaaaaac aactatctgt   7020
tttaggcggg tgacatgact gtctacgtag acaatctgaa agaaatgaga aaaaaaaaaa   7080
atccctggaa ctaataagtg actacagcaa agttgcagga tacaaagtta acatacaaaa   7140
gtcaattgct ttgtcaaaca ataaacaatt atgatgtgaa attaaaaaca cagtatcatt   7200
taccttaaca ccccccaaaa tgaaatactt aagtataaat ccaacaaata tgtacaagac   7260
ctatgtgagc aaaactctga tgaaagaaat caaagaacta aataaataag agatatttca   7320
tgttcatgga taagaagaca caacactgtc aagataccag ttcttctcaa cttgatctat   7380
aaattcaatt caatacaagt caaaatccca gcgagttgtt ttatggatat tgacaaaatg   7440
attctaaagt ctatattgaa aggcaaaaga cctactatag ccaacacaat attgaagtag   7500
aagaacaaag ttgaaggact gacactattc aacttcaaaa catactataa acctacagta   7560
atcaagacag tgtggtagtg gcaaagaata aaataaaata gatcaatgga acagaataga   7620
gagcccagaa ataaatccac atagtcaatt atcttcaaca aatgggcaaa ggcagttgcg   7680
caacaaatgg gcaacagtgg agaaaagtca agtcttcaac aaatggtgct gcaacaactg   7740
gacatccaca aacaaacaac aaaaaaatga atctagacaa aaaccttaca cctttcacaa   7800
agggaatcac aaacatagat gtaaaatcca aaactataaa actcctagaa agtaacacag   7860
gaaaaaaaat ctagatgact ttggttttgt gacaaccaac tttagatatg acatcaaggg   7920
catgatccat gtaagaatga aatgatgagc tgaacttcat taaaattaaa aacttctgtt   7980
tggttaaaga cattgtaaag agaatgaaaa gacaagccac agactgggag aaaatatttg   8040
taaaatatac atccgataag gaactgcttt ccaaaatata caaagaactc ttaaaaccca   8100
acaataagaa aacaaacaat tggattaaaa aatgagccaa agaccttaac agacacctca   8160
ccaaagaaga tatacagatg gcagataagc atatgaaaag atggtcaatg aggaaatgta   8220
tatgtcatca gggaaatgca aatttaaata ataagatacc acaacaaacc tattagaatg   8280
gccaaaatcc agaacactga caacaccaaa tgctaacgag gatgtggagc aacaggaaat   8340
cccattcact gctgctggga atgcaaaatg gtacagccac tttagaacac agcttgtcag   8400
tttcttatat aactaagcat actcttacca tatgaaccag caattacact ccttggtatt   8460
tacccaaagg agctgaaaac ttacggccac acaaaaacct gcacacagat gtttatggca   8520
```

```
cctttattca taattgccaa aatttgaaag caaccaagat gtctttcagt ttgtcaatga   8580

gtaaataaac tgtggtacat cccgacaatg taatattact caatgctaaa aagaaatgag   8640

ctatcaagcc acgaatagac atgaaagaaa cttaaatgta tactagtaag tgaaagaaac   8700

caatataaaa aggctatata ctgtatgact tcaaatatat gacagtctgc aaaagataaa   8760

actatggaaa cagtaaaaag atcagtgatt tccaggggct caggggaaga gataaaaagg   8820

tgaaacacag aagattttta gggcagcaaa actactctat atgatacata atggtggata   8880

catgatatta tacatttgtc aaaactctta aaatgttcca catctttaaa tacattaatg   8940

tgaactatgg tctttaggtg aaatgatgtg ttaatgaaag ttcactgact gtaacaaatg   9000

taccatctgc tgggagataa tagggggaga ctacacatgt gtggggtcag gaagtatatg   9060

ggaaatatct gtatcttctt ctcaattttg ctatgaacct aaaattggtc taaaaaaata   9120

aagtgtattg aattaaaaat caaatataac aaggatcgat aaaaatatca catagtgata   9180

tttagacata gtgtagtagt acttagcttc tggctccctt tgcttattga tctctctcaa   9240

actctctcac acacacaaca cctgttcaaa tataacatat tagctttgtt tttacttcta   9300

ctatttaaaa gaaaaaatta aaaaca                                        9326
```

<210> SEQ ID NO 5
<211> LENGTH: 537
<212> TYPE: DNA
<213> ORGANISM: Homo sapiens

<400> SEQUENCE: 5

```
atcagtctca aatctaaacc aattttggag gtgaggggtg gtccatcttg cacctataaa     60

agtctcatta ctggtggtgt taacttttct tggtcaagac agtgtctgcc aggcttctac    120

aactagaaag tcatgttttt cccctttttgt aatcaataga tattttctgg agagataatt   180

tgagactatg taaaatttca tttaaaccct actttcaccc accagtttgg gtgtccatta    240

atgttaatta ttactgtgat agttgtcaaa tggagacctt ctgatatcat caatccttct    300

acatttatta gttggctttc tactgtaagg gagacttctc ttgccttccc atttgtttat    360

tcayttattc atttatttct tttagcagtg tggagccaca tatttgtgtt ttattcagta    420

gattagaatc tgtaactgtc attatttatc ttgatgctca aatcaccaga tgtggccaat    480

gaaagcctct ttaaactggc ttctgagaat ttttgttatc tcctcattat tgtttga       537
```

<210> SEQ ID NO 6
<211> LENGTH: 501
<212> TYPE: DNA
<213> ORGANISM: Homo sapiens

<400> SEQUENCE: 6

```
atatactaga acaaaaggaa tgaatcaggg ctctcacaag caaatgagaa tataagatca     60

tccaacctct gaacaccaag aaattataat tgtaacacaa tcatgtataa cgtcagtggt    120

gaattccctt tctgctccct atattacaag ttgtttccct ctctctccca ttcatcctat    180

ctctctactc aacttcacct ttattctggc agacaaagta cacacgcatg gattgctatg    240

tagaccattc rcaagtaaga atgaaaacca ctacatctgg taaagaccca tctggccacg    300

tgaaatcagc aaacagtaat ttctctctca ccactggaat agttgctata agacggactg    360

caagagagga ctagaagaac atgtgaagaa gagtgagacc accacgctgg tcctctactt    420

gatgatgaac ggattgtggg gaggcaactg agggaatctc ccttgatctt ttgggaaata    480
```

```
tgccctcatc aagactgaaa a                                              501

<210> SEQ ID NO 7
<211> LENGTH: 653
<212> TYPE: DNA
<213> ORGANISM: Homo sapiens

<400> SEQUENCE: 7

tttatcacag cactattcac aataatgact tttacactgt caacaggatc cctaaaagcc     60

ttctctctcc cttgagttcc tatattttgt tcttttgcat ttatgtgttt gacacattcc    120

actttatatt tttattttca ctcccacaat aggtgaggtc tgtgtgtgaa taggaatttt    180

ttcatctgtg tgcctctaag tgcacctagc ttgaagctct gaatgttaaa cccaaacayg    240

tcttttgatg atagctgaga atgacttaat tctcatatta ttgacaaagt acaattgata    300

atatacatca tatcccataa tgacaaatga ctaggtattc aaacctacag gctgggaaga    360

gttcaaactt ttcttctgga tcacagggga aaacctcagg gagtttttct acacttggaa    420

catgattctg ttaccatata aagtaggaag caatgaactc aaaagaaaga tgtttatcct    480

gatatatctt tctcattcct gaaggaatgt tttcacccta tggctttgcc ttggggtgaa    540

acaatgtcaa atgatttaac gcaaatggaa aatgccaacc ttttaggttg gtttctaaat    600

cctttacata gttacacgtg ggagctacat atagatgagc tggttggttg gcc           653

<210> SEQ ID NO 8
<211> LENGTH: 648
<212> TYPE: DNA
<213> ORGANISM: Homo sapiens

<400> SEQUENCE: 8

ctgccatttt tgtagttggt gagcaaagca agaaagcagg ccacttcctc cacatgttta     60

ggaaagctat ttcatccatc acttagtagg aaattaaccc tggcctgtac cagggagaaa    120

gaagagcctg aatgaggtca tgatcactcc acatagatcc tttcaacctt ggctagaaaa    180

atccagtgtt gagcttttgg tgaagaatct tccaaaattt aggttataca ggttatttat    240

ttatacgtty ctctatgtct gtgtgtgtct gtgtatgtat ttaggttgac agatgggtat    300

aacctttta caaaatagga tcatgctata catgctatta tataacctta tttttttgg     360

tttacgtttt tttcattttg tttcatattc tgttgaatgt ttattcattc actcacccta    420

tttacaaata aaaaagagaa atattctttc cactctcatt tatttagtag tagttagaga    480

gcaagacaat aatcaattaa ttataccaaa tcaatgtgaa ggagctctga gggaaagtta    540

ctctgggagt gcctaacaga ggggaccagt ttctaaggaa atgacacttc agctagaatc    600

tgaagactag catgtggagg tagaattggg gtaggaaaag aggggact                 648

<210> SEQ ID NO 9
<211> LENGTH: 1001
<212> TYPE: DNA
<213> ORGANISM: Homo sapiens

<400> SEQUENCE: 9

cttatttatt tatacgtacc tatgtttttc tttctggaag cttatatgat tttctcttta     60

ttcttgaagt tctgaaattt tacccaagtg catttattta tttagagatg gagtttccct    120

cttgctgccc aggctggagt gcaatggtgc gatctcggct caccgcaact tccatctccc    180

gggttcaagt gattctcctg cctcagcctc ctgagtagct aggattacag gcatgctcca    240

ccacgcctgg ctaattttgt gtttttagta gagacagggt ttctccatgt tggtcaggct    300
```

ggtctcgaac tcccgacctc aggtgatctg cccacctttg cctcccaaaa tgctgggatt 360
acaggcgtga gccatcgcac ccagccaccc aagtgcattt aaatgtgata tttctttact 420
catccttatt gccctcagtg ggtcccttaa aacaactcaa acaaaacaaa atacttattt 480
ggcttagtac caaaaaatat ytcgaagcaa acaaagatgg ctcacaatac caccagccag 540
ataactccaa ttaacatttt taaagcataa aataagccag gtgtggtggc ccatgcctgc 600
aatcccacca ctttggaagt ctgaggtgga aggattgctt aagcccagga gtttgagacc 660
agcctgggca attgaaggat gagaatgggt ggagaagaac tttattgaac aacagaacag 720
ctctcagcag aggggggatg caggggggtag tcccccaccc ccacagttag gtggtttctc 780
tccctgtgtg gctgggtcca gggcttttca tggactcaga atggggaacg tgtgctgatt 840
ggtttgtgag tatgcaaaaa aggttaaagc aaggatatca ctcaagggtg ggcacaacag 900
tgtagaaaac caattaggaa agggtaggta tatgtcaaat aggtgaaggg aagggatcaa 960
tcaggaaagc atgtcaaacg ggatgacagg ttctcaatct g 1001

<210> SEQ ID NO 10
<211> LENGTH: 601
<212> TYPE: DNA
<213> ORGANISM: Homo sapiens

<400> SEQUENCE: 10
agctgctgcg accacatcag agtctcagcg tgtgtttggg ggtgggtttg aggctgtctg 60
ttgcagagca gtgtagatga ggtagttcat ccggagtggc acttgaccct ggagttgcat 120
aggaatcacc tacaaggagc tctaaaaatg ctgatgccca ggcccctcgc cagaccgttc 180
catctatgtc tccaacatag tagcgcagga atgtggactt ttaaaactct cccccaagtg 240
atttgaatgt gcagccaagg ttgagaatct ccttgtgatg gaaccacctc actgttagac 300
ygaggccttt ggaattctgc cgggtaacgt ttcctaatga accaagcatt tgctgcagct 360
gttagtggcc gaggtgctat gtcatggtgg aggtgtcgcc acaccccgtc ttgttctcag 420
ttttttctcc tacagtcaag ttagggtggg gagtgttgtg cactgaggaa agtttgagtc 480
aaatagtctt taaagtcttt ctcacagctc tcaaagcctt taattgtttt ttgttcatca 540
cagaggagaa aatctaatta ataataacag atttaatcaa ctccaagtat tgcttttaaa 600
a 601

<210> SEQ ID NO 11
<211> LENGTH: 1001
<212> TYPE: DNA
<213> ORGANISM: Homo sapiens

<400> SEQUENCE: 11
ttgagcccag gagttcgaga ccagcctgga caataaagga aacccctgtc tctacaaaac 60
aaacaaacaa aaacagtaag acaagactcc tcctatctcc ccaaaaacag aaaattattt 120
aactttgtta agaattaaga acttctatat ggtgaaaaga aagtttttaa aaagctacaa 180
cccaagagat tggttgcaca taaatcaatt agtatccaaa atatataagt aactccagaa 240
catcaataag aaaaatacaa acagatcaac agaaaacaac aaaagacatg atgggcattt 300
catagaaaac atgaatagca aaacacacaa atatattcca tatttttagg gaggaaatat 360
aagtttaagc cgttatgaga taccatttta tacaagccaa gctgatagaa atttaaagtt 420
ttgataagac caagtgttag tgaggatgtg gaacaatagg aactcataca ctactgataa 480

```
gaacgtatat tggtaaaaca rtgagacagt atatcatgcc agtcagaatg gcgattatta    540

aaaagtcaaa aacaaatgat gccgaggttg cagagaaaaa ggaatgtttt acactattgg    600

tgggagtgta aactagttca atcattgtgg aagacagtgt ggcaattcct caaagatcta    660

gatgcagaaa taccatttga cccagcaatc ccattactgg gtatataccc aaagggatat    720

taattattct gttataaaga tacaagcaca catatgttca ctgcagcact ttttacaata    780

gcaaagacat ggaatcaacc caaatgccca tcagtgatag actggataaa gaaaatgtgg    840

tacatacaca ccatggaata ctatgcagcc ataaaaagga atgagatcat gtcctttgca    900

gggacatgga tggagctgga agctgctatc ctcagcaaac taacgcagga acagaaaacc    960

aaacaccgca tgttctcact tataagtgga agctgaacaa t                       1001
```

<210> SEQ ID NO 12
<211> LENGTH: 701
<212> TYPE: DNA
<213> ORGANISM: Homo sapiens

<400> SEQUENCE: 12

```
aagcaattct cctgcctcag ccttccgagt agcgggtatt acaggcaacc gccaccacgc     60

ctggctaatt ttttgtattt tctttttagt agagatgggg tttcactgtg ttggccaggc    120

tggtcttgaa ctcctgactt caaggtgatc cacctgcctt ggcctcccaa agtgctggga    180

taacaggtgt gagccactgc acctggcctg aatttcttta tgtaattgaa cacacaattc    240

tacacagtta attctcacac aatttatttg acacataggt ctaccatttt tttttctatt    300

ttacagatga aatgatgttc agagaagtag aagtgactta cctaaagtca gctagtggct    360

gattcagact cagattcagt ccctatggct aggctagaat caccctaact atcctattac    420

ctttcatcaa tgaccacaga aaccgctatt gttttccaga agttagaact gttttcagag    480

gtgcattgga cattctaagc mttattctaa gcttggaaaa caaagtgctg gagatttgtt    540

aaattagcac tacagagtac agagttttga gcaaagtcgt attaaaaact caataaacaa    600

tattcttgct caataaaagt gcttgacttt tttttttttt caaaagtaca tattatggtc    660

attaaatgcc attaagagaa actaggcttg ttgaaatgta a                        701
```

<210> SEQ ID NO 13
<211> LENGTH: 401
<212> TYPE: DNA
<213> ORGANISM: Homo sapiens

<400> SEQUENCE: 13

```
tgaaaagtca ttttactgat tagcagctgc agggcacttg ggtggtttga attatgaatt     60

atatttgagt tttaaacaat tttttggtta taaaaggtta aattttcctc gcttgtctca    120

gaaaggagac taaaaaattg agtaaaatca agaaacgtgt tagcacacat atatacacgt    180

acacacggga gactttcaaa rctttttttct taaactgatg aattaatgtt aactaagcct    240

tattaagtcc atactttaaa tattctaaaa gaattttgat ttaacatttt ctactttcat    300

aattatagta aggaaaataa accgtaaatt ggaatatata tatttagaat ttgtttaatt    360

aactaacatg aaatgtgtgc caatattatc agttataaag a                        401
```

<210> SEQ ID NO 14
<211> LENGTH: 739
<212> TYPE: DNA
<213> ORGANISM: Homo sapiens

<400> SEQUENCE: 14

```
aagccagcag acaatcagtt caggcaaaca gagcgaaaac ttcactttta gtgataatca     60

gcacaagtta gatgctatca tggaaagaag cagcttctag aattaagctg cgaagtcatc    120

ttagaggcag aagccctcta tttttaaaac gaaagcctcg ttttagttct agcgaaggtc    180

gaataggaca tgtgtcccct tacagatgaa cattcaaccc tcagtgatgt gaagaacgta    240

actraagaat ataatgtaaa aagaacattt ttctaagagg taaaaagcta ttatgtttcc    300

tgggccaggg tctactcagt gaaattcagc ctggtgatga gactaaaacg tgtttattat    360

ttattccccc cacccccatc ctcctttctc ctcattttag ggtcgcaaag atgaatttgt    420

ttaaatctac agctctccaa gcgcaccgag aacagtgctt ggcatacaat agtatccaat    480

aaatattgtt gaatgaattc aaatttcatc tgcagaaaag gtaaccttac tgatatttgt    540

cttcaatctc cccaactttt taaagatttc aaatcttcag aaaaaaaagg tacaatacta    600

aaacgaatac cagtttactt attaacattt tgccacattt tctctacatg tacatactgt    660

ttctgttcaa ctatttgaga attagttaca gaaaccatga catgtcactc ctaagtattt    720

aggtatacag ctgagaaga                                                 739


<210> SEQ ID NO 15
<211> LENGTH: 701
<212> TYPE: DNA
<213> ORGANISM: Homo sapiens

<400> SEQUENCE: 15

ttgttcacaa tcaacttgtt tctggattaa ttttgttgta cataaatgat ttgatatttt     60

atcacaagtt agttgatatt ctatcacact gtcacaaatg gcacaacgag ctccaacccc    120

atctttgcca ggcatgaaaa agaaactaag cacatcacag atgttcaaat tgtatggtct    180

taacttcatt ttgggtttag gtataagttc attttctgag atcacttttt atcaaattac    240

tatcattggt ggaatccagg tattcttttg ccacatcaag atctccagtg taaaaaatca    300

gcttaggaaa acattactgc ataggtattc tcttttcagt tgcaacagaa aatactttat    360

tttcaaaatc ttctatttat tatttttaag ttaacaaaat tggtgaaaat tttaatacat    420

gtttgttttg ttttgttttg tttttttgtt gtttttagca gaaagttttc atgctatctc    480

tgttgctttt gtggattgac rgaggtggaa ctttgatagc tttatgttgt gttttcatgg    540

tcagtcactg aatatatccg tcgtctccaa cattgtcgta gagaatatcg ctgagtaaat    600

gttagggtac tagagtcagc aagtctgtgc ttgaatttat agtaatgttt gggtcaatct    660

agggttccac agtggagaat ggcacacaat tacctctcac t                        701


<210> SEQ ID NO 16
<211> LENGTH: 509
<212> TYPE: DNA
<213> ORGANISM: Homo sapiens

<400> SEQUENCE: 16

taacccaagc ttaggctcaa gagggaatat cagcagagag ataggaaagt gaagagtggt     60

accatgggat ggcccaagtt cagataccct ttgaaggcag ggctggagac tgtgttcgat    120

tgggaatggg agaggccctg tcctcagcct gtggagccac tggcccctgt gctttcttgt    180

tctaattcac agaaycagga aagaggagag ggtgggatgg gaagggctgg cacccctgct    240

gcatccacct ctagcctttg gaaggcgatc aggaagctgt gctgatggta ctggacgggc    300

agctgctgac tgaggaagcg atggctctgt gcccaaggtg ggctttgtga ccaggggaag    360
```

```
tcctttccag aggaagccct tgaagccaag tatcctataa ggggaggatt ctgtgtcttc    420

tttttcttac tttccttttt tgagaaagcc tctagactcg taccacccga gtcactgttt    480

atttagcgct cttgcaaggc tggctcttg                                      509


<210> SEQ ID NO 17
<211> LENGTH: 201
<212> TYPE: DNA
<213> ORGANISM: Homo sapiens

<400> SEQUENCE: 17

tctctgtaac ctcagtccct gtgtcttcag ctctgagcct ccctccttga atgatcctcc     60

aagttcctgt cctgacctca ggaggaaaag ggatgaaaga yagagaaaag gaaaggaaag    120

atagggagga gagaaggcag acacataaga gtaagggcaa ttgagggcaa ggacctgaag    180

gatgaagaca ggggaacaag a                                              201


<210> SEQ ID NO 18
<211> LENGTH: 782
<212> TYPE: DNA
<213> ORGANISM: Homo sapiens

<400> SEQUENCE: 18

cctctggctc tgagttctct tttaggatct attgtctgca tatatgtcat tgactcagac     60

ataaatctca aagtggccca tacaatatat ttgcataatg aattaaataa aataaattat    120

agtaaaaata ggcaggtagg caggcatggt ggctcatgcc tgtaatccca gcacttggga    180

ggccaaggca aggcaggaag atcacttgag gtcaaaaaga ccagcctggc caaaatgacg    240

aaatcttgtc tctactaaaa atacaaaatg ttagctgggc atggtaacat gtgcctgtgg    300

tcccagctac tcgggaggct gaggcacaag aatcacttga attcgggagg tggagggtgc    360

agtgagcttg aactcaggag gtggagggtg cagtgagctg aaattgagcc actacactcc    420

agcctaggtg acagagtgag actgcatctc aaaaaaataa attaaaaaag gaggaaaaat    480

ggggtaataa aatagatatt catgtcaaaa taatatgatt tcaaattaaa cactaggtat    540

actaattctt aacatgtctc ttggccacac aaccaccacc tkttattttg actcatcatt    600

ttacataaac accacccaca tagagtctct ttggtttcac tctgtctttt cttgtgggac    660

tttgtttaat tgttcaacaa ttaaacaata cctgtttacc atctcagatg taaaagttaa    720

atcaactgag gggttgtttt atgtttctga tgacatttat ttttgtgata tctaatagtc    780

ta                                                                   782


<210> SEQ ID NO 19
<211> LENGTH: 601
<212> TYPE: DNA
<213> ORGANISM: Homo sapiens

<400> SEQUENCE: 19

ttcttagtct tcagcatcag aattctgatc ttacccacct ggaataattt ctctaaatca     60

tacttttatt tttatagtaa tttgaattgg gttagacaat gctgaatgat agcatcaaaa    120

acagagaact tcaatgatat acaaagaaag ttccataagt attcatgagt ttgttcagca    180

cgtcaaggca gtgttaatga gattttgctt taatcactcc cttcctgtta cccctgcaga    240

cccccaccaa tcctccctca ctgtgacctg atcatttatt ttcagtgaca agcacagctc    300

kgcctccggc ccagtaaatg ctgagaaatt gtcagatatt gaagttgtcc tggcctgccc    360

cttcagtgaa ccacacatta acattgaaga gtctggcagc agctgcatca ccttaaacta    420
```

```
gggaggctga atgtggaatt gtcctcgtcc tgagagaggt gttgtcacct gatgtttccg    480

ggttacctgg tggttccttg gtcaggaaca tgaaaggaca gcattccctg aacagattct    540

ccttgaattt cactgttgtt ctgtacttca atattaactt acagctgcct tgtggttata    600

t                                                                    601


<210> SEQ ID NO 20
<211> LENGTH: 674
<212> TYPE: DNA
<213> ORGANISM: Homo sapiens

<400> SEQUENCE: 20

tgtttcattt tgtttgtatt tctgatcttt agcttgtctg ttgccaaata gctctatgga     60

aagagaacag gggctttgaa ggcaaacagg ttgaatccta gctctactga taatggcttt    120

ctgacctctg caaagtagtt agtttctctg cacctccttt tcttcatctc taatgtgaga    180

ctaataggac ggttgtgagg gtcacattga gtgggctata agccaacttg cgaggtgggc    240

agttagaaat gtgggctccc ttccctttcc tcttgagaag cccaattcta gagagctttt    300

cccaagaggg aaagcatctt gatygcagtt atttctggct ggagtagagg tggcaggttc    360

tagctatcat aactcaaaga aactttaggg attatagcta tcatcataga atattaggct    420

cagaatgggc ctgagagatc ttttagttga aaccttctgt attgatgaga aaactttgac    480

ccagtgaggt caaagactct gaatcttaga gctataagag acttgagtag tcagtccctc    540

taattcaact tgcctcaacg ttcctgtaga acatacagca ttataaagtt attgtttaaa    600

gtatttcatc tctctgagaa tacttatccc tactccatgg atatgggaag ctgaataaat    660

atgggagtca agag                                                      674


<210> SEQ ID NO 21
<211> LENGTH: 601
<212> TYPE: DNA
<213> ORGANISM: Homo sapiens

<400> SEQUENCE: 21

ccaacaaccc ataaacttgg aagaggatcc aaaacctcaa ataaggtgat aataggctgc     60

ctggtgagac cttgagccga agatcctgtc aggtcatacc caattcctga cctatggaaa    120

ctgtgaggta ataaatggcc attgctttaa gctgacaagc ttgtggtact tggttataca    180

tcatggaaat gcatggtaat tcaatccaag gttagatcac cttttgttaa caattagtta    240

caaaaacatt ttagttctta agagatttct gaattttgaa attgtgaata aggaattgta    300

kgcctgtgat tgtatgactt cataaagtat ttaattgcta tgagctttag ttttctaatc    360

tttgaaagag aggcagtaac aacacctacc tcacagggtg gtggtgagaa cttaataaaa    420

tagtgtatat aagatacttg atataaaaca tgaaaccacc atcccactgc aaacgtttta    480

ttattattat tattttctac cctttgctct aaaccagtga tctcaacact atagctacat    540

gttaaaatca ccaggacagc tttaagaaat agcagtgcct gtgccccact ccatatcaat    600

c                                                                    601


<210> SEQ ID NO 22
<211> LENGTH: 3747
<212> TYPE: DNA
<213> ORGANISM: Homo sapiens

<400> SEQUENCE: 22
```

-continued

```
agaaagtagc ccagtctaat aatacagcag ttctcaacat attctttctg ctctgatatt     60
tgactggaga cattcacatc gctgatactt ctctaggaca tcctaagaat gtgtcacaga    120
caagaaagtc tgccgtttat gtgtgactcc taccacacca acttctgttt cccatccagg    180
aaatgtgtaa aaggatatta caggtggtgt ttcccttatc caaaatgctg gagaccagaa    240
atgttttgaa ttccagattt tttttggggg gtggtgggtg gcatttttgg aatggacaat    300
gagagatctt gaagatagga ccagagtcta aaaccaaaat tcatttatgt ttcatctgca    360
tcttatacac atagcctaga ggtaatttta tacagtattt taaatagttc tgtgcataga    420
ctggtgtgat tgccaggtgc gacagcatga ctgtagtccc agctacaacg gaggctgagg    480
tgggaagatc gcttgaggcc aggagttaga ggctgcaatg agctatgatc gcagcactgt    540
acaccagcct gggcaacaga gccaaactct gtttcaaaaa ataaacaaac aaattttgtg    600
catgaaacaa agtctgtgta catggaacca tcagaaagca gaggtatcac tatctcagcc    660
ctcaccccca tgtggacaat cagtggttgt gtggcatcac cctcattcct gactgtgact    720
ttttttttt ttttttgag acagtctctc tgtcacacag gctggagtgc agtggtgaaa      780
tcttggctca ctgcaatctc tacctcccag gctcaagcga ttcccctgcc tcagcctccc    840
aagtagctgg gactacatgc atgtgccatc acgcccggct aatttttgta atttttagta    900
gagatggggt tttgccatgt tggccaggct ggtgttgaac tcctggcctc aagtgatctg    960
cccgccttgg cctcccaaag tgctgggatt acaggcgtga gccaccgtgc ctgcccgtga   1020
ctctgaattt atatgctact accaagcagt catttcctta cacttattca cacataagta   1080
cttcacagta aaaaataaga catgccatta acacagtgaa gacttacgtg ctcaggggag   1140
ctaagcagcc agtggcatca gcagagaccg caatcagctg ctgaacaaca gcagcaacaa   1200
caaacaacag caggcctctg ctctcccaac catgctgtgc tttgattcaa agcttacggg   1260
acacggcatt ttacatttta ggtgagaagg aacataagaa gcagttacag gcccaggaag   1320
tgggtcctct ggggacgagg aggcattctg ctgggggct ttttaatggt atctgcacca    1380
ctaacaatgg tctyagaacc gacagctcct ttctgttggt tcagtgtaca caaagtttgt   1440
ttcatgtaca aaatatttac ttagtttttt gggttttttt gagacagggc ctcgctgttt   1500
cccaggctgg tgtgcagtgg catgatcacg gctcactgca gcctctaact cctgggctca   1560
ggcaagactc ttacctcagc ctcccacaca gctgggacta tagtcacgtg tcaccatgcc   1620
cggctaattt tttttctttc ttttttgtct taggattctt tctttgattt tataagctga   1680
catgattgct tgttctgttg tgaatgcacg ctgctctggg cctcagttaa cccatcacac   1740
ctgagctcca cgctgtccac gggtgctttt tctgcagtgt taacgtcatc ttcatggtcg   1800
gtatcatcac gatcaccttg attcagaacc attctggcta tttccccaac agtcaatgaa   1860
atgaacaacc ggagcctcat tatcaatgtt aaaaatgaca ttaatgtgta cttcttcccg   1920
ctgactgatg aactctgaag gtatattttt tggaggtcag acatcctttt cttctcactt   1980
gacaagctga attcttctaa accaccacct ggttcatcat catcactgaa cacagtcgta   2040
ggccagaggt cacgccaggc acgcacatct gtgtctttag tcactgtgtt gcaagcgttg   2100
gcaacagcat gtatggcatc cttcatgctc agctcctgaa aatcttctac acctacacct   2160
ccgttcactg ctgcgagcgt gcaattcaag acagtgtttt tatatttact tttcattgat   2220
ctaaagatac cctggttaca ggctcaacta atgaagtcac gtttggggga aagtacacag   2280
catcaatatt atctttgatg agaatttcag ctggaggatg agcagaacag tagtcaaggc   2340
ataagaaaat cttgctgtca tcatccggtc caacttttct gcagcgagca caagaggcct   2400
```

gtacgaagtg tttgtaaaac cgatcagaaa agatgtccct ggtgatctat gcctttttgt 2460
tagcataata atggactggt aagaaattta ctctttgaaa acagcacgga caaaagcttt 2520
tgcccatgag agcaggttta cacttatgcg tgcctgctgc atttgcacag cactgcacag 2580
tcattctgtc cttggcatcc ttaattcctg taggggctgt cccgtcagct gtagtcagca 2640
tctttctggg gcagtagcac ccaaatggtc atgtctcatc agcaatacag acttgttctg 2700
gcatcagatt ttcattagcg ataatcttgg caaactcgtc aatgagtttc gacgctgcct 2760
tgtgatctgc agatgcttta aaacttgaat tccatgtcat ttcttaaatt tctgcaacca 2820
gcctgttgaa tattcacagt tcccttcaat tttcagttca tcaggataga tcttcgcttg 2880
tttcatgatc agcctaccac tgagtggcac gggttcagtg tgatgccttc agatctagtt 2940
tttcaataca ctattcacat cttcattttt agctttacgt agagtttttc tatttttcat 3000
taacttctgc tcatcacatt cagcatagaa cttcaaaagc gtatccttct gtttcttcag 3060
gtcatgtatg gtggtcatcc caacaccata ctcttctgta agacgcttca cacttatact 3120
gctgttcagt tcctccaaca agttgactgt ttgtgctatt gataaacata aattattcct 3180
ctttttctga tcactgttac acataggggg atctgcaggc cttttcgaca ttttcagtaa 3240
tatttttaca tgacactgca gagaataagc aaaaaaccac agtgagtaat gcatggagtt 3300
ctcggcccca cgtgaggtat cgtggggaat ctgcgttggg tgcgtccagc ctgcacacgt 3360
gccattttat tacacattgt gggcgtgctt gtgtgggga atttgggtgt gcatggaaaa 3420
gttatactat agttgaaggg ggctgggtgg gtcttttttt tcccttgggg acgctaaatc 3480
aactgtgtcg tgcacctgtg ctttgactat gccctgtcac atgaggtcag gtgtggaatt 3540
ttccacttgt gttgacagat tggcactcaa aaagtttaag atatcggagc atttcagatt 3600
aaaattagga atgttcaacc tgtattacat ggctagcctt gaatccacta ttatttacta 3660
tgttttctgt tacattttat aattgtttat cattgggtat acaaatgcta aagatttcag 3720
tgagtggatc ttacaaagag gaatttt 3747

<210> SEQ ID NO 23
<211> LENGTH: 501
<212> TYPE: DNA
<213> ORGANISM: Homo sapiens

<400> SEQUENCE: 23
tctccagagg atatttttca ttcaaattaa gaaaaatctg acttagatta tatttcttta 60
aataaaacaa aagattttaa aacattttca caaactaaat caaatatgtt aaatattata 120
tattgatagg atattttagc aacaggtcaa cttctacatg ttactttgaa caaatgtctt 180
tatttcccaa tatgatatta gattaactaa aataggaatg tttttgttaa atattattga 240 taaccccac rccttccaca tttcaaaaac tgtgaaatct atgtagttcc accaaagcct 300 aggtttttg tttgctatta gatgttctta agagattttt gcactatttc ctgcattatt 360
acccttctct tgatcatact attttttaca gttgaaatgc taacacagtg aagttttctt 420
aataattgga agctgaatta tttgtaaaat tcatgacctc actgctatca atatttaata 480
aattatacta tgcagtatca t 501

<210> SEQ ID NO 24
<211> LENGTH: 701
<212> TYPE: DNA
<213> ORGANISM: Homo sapiens

<400> SEQUENCE: 24

```
agctgtgtcc actctggctt gtcatttgat aacgctacta acaggagcat aataacatca      60
actcttgact gttttataaa gtgtaatttt tttatttcga tttttaaatt ttaaaacata     120
taaagattat acttccaggt taaacctttg tctgactatt ccttgtaccc ccagaggcaa     180
ccactattgt gtttttacat ktattgcttc tatgtatgag tatacttttc ctattcatga     240
atttatcctt aaacaggaaa atggataagt aactgggata cttaagtctt gtattagaga     300
gatgctttgg agacagaagt tatattagaa aaggaggctg ggcgcagcgg ctcgtgcctg     360
taatcccagc actgtgggag gctgaggcgg gtagatcacc tgaggtcagg agttcgagac     420
cagcctggcc aacatggtga aatcctgtct ctaccaaaaa tacaaaaaaa aagaaaaaaa     480
aaattagctg gacatggtgg cgggtgcctg taatcccacc ttttgggagg ctgaggcagg     540
agaatcactt gaacccagga ggcggaggtt gcagtgagca gagagctccc cattgcactc     600
cagcctggac aacaagagcg taactccgtc tcaaaaaaaa aaaaagaaaa agaaaaagaa     660
aaagagattc tagagacagg aagattaatt agaagattgt t                         701
```

<210> SEQ ID NO 25
<211> LENGTH: 601
<212> TYPE: DNA
<213> ORGANISM: Homo sapiens

<400> SEQUENCE: 25

```
ggtcagttat atttgggatc tgggtccggg atacaaaact tggagtcagt tcattgcacc      60
tatttgctgt ttgaccttag aaaatttatt tccatttcta agtcttggtt tcatcatttc     120
tcaaatggga ataatcacag cctgctaact aacatcacag agaactttta agaatgaaaa     180
tgaagtaaca tatgttaaag cacagtaaag aaccaagcaa atgcaagact tttttttata     240
agaaggttct ttttaataag acgtcagtac tcaaagagtt gtcaatgagg atagatctca     300
rtatcatgct actgaaggag tttgtgtaga tggacaatgc ctcctgctcc aagagcaagc     360
acatggagaa agggtcaatg gacacatttg ttttgctgtt taacaacaaa gaaaaattat     420
gaattagaca aaatgtagtc tagatagaat ttatttttgt gaacattaat gagggtttgg     480
tcatgtattt attaaaacca tgtgttacgc catgcccggt ggctcatgcc tataatcaca     540
gcactttggg aggttgaggc gggtggatca cctgaggtca ggagtttgag accagcctgg     600
c                                                                     601
```

<210> SEQ ID NO 26
<211> LENGTH: 601
<212> TYPE: DNA
<213> ORGANISM: Homo sapiens

<400> SEQUENCE: 26

```
ttaaactgtg gctttctcct tttgtaccta tacttaacac tccttaagtt gattctctta      60
gtgtcaaact tgttgaaatt tctcattggt tatctctctg tatttgacat tgttctaaca     120
gtcgtataat ctgttgctgg gtgtttatat gtagtatttt cattacaata tcatactttt     180
gaagagcaaa tcaatggcct gggaaaaaaa tcagagggca tagtgcctca ttacctcttt     240
gttaatgttt ttctacctca atccttacaa tttttatccc gtgtatggac ttaaaatagt     300
rtgtgttgtt ggttggggga agatcataag tgaagacaag agagatgaag taaatagata     360
gagtttgaca atggggcatt ctgggggaag ttaacaccat ggagtcgaaa actttgttag     420
atacttagat atctggaaac tttaggcatt aatgtgtgtg aatatttcta tatgagttca     480
```

```
taataacgta caaaaagaac ccgcaaagca aacagacttg atgctgaact tgtttatacc    540
ttccaaagag ccaaaaattg agaaggcact cataaaaatt aatatccaac ctccactttc    600
a                                                                    601

<210> SEQ ID NO 27
<211> LENGTH: 2009
<212> TYPE: DNA
<213> ORGANISM: Homo sapiens

<400> SEQUENCE: 27

gtgacattcc tcattgaatg tcttttatac tgtttgtgtt tttaaacttt gtaactttaa     60
tgcctgtaaa gaaatcagtt taaaaatatg ctgatatggt ttggctgtgt ccccactgaa    120
atctcatctt gaattgtggt tcccattatc tccatgggtc ctgggagaga ccaggtgaag    180
ataattgagt catgggtcct gggagagacc aggtgaagat aattgagtca tgggggccat    240
ttccccccatc ctgttctcat aatagtcagt cagttctaaa gagagctggt ggttttaaaa    300
ggggcttccc ctttcactgg acactcattc tctttcctgc tgccctgtga agacgtagct    360
tccgccatga ctgtaagttt cttaaggcct ccccagccat ggggaactgt gagtccatta    420
aacctctttc ctttacaaaa tacccagtct tgggtatgtc cttacagtag catgagaatg    480
aactaataca tatgcctacc aaactgtcgc agccaagcgg agctaaggag atggacaact    540
cagtgtgaga tggtgaccaa gatgctctta agcttcccat cagcttgact aaacaccagg    600
caggcttctc cagtctctag atccctgacc tgccttttct taaagcattt actttagaaa    660
cttgcaattg taaattcttt ctctgcccct ttaagacata aatcttttat aaagtttctt    720
gccagtttta caatctagga ctgtctttct caaggacgtg ggagctattt ctttgaaatg    780
taatcatcaa ggaagacagt accccctatct cttagtcttt gtggaagggt ggaagcccaa    840
cttccatgga caccaattag caaacacaga tggcctaatc acagagaaat acatttgcaa    900
agtcaagaat aactcaatgt gctggacata tcctattgtt caatctccta atgtcctcca    960
gtacttttcc acttactcca gcaattaaaa accctcctgt ccttttcagt ttcagtgaaa   1020
ttgagttcag acctctctcc ttcctctatt gcaatagcct tgaataaagt ctttcttgcc   1080
tgtttaacat catccagtgt cattttgctt tgatgtctgt atgytgaatg ggctcctgta   1140
tcagaaaaag gacatcagat aaaaactaag gaaatctgaa taaagtatga actttaggta   1200
ataataatgt atcaatattg atttattaat tataacaaat gtaccataaa aatataagag   1260
gatgctatgg gaaactgatt gcagggtata tggaaactct ctgtactatc tttgtggttt   1320
atctataaat ctaaaactgt ttaaaataaa aaaatatatt tttaaaatcc tatctgaacc   1380
tggaggacat catgctaagt gaaataagcc aaacacagaa agacaaatac tgcatgttct   1440
cacttgtatg tggaatctaa aaagtcaaac tcgtattaga gagtagaatg gtggttatca   1500
gaggcagggg gtgggaagaa gatgaggaat tgcggggaga tgaagaatag ggagagattg   1560
gtcaaagggt acaatgtttc gattagacag gaggagcaag ttttagtcca ttgctcagtg   1620
tggtgaccat cgttaataat ggattatata tttcaaaaat ttgctttgaa aagtttttta   1680
atattctcat cacaaaaagt atgtgagatg atgaacatgt ttattagctt gatttaatca   1740
ttccacagtg agcacatatg tcaaaacatc acattctatc tcataaatat atagaagtag   1800
tatttgtaca ttaaaatata tattaaaaat aaccctatct gagtggaata cggaaaagaa   1860
catccaagtg tcagaaagat ccagtaagta aggctctgac accagctatg tgatgacagt   1920
```

```
caagtcatca gatctctttg agacccagtt acctcattta taaaatgaca cttgcaaatc   1980

cactaacatc atgcattctc agtagtcgc                                     2009
```

<210> SEQ ID NO 28
<211> LENGTH: 1000
<212> TYPE: DNA
<213> ORGANISM: Homo sapiens

<400> SEQUENCE: 28

```
gagccgtgga cccagcccag gggagggggt tagggaatgt ggtgcacacg aggcctggct     60

aagctagggc tcaggacagg acttgtggca ggaaggatcc cacgttgtta acccaagaca    120

gcagatagga gttgttgcag gtccctcttc cggaagcacc tctgaaacgg aaacggtgtg    180

tgcggtgttt atcaggaagt gctctcagac tccacgcccg tgggagtagt gagaggcata    240

ggatgggaca gaaggagatg ctaaacagtg atgcagaagc agcgaagacc tccgcaatcc    300

tgcagggaag cttgggagct ggtacggccc tgcagagatg cactgaggta gggcgaggac    360

cccggccctc taatccccg cactgactcg acattggatg cacagcccct gggaagggga     420

tgtgacgggc gaggtggctc tcggcatctg agagcaatcc ctggcgacag actcagctga    480

gagctcatct gagggcaatc yctggagaca gactcagctc agagctgtca gcagcctgag    540

gactgtgttt cttcttggac gggtagggac cccaggggaa cccgggcagc acacctcacg    600

ccccctgcag gcacagtgct gcaactacag ccaaccatcc ggaggggaga attcaggtgc    660

gagaggccca gggaggaagc cgagggagac tccaggccct agtgagaagg cagcgcacag    720

ccagcaaggc ggacccacct agctgggtcc tgcctgcaga catcgtagtc agcatctgcg    780

gccgtggcgt caaccagtag gaagcggatt aggacccaac caggctcagc caggctccac    840

cacgctaagg ttctgggctc tcccagcatc tctgaggact gagggaggcc ccagcctggg    900

cagaggacac ctctgaggtc gtgcaaatag ttttctatga agctcgtctt ctgctgctct    960

tccacccatt gtccatcagt ccttgccact tccttgtcct                         1000
```

<210> SEQ ID NO 29
<211> LENGTH: 2937
<212> TYPE: DNA
<213> ORGANISM: Homo sapiens

<400> SEQUENCE: 29

```
ccagttagat ctaacagata tctacagaca acttcaacca gttatagtag aaaaagtatt     60

cttcttaggt acacatctaa cagcttccag gatacatcat acatcatgct gtgaaaaaaa    120

gcctcattaa attcaaaagg attgaattta tgcaaactgt tttctaacca cagtacaata    180

cttgacaaaa acatcacaag aaaattacaa atcaatatca cttagaaata tagatcttag    240

agtcctaaac agaatacaac tgatacgtac atgcaataaa taaattatac ccctacctta    300

caccatatcc aaaatttaac tcaaaatgaa ttatggactt gagtaaaaga gttaaatcta    360

taaaactctt agaggaatac agaattttaa atctttatga ccttggatta ggcaaaggtt    420

tcttgtgtat gacaccaaaa acacaggtaa ctaaagaaga aatacgtaag ttaggcatca    480

ccaaattaaa aacttttgtg ctttaaagaa caccgtcaag gaagtaaact gacaacttac    540

atacagaagg agagaaaata tttgcaaatt acatatctag taaaagtgta gtacccaaat    600

tatgtttaaa aattatacct cagaaataag gtaaattata tttcaaaata gacaatgaat    660

ttgactaaac gtgcttccaa agaagatata aaaatggcca ataagcacac aaaaagatgt    720

ttcatatcat tagtaattac ggaaatgcaa acccaaacca cagtgagcta ctactttgaa    780
```

```
catgctagaa tggctaacat gaaaaaggca gataatatca ggtcttggtg agaatgttga    840

gaaatgaaag cactcataac ttttgtgtct gtttgtgtag ccatttataa acaaaaagtg    900

gtatatccat agataaaatt gtatctggta ataaaatatg tgcagtactg atacttgcta    960

aaattggtta atccttgaaa acattataag taaaagaagc tggctaaaaa ggccacactg   1020

aatactggca tttatctaaa acgtccagaa taggcagatc catcaagaga aagtacactg   1080

atagttgcaa ggatctggcc aagtgtagga aagagaatga ctgtttcttc acagtgagtt   1140

ttttggggta gcgatgaaaa tgttctttag tgatctagtg gtgccgattg gacaactctg   1200

tgtatatatt aaaatacact gaattgtata ctttcaaagg ctgaatttta tgatatatga   1260

attatatctt agtaaagctg cttttccaaa aattctaaag ttacaggccc atgtaaggca   1320

tagtaattca tgaaaattta gaattgttta aaaagtttta tttatatatt tatgcattgc   1380

tcaatcagca tgcataaact ttttatagtg ttcaggttat gtctttccct ctttgggtcc   1440

aggatctatt tctttaggtt ctacattgcc aaagtggtat tctttgatca ttttgcatgt   1500

ctcagcatgt cataaaaagg tagtgatgct gttatttatc acgagccatg tctcttagga   1560

actttttct attgcaatag tagtgatatt cttgcctttg ctgttaatga acgccattta    1620

tatactgctg gttgtatcat tgctcatgat gctgtatcac ctcttttgcc tcccatgaat   1680

attgtcttcc aatgtttcta tcatatgtta tttctttatt cttttagtga tgaccgaaag   1740

tacaagtctt actcagagta tgcaggaaaa tgtgagcaat acttgttttc tggtcgtgtt   1800

aaatttagca attggaattt ggtaacataa atataaaaca atccatgttc tttccatatc   1860

tcaaaaaata catacattct aggatgtgga cctttcccta aattaaccat atctccttct   1920

tccaaacact acaatcagga agaaagacca gtgaaaaact gcacgtagac tgagaacagc   1980

agtttcattt atacaaactr tatccctccc tcatctggct tggcctcaga ttgacaaagc   2040

agaccatgat gtcccagttg gaagtaagag aggacatcac ttggctccct ccaaaatcct   2100

cagaaaagat taacatagct gccactagag gactgcctga catatgtcct gatctttaaa   2160

gaacatgatg actgtcttct atgcagtgtc aaagggcaca gagagtaaag gcctcctacc   2220

accatttctg ccatccttga gggctgtcgt tcaaaggcag tactgcagtg acaacactga   2280

caagtgagag ttaaccaacc agcaagaact gatgcatgag tctacgttta tagctcaaac   2340

ccaagacata gtggatgatt gctagccaag aaccatgcat tcatctcttg tccgacatgg   2400

aagagtcacc taaaatcagc atgactgtac cattctgcct gtccaatttc atgcagtttc   2460

acaaaggaaa tataatgtaa gtcagagaaa atgattcact tgcgagtccg ccttcttaaa   2520

actagagaat ggccaggaga tttaaagaca acctcccagg tgcaagtcct ggagcttgtt   2580

agagcatcta gtcaagtgca catgtgagac tggggagtta gaagggttgg agagagtctt   2640

caaggagtga aatggtgact gaggctcaca tagtttgaag tgggattggc cactcatctt   2700

aaatggcagg ccagccctat ctcatctcag gcactgaaat gggatttatt aatagaaact   2760

tttgagaaag gcattccaaa gaacagaggt gaagtgccaa ggacaggatt cttgtttggg   2820

tctaaaggca atattgtttg aagtataaga attttagatg aagttctaat gttgctattt   2880

taatccttta cttctcctta gaatagagga acaattattt caagcactgg acaagag      2937
```

<210> SEQ ID NO 30
<211> LENGTH: 851
<212> TYPE: DNA
<213> ORGANISM: Homo sapiens

<400> SEQUENCE: 30
gtttgcaagg acatctccct ggttattacc tttacttata ttgggattcc actttaacaa 60
atgctgtggt attcacctat atttgttttc agagtgtgct atatttccat tatgatttcc 120
taaaaatgcc tttctgcctc ctctatatgt tctgcttcct gaatcattta acaggtatta 180
tactttgtgc acagacacac ctattttgtt tattgatcag tctgtttgct cctgttctca 240
tacctcattg tttttattca ctcgttttgt atatgcttaa aatctggcag ggaaagtcat 300
ttagctttgt tcttcttttc aaaattagaa tagttaccag caaatctaca ytagtctata 360
taaattttta accttgtatg agtattgaaa tttacatata gaagtgtacc taaaacacgt 420
gtgtgtgtgt gtatatatat atatatattt tttgagacag agttttgctc ttgtcgccca 480
ggttggagtg caatggtgtg atcttggctc accgcaacct ccgcctcctg ggttcaagcg 540
actctcctgc ctcagcctcc cgagtagctg ggattacagg catgcaccac cacgcctggc 600
taattttgta tttttagtag agatggggtt tctccatgtt ggtcaggctg gtcttgaact 660
cctgacctca ggtgatccac ccgccttggc ttcccaaagt gctgggatta caggcgtgag 720
ccaccgcacc cagccacgtg tgtatattta aaagaattat tataaacaga acatgtattt 780
aaccaccatt caaatgacaa aatctaactt aagcgtaatt aagaaaacac ctgtgtgcaa 840
cttcagaata a 851

<210> SEQ ID NO 31
<211> LENGTH: 601
<212> TYPE: DNA
<213> ORGANISM: Homo sapiens

<400> SEQUENCE: 31
tgtgccttgg gaagagctct gggcctctgg gggccgtgtg ccctcccggg acatggctgt 60
ccctcttcaa aatgtcactc tcttcgccca ccctgaattc cagtagctgc ctcttgtgca 120
caagcatagc cgacaggctc aaactcggct tagctagatg tggacaggtc gtggctgcct 180
gccccacgca acacagagtc tgctaaatgc aggcacctgc tgtgtgtggt gcacgttgtt 240
cccagtgggt caggctgcct gtacagggag gtcctgtgtt ccctgggcac gtctgtgcat 300
ktgtggcaac atgattatgc aggccctgtc acctgtttgt gtgcccatcc ctgcacatgc 360
agctggctgg ctcctatgaa aggaggaggg tctggaggtt ttggggtgta tagctttcct 420
aggcgatatg tgcagtgtta acgtgtgcat tggctggaaa gtgtgaaagg gaggcggctc 480
aattgggttc ggccggacag catcttaaca taggtctcag ctgctgtgtg tacaggaata 540
gtgtcccagg ggtctgcagt gtgtggcaag tattctgagg tggggttgtg agaagaggca 600
g 601

<210> SEQ ID NO 32
<211> LENGTH: 757
<212> TYPE: DNA
<213> ORGANISM: Homo sapiens

<400> SEQUENCE: 32
gctgttgttt cctaatgtca cctccctcag taaaaaggaa tatacatgat caataaatgc 60
gatatcttta ggaacacaaa gaaaagggat aaacgaggaa tatataagaa ataaagggag 120
ggatagcatt aggagatata cctaatgtta aatgacgagt taatgggtgc agcacaccaa 180
catggaacat gtatacatat gtaacaaacc tgcacgttgt gcacatgtac cctaaaactt 240
aaagtataat aaaaataaat caataaataa aaattaaaaa ataaataaat aaaaatcaat 300

```
attcatcaga aaaaaagaaa taaaaagcaa tctacaaaat gtttaaaata aaaaccctaa    360

tctcaaaaca atgcgagaay aatgtcaggc acaagaagca agaagcataa gaaaaactag    420

aaacaaaaaa aaaaaaggtg ttgcccaatt tgaacaggaa aacaatagat aactcaaaaa    480

agctgattct tttaaatcaa aaattagcct taagagattt tttagtgtta tttaccgagc    540

actattctaa gtgctttaca cttagatcca ttacacttca tcttcacaaa accctcgaag    600

gatggtacta ttagcgccgc tcccatttcc tagtgctgag gcgcagggag gttaagttaa    660

ttagggcagt gctagatctg ggtcttgacc ccatctgaag ccagcacctg caagcatcac    720

tactgctaat acttgccatc cattctttaa aagccat                             757

<210> SEQ ID NO 33
<211> LENGTH: 401
<212> TYPE: DNA
<213> ORGANISM: Homo sapiens

<400> SEQUENCE: 33

cccctataga agtaaatctt cacttcacca cttatccttg agcagaagag gactgtagtt     60

gatgattcac atgagaggat gacaattcaa tctcaattag cgtagattct tgaaacattt    120

ccaggttgaa gtagctattc tcagccctcc ataggctgga ctgtcctccc cagaggactt    180

cttagaattc aattctggcc yatgagacca acaccagatc taagcctagc tgggcgtacc    240

tgaagcctca gcatgcccca atgtaacatg caggcgtttg gccatatggt gtcccctgag    300

cttgccgttc tctgatttat gccagaatgg gcatatgctg ggatatttca ggaccctgag    360

gggagagtca aaatgtcaca cagccagtat gaggttaagc t                        401

<210> SEQ ID NO 34
<211> LENGTH: 5361
<212> TYPE: DNA
<213> ORGANISM: Homo sapiens

<400> SEQUENCE: 34

atatatcttc tgtaataaga tatagatatc atctgtaata agatatatat gtcttctgta     60

ataagatata tatatctttt gtaataagat atagatatct tctataataa gatatagata    120

tcgtatatgt atatgatata tatataatat atatcttatt acagaactcc gaagtacatg    180

aagcaaaaac tgacagacat aatggagaaa cagaaaaatg gacaatggtg attttaacac    240

atctcttcca tcatacatat atatatatat ataaaacctt gaataattta tatgttatgt    300

atgtatagac acacacatat gtatgtatta tatataattt atataattat ataaatatat    360

aattatatat tatataaata tataatttat attatatata acttatatat tatataatat    420

ataatttata ttatatataa cttatatatt atataatata taatttatat tatatataac    480

ttatatatta tataatatat aatttatatt atatataact tatatattat attaaatata    540

taatttatat tatatataaa ttatatatta tattaaatat ataatatata atttataatt    600

tatatattat agataaatat ataatttata tatacataat gtacattaaa tatacattat    660

atgtatatat tatattatat aaatagatat aaaatttata tataaaattt acatattata    720

tatgtataca catatatgtg tgtattatat atatatgtat aatcttgaag aatatatata    780

atcttccaga tttttctagg tagacaatct tgttttttac gataaggagc aattatattt    840

ctttctagtc tgtgtctctt atttatttat ttttggtttt gtttcattgc actgggtaag    900

actactgata agattttgta tagagtggtg aaagcagaaa tccctgtctt ttacacaatc    960
```

-continued

```
acagaggaga gaaactttaa gtcttttttt cactaagcat aattttagca gtagtttttt   1020
gtttgttttt tgtttttgta gatgcccttt atcaacttga caatgtttcc ttctattact   1080
agtttgctga gagtattatc atgaagggct gttgaaattg ccaaacttcc catgtgccaa   1140
aagataataa taaagctytt ctttttgctt gatatgatga attgcagtga actctcatta   1200
tacatagatc tgtatttgtg aatatatcta cttgctaaaa tttatttgta agcctcaagt   1260
caaaacttgt ggtgcttttg ctgcatttgc agacatgcac agaggagtga aaaatttgag   1320
taacccaatg tgcacatttc cagctgaggt cgacaaggct atattctgcc ttgttttagc   1380
tgtcatacta tgaccaagca tcctttttat ggtgtattga ttggcacatt ttttacatgt   1440
ttgtgcattt tgttaattat tttgctgttt aaaggggccc ccaagcatac caatgaagta   1500
ctatctagcg ttccttacag agagaatacg tgtgttcaag ctttcttcag gtatgagtta   1560
aggtgctctt ggatatgagt tcaatgttaa ttaattaaca atatatatta aataaagtgt   1620
tttgaaacag aaacacacat ccaacagggt tatatttgat cagttgttga aaatgttgtg   1680
accagaaact cagaggaacc taatcttgca tttcttctag gagcaatgat tcagtattcg   1740
ttacttcaat gttgatgtac actttataga acataactac tatgaatgag catcacttgt   1800
atactaactg aagtttgaat gttgaaacat tcttacattc ttgaaatgaa tcccatttgg   1860
tgattttgtg ttactctttt tacttcttgt tgtatttcat gtgttggtac tttatttaaa   1920
gtttttgtgt gcatgttccc gagggatatt attctttagt tttcttcttt gtaagttttt   1980
ctgttgtttg gaattagggt aacattggcc tcataaaatg agcgaggagg catttccttc   2040
tcctctatac tctggataca tttttggaaa attgtcatta tctcttcctt aaatattaga   2100
caaagtccat cagtaaaacc atataagcct ccagtttact ttgttggaga gtttttaagt   2160
atcaatttga ttatttagta gatttagaaa tattcagttt atctatttct ttttcattga   2220
tttttgagag ttgggagtct ttcgaagaat tttattattt catctaagtt tttgaaatta   2280
tggatgtaga gttactcata catagtatta ttaaccatag tgatagcccc tctttgattt   2340
ccggtattcg taatttctgt attttctctt ttttcttgat tggcctcagt tttattgatt   2400
tgttattaaa ggaatgagat tttagtttta tttcttttct ttttttttgtt ctcattgact   2460
tctgctttta ttttttattt attattttca tttttttcct tctacttgct ttggatttaa   2520
ttttctctgt tatttctatg tttcttaaaa tggaatcaga atattgattt gaggtatttt   2580
ctctcacgta atgtaaacat ttaacatatg cattttatat atttaatata taaattctca   2640
taaagtgctg ctttagtggc atcatccaaa ttccaccatg ctatgttttt actttcattc   2700
aattcaaaat attgttaact tccctgttat gttgtctttg acctccatgg cctattagaa   2760
ctgtattgtt taatttccaa atatgcagag ggattttcta ggtatcttct ggctactgat   2820
ttctaatttt aatctattat tgttacaaaa catgtttcct agggaattgt tagagaattg   2880
tttgtggata tcaatcattt aattatgttg aggtttggtt tttggcctaa aatatggtct   2940
ttcttgaaga atgtcccatt tgcacttgaa aagactatat attcagctat tatttagtgg   3000
catattctat aaatagcaaa gaaatgaagc tgatttataa tgtttttcag gtttactaag   3060
tacttactga atttttgtct atgctttaat tttctgttga aagctcacat cttgtgtagg   3120
acaatagagg ctgaggtaaa tcgactttat gcttggaaat tggtaaatgg gcatatattt   3180
tcttttgcta gtcctctgtt gtggaaggct gagtcaacca gttaggaatg aaatggtggt   3240
tgggctcttt tgttgttatg gtaaacccct gaccaccaca gacttagaat tcctctagca   3300
ttaccttgtg tttaaggtgg ggttggttta ctacaaggat tctctcaata tttgctttat   3360
```

-continued

```
cctctgctct aggtctttct tttgaacttg tgcctcagcc ggggtctttc ttcacccttc   3420
tttgtccctt tccaagcaga agccgtctgt cacttggtgc tgctatagtg gtggtatagg   3480
ctggaagaga aagacaccct ctatggttct ggtcaagcct ccatcttaag tagacactgt   3540
ccctggattc tggtgggtgg gctgtctcgg gatttctgct ctcctccccc tgtaggtttc   3600
agcgtggaat ttatttttct cctttctcag gggtaaaagg cattttctgt tttcttcctt   3660
cagcagttcc agtgccttgc ggggaatgtc ttcaccagtg ctctaaaagg caacaggatt   3720
ttctgccctg tatccagcag cttaaggctt ttgtttcaaa agggaataag agagaaaaat   3780
ctctcctatc atgcttttct tgcggtactg ttgcctgttt ttaacttttt gtataaatgg   3840
aatcattcag tatgtacatt ttgtatctgt tttctttcac tctacagtat gtttgaaatg   3900
tttttatgtt gctttgtata tagttttctt cagatttctg aaagtatgac cgacaaataa   3960
aaattctata tatttagggc ataccatgtg atgtatatat ttacatatat atggaggcat   4020
aggggaatga ttaccacaat caagctaata aacatatcca acacctccca acatctctcg   4080
tagtcacttt ttattttttt atttttattt ttttggtgaa aacacttgtg atctagtctc   4140
ttaaaatatt ccaccagttg tggtggctcc tccctataat cccagagacc cagtaggcca   4200
aggcagaaga attgcttgag gccaagaggt caagaccagc ctctgccaca cagtgagaat   4260
tcatctctaa atttgtttta acaaattaac tgggtgtgga atcacacacc tgtagtccca   4320
gctacttgag agactgaggc agaaagattg cttgagccta gggggttgag gctacagcga   4380
gctatgatca tgctattgca ctccagcctg ggtgacagag tgagacaata tctcagtgaa   4440
atcaactata caacccatta ttattaacta tagtcaccat gctgtacatc atatctccag   4500
tgcttattca tcttatatcc aaaggtttgt atcctttgac aaatatctct ctttcttttc   4560
cttatctcca gaacctggcc accactattc cacctattct gttaccagga attcaatgtt   4620
tcttttagat tccacatatg agtgagatca tatagtattt gtctttgtgt gtcttgttta   4680
tttcacttag tataatgtcc acattgttgc aaatgatagg attcttttct tttcaaagac   4740
tgaaaaaaaa atttactttt attgcttctg taccatggct attgtgaata gtgctgcaat   4800
aaacatggag tgcaggtatc tttttgatat aatgatttta tttcatatgg attttatttt   4860
ctttataccc agaagtggta ttgctgcatt gtatcttagt tctatttgta atgttttgtg   4920
gaacttctaa actctttttc ataatggctc taccaactta catccctacc tagtaaggag   4980
gtcgaattcc cgatagcttt gactgacaca gctattcccc ctgccacttg cagttctccc   5040
aataaccgca gaatgtacca aaaaatatga catcttcaga taaggataac aaccttatcc   5100
ttatccgtgc ctctgttgct tagagaacag gatgttctcc agtgcttaca ctcagtgagc   5160
ccagatgagc ttcatctgcc atgagctgct tttctgagtc ttgggggact ggcttgccat   5220
ggatcctagg cttctgttta ttcttgctgc ctgtctgtaa ataatacatc tgcattcact   5280
gacttgtgtg agtgtcctgt ttcactggac tcatgcaggt ggtagagcta ctggggctct   5340
ttccctcctt tcagctgtcc t                                               5361
```

```
<210> SEQ ID NO 35
<211> LENGTH: 871
<212> TYPE: DNA
<213> ORGANISM: Homo sapiens

<400> SEQUENCE: 35

tagagtagga acataaatat caataccaac acaaggatct gagactaggc ttgcacccat     60
```

```
ggtaggggtg taaaacccat tcattttaag aaactttcac caaaccaaac taggaatagg    120

aggttactct cttaatctga tagagtatct actaaaaaag ctggagcaaa caccatccta    180

tcagtaaaac atgaaaagca ttccctttaa ccctatttag tttcaaatgg cagttatcta    240

ataaagttag cacataagga agagagaaac aatattgtaa aaggaaaaat ccagatgaat    300

ctacaaataa atgtttcata ggacaaaatt cagtaaggtg gtcagataca aaatcaaata    360

catttttata yggcagcaat aaacagacta tatacactat atacccattt atttaataat    420

cacaacaaaa atacaaagaa cctcggagta aattttttaa aaagacttat aagaccttta    480

tttagaaaac aatttaaact ttgtaaaata cctcaataat agtaaagagg tatcatgttc    540

agaggtatta taaaactatg aattatcttc aaatttatcc acagattcaa tgcaatctca    600

aataaaattt atcttattta tttatttatt ttttgagatg gagtctcact ctgttaccca    660

ggctggagtg cagtggcgtg atcttgactc actatgacct ctgtctcctc gtttcagact    720

attctcctgc ctccacctcc tgagtagctg ggattacagc catgtgccac cactatgccc    780

agctaatttt tttttttttt tttttttttt tttttagtac agacggggtc tcaccatgtt    840

ggccaggctg gtcttgaact tctgacctca a                                   871
```

<210> SEQ ID NO 36
<211> LENGTH: 701
<212> TYPE: DNA
<213> ORGANISM: Homo sapiens

<400> SEQUENCE: 36

```
acttgaagtt tgagaattga aaagcagaat taaaaattca gaagaaccca ttggaaatct     60

ttacaatcac taagagagac cagagatctc tctcacaaaa tacggcataa aagaataggt    120

aaaaatgtgt ctatgatgtt ccaagagaaa atgaagagaa ggttgagaag atgtatccaa    180

caatattaaa gaatacaact kattgaattg atcaaagatc aaagatatga atcatcttac    240

agggtctatc cagtgtcgag aataataaaa cacaaacaca tttacacata tatatactta    300

ttaaactcat tgtaataaaa cctaaaacta ccaaaagaga tacagattac taaaaatttc    360

cagagacaga ggggcagaac tcctttttaa tcatacaaat gaatgggagt tagtttgcta    420

ttagtcttct gttacggact aaatgcgctc ctaagattcc tatgttgaag tctaaagctg    480

acactcccaa tctgatggaa tttggaagta gggtttttgg gagataatta agtttagata    540

aagtcatgag attcaggcgg gcccccatga tgggatgaga ttagtgtcct tataagaaga    600

gagggccggg cgcggtggct catgcctgta atcccagcac tttgggaggc cgaggcagac    660

agatcacgag gtcaagggat caagaccatc ctggccaaga t                        701
```

<210> SEQ ID NO 37
<211> LENGTH: 1001
<212> TYPE: DNA
<213> ORGANISM: Homo sapiens

<400> SEQUENCE: 37

```
ggcacagtgg ctcatgccta taatcccagc actttgggga ggctgaggca ggcggatcgc     60

ctgaggtcag gagtttgaga ccagcctgga caacatggtg aaacccccat ttctactaaa    120

aatacaaaaa ttagccagat gtgatgacat gcatctgtga tcccagctac ttgggaggct    180

gaggcatgag aatcacctga acctgggagg tgcaggttgc agtgagccga gatcgtgcca    240

ctgcactcca gcctgggcaa cacagcaaga ctctgtctca aacaaaaaaa gaaaaagaaa    300

aattaaaccc cacctcccca gacccatcct tcctgggtta atctaatatg cttctctaca    360
```

```
tgttcatgca acatacatgt acacatgttc aacacatatg gtgtttttgc atttctttct    420

ttttcttttt caaaaacaaa aatgaaatca ctctcaaaca ctacttggtg acttgccttt    480

ttttttgct taaactttgc rtatgttggc cattaccaga ctgatccata tatgtctact    540

cactctgttt aatagctata taatgtctga gaatatggat atacaattat ttgttcaatc    600

agcatcctct tttgacggaa gtaatttcca ggtttttcat cttgacacac aattccacaa    660

tgaaaatttt gagacagatg tcatttagta ccactggggc ttttcttgta aagcgtagat    720

tacaagcatt gccatttctg ggccaaagga tatgtgtgtt ttaagatgta atatatccag    780

gccagacatg aaaggacaaa tactgtatga ttccacttat atgaggcagc tagaatagcc    840

caatttatag agacagaaag tagaaaagtg tttgccaggg gctgggagtg gacgggaatg    900

gggagttggt gtttagtggg gacagaactt ctatctggga agatgaaaac gttgtggagg    960

cagatggtga tgatggttgc acaacatggt gaatgcactt a                        1001
```

<210> SEQ ID NO 38
<211> LENGTH: 550
<212> TYPE: DNA
<213> ORGANISM: Homo sapiens

<400> SEQUENCE: 38

```
atatttaaat ggcattgtct taaactacat tctacagaga attaatgtcy cataaaatgg     60

tagtaaattt tcattaaaaa tgaaaaaaaa tcgatactaa tgatatgatt tactaaaata    120

tttaaatata tatgcattta aatatatatg caagaaaaat attaggcatg tataaatagt    180

agttattatt tgagatttac tttgaagata taatctgcta tacttgagaa tgccaggaag    240

taacatgagt gcataccaaa tgcttgtacg tttagtgttg ccactgacca ttcactgagc    300

atcacctgtg aatgatctac tcaatggtca catgaagggc ttgtatctta taatgtccac    360

atacatttga aatatattta acttttacat ataaataaat cataaatcaa attttaagtt    420

tttcatcaac taatttgcct ttgagactat ctattcttat ctacttattt ttgtcatttg    480

cgaaaatata ctcagctgat ctcacttatt atatttacag atcaacttta ggttaagatt    540

gttgagatcc                                                           550
```

<210> SEQ ID NO 39
<211> LENGTH: 1932
<212> TYPE: DNA
<213> ORGANISM: Homo sapiens

<400> SEQUENCE: 39

```
ccccttggaa aaaaaaacca cgcacacaaa caccatcctg cctttttttt tttcagggct     60

catctctgga cccacacccc ataaccaaca tggaagcctg gatttggccc tggatcaggc    120

tggctcccca gggaagggtc cagtctctcc ggggagacat cccgacttcg ggtcctgctt    180

tctctactgt aattcgaggc yggccatgcc cctcagtggg cctcagtttc ctcacctgta    240

cagtggggaa atccatagga cctacctcct gggagggcac tgaggaccga gggaatgaat    300

gcctgtccag tgctcatgat cgtgacaagc actgcgcaga ataaatccgg aataaacgct    360

caccgggtga gggagggcag ggaagatttc taaaatcccc ctgatttgag atgagatctg    420

attcacccac ttaaaaaacc acattgggaa ataatttgaa atgtacagga aagttgtaag    480

aatcgcacaa agaatactcc caaacgtttt gcccatactc acctgttttc tgtggcaact    540

ttgagacaga attcacacgc catacagttg acccatctca actgtacaat tcaatggcct    600
```

```
ttcatagtca gagttgtgca actgtcacca gggtcaattt tagaacgttt tcatcactct    660

cctctcacaa aaaacccctc acgtcccttg gctgtcactc tgcacctatt aatatttttt    720

tgtgttaaga ctttttcttt gagatggagt ctcagtctgt tgcccaggct ggagtgcagt    780

ggcgtacatc tcggctcaca gtaacctcca cctcctgggt tcaagcgatt ctcctgcctc    840

agcctcctga gtagctggga ttacgggtgc ccgcctccac gcccggctag tttttgtatt    900

tttagtagag acagggtttc accatgttgg tcaggctggt ctcgaactcc tgacctcgtg    960

atccacctgc cttggcccca caaagtgcta ggattacagg tgtgaaacac tatgcccggt   1020

aaatgttaag acttttatgc atcttcttga cctgtggtct tcagcatttg agtcttaggg   1080

gacctttaaa atattaagat aggccaggca cagtggctca tgcctgaaat cccagaactt   1140

taggaggctg tggtgagacg attgcttgaa gccaggagtt tgggacgagc ctgggcatca   1200

tagtgagacc cccatcttgg caaaaaagta aacataaaaa atattagctg ggcatagtgg   1260

cgagcatctg tagttctagc taattgggag gctgaggtgg caggatccct tgagcccaag   1320

agttcaagag tatagtgagc tatgattgtg ccactgcact ccagcctggg caatagagtg   1380

agaccctgtt tctaaaaaac aaaagccata ctaaaatact ctgcaaagac ctcatattca   1440

tttattcact caacaaatgt ttgttgagca cctgttttat gccaagtcca atactaggag   1500

ctctggttgc aacagagagc aaaacagaca cggccctgcc agtcacctgg ggcagggaat   1560

ccccctgccc cactccctgc aataatcgat tgtagagaag aattagcaaa tcacagctga   1620

gaagggtctg ctggaaaaca cagcagaggc cttgactttg cctgatgaat ggaggtgggc   1680

ttcctggcag aggggcgtct gtgggtgagg gaggaagtag gactggctgg tcagagggga   1740

cggcacacag gaagctgctg agcaggcagg agtgtgctcc gtggaggagc taggaggagg   1800

ccagttctta gctggagggt ggagaaggag ggctaaagcc aagcatgcag aggccgaggg   1860

atgtgcagcg ccggtcagcc cacgtgagat ctttcctccc tctccgtgga ctgggaacct   1920

ccatagttac ca                                                       1932
```

<210> SEQ ID NO 40
<211> LENGTH: 874
<212> TYPE: DNA
<213> ORGANISM: Homo sapiens

<400> SEQUENCE: 40

```
ttccctcccc cagaagtagc cactatccta acttgtggaa accgttttct ttctttcctc     60

tttagtgtta caactaaatg tgccccataa acaagcatca gtttgtgaat atcatataaa    120

tggaattaga ccgggtgtgg aggttcatgt ctgtaatagc actttgggag gccaaggcag    180

gtggatcacc tgaggtcagg agttcgagac cagcctggcc aatgtggtaa aaccctgccg    240

ctactgaaaa tacaaaaaaa ttagctgggc atggtggcag gcacctgtaa tctcagccac    300

tcgggaggtt gaggcaggag aattgcttga acactgtgga ggttgcagtg agccgaaatc    360

acgccactgc atgccagcct gggcaacaga ggaagaccct gtctcaaaaa aaaaaaaaaa    420

aaaaaaaaga aaaagaaaaa ggaatgatat tgtatatatt ctttgtgact tgtttcttcc    480

tcacaattgt tcttagacaa kgtgtgaaga ggccttttg gtgcctgctg atgttttccg     540

ggatggtgga ttcaggagta tgctgtcttc acaaacattt ctggcctcaa agtcacattg    600

agcagcttgg gcctcctagc tcagccactt agtgtgtgac ctttcttgtc ctcctttgta    660

aaatcagaac aaattattcc tgtagacatg agcacctcaa gagcaggagt gttcctcatt    720

tgccattctg ttctctagaa cttgcagtgc ctggtgccta atgaatcctg agtgaacaca    780
```

```
ggagacatgg tgagatcatg tatgtaaggg cctaatacca cccctgattt atagcaactg    840

ctcaatacat gggagccaat cttattattg ccac                                874


<210> SEQ ID NO 41
<211> LENGTH: 701
<212> TYPE: DNA
<213> ORGANISM: Homo sapiens

<400> SEQUENCE: 41

cactacagca agtggcaaca ggtggggagg tggtccagat gtctttcggc ttcagagttg     60

gtcctggact tgggttctgg agtctcccca gtgaccagga tttctcagag gggtcccag    120

gtatggacac tgcagaccct cctgtgacta ggagttctta gaggaggtcc tgggcatggg    180

cactggagtc cctcccatga mtagaaattc tcagaggagt tcctgggcat gggcactgga    240

gtcccttctg tgactaggtg gtcctgggca tgagtgctgg agaccttcca gtagctagga    300

gttcttgttg acttgggcga ctgcagaaca ccacaaggca ttgattgatt gattgattga    360

ttgagatgga gtcttgctct gtcgcccagg ctggagtgca gtggcgcaat cttggctcac    420

tgcaacctcc gcctcccggg ttcaagtgat tctcctgtct cagcctcctg aatagctggg    480

actacaggtg catgccctca tgcctggcta atttttgta tttttagtag agacagggtt    540

tcaccgtgtt agccaggatg gtcttgctgt cctgaccttg tgatccgcct gcctcggcct    600

ccaaaagtcc tgggattaca ggaatgagcc accgcgcttg gccttatttt ttattctcca    660

agcccaacca agatttccag acatggtggc ctcctgagca c                        701


<210> SEQ ID NO 42
<211> LENGTH: 801
<212> TYPE: DNA
<213> ORGANISM: Homo sapiens

<400> SEQUENCE: 42

acagagcttg acacatccaa caaggatgga ctttaattta actcaattaa ttttttaga      60

ggtagattct tccctatgtt gcctgagctg gatttgaact cctgggctca tgcaatcctc    120

ctgccttggc ctcccaaata gccggactac aggtgcacac caccatgccc agttctagac    180

ctaatttgat caaatgggat gcccatcctg taaaggctcc gccgtggcct ggtgtctctc    240

atgtctcagg gaggccctag gggctgaccc acctcgaagg aagaaggtgt cgtgctggtc    300

acgggctggg tgctgctggg gctggaagag ggcgtcaaag ttccagaagg agctctcaat    360

gaagttatca gtcggcatct cggtgaacct ggtgggagac rcagcctgac tgccctgcct    420

gtacccagca gaagcaccag gcaccgcccc cagccctgtg ctcaccccat ctccaggaag    480

atctgtcgga actgggagcg gaccttgagc agcgggtgaa ggtggccgct gtcggggagg    540

acaccgtggg ccaagaagtt gtagggcttg aagggccggt cccgccaaga gccactgggg    600

gaggatgcaa gggcctggta agggctgccc gcccctgccc cctgccccag ctcccacctg    660

ccctgaccct ggggttgcct gctacctgga gatcatctct gggctcagct ctgtctcttg    720

cttggagatg ctggtactaa aggcactgcc tttgctcacc cagtaggtct tcagagtcct    780

gtggccaggg gaaggaaggg g                                              801


<210> SEQ ID NO 43
<211> LENGTH: 801
<212> TYPE: DNA
<213> ORGANISM: Homo sapiens
```

<400> SEQUENCE: 43

```
cacagttcca agataagata tcatttcccc attgttaaat ctatgtgcaa agctaactta      60
tgattaaatt atggtaagct taactgtaat acaaggaatc atttcatact atttgtaaag     120
cagtgaacac tagcgtaata agttatgatc gtggaggcta ccacctgcac catccatacc     180
ccgagggctg gacactcata actatgggtg aggccattcc ttccgctggg gcaagaataa     240
ctatagatgc ctatgggaaa ctgatacaat ctcattctct acacttcctt tatatgctga     300
aggtcacaat ctttattctt gcttagtgaa gagagaatcg actgagctac atccacacac     360
tattcaccat aatgagaatt ggaatattac ttcaaattct kcagtcaccg aagcaaaatc     420
tgtaacaggg tggatttcaa aaattatttt ttatcaaggc ataacctcat ttattttagg     480
ttcatggatg taattttatt ctccaaggta accttatctt caaattttat aggtctcatg     540
ctgtccccca tcctgtatca cctacaggtg acttttcctt gatatgactt atagaacatt     600
aacagtgctt tcttttcaat catactccga tttggttagt tccaacttag gggacactta     660
ctttaaaatg tctcttcacc ctgcaggaaa cgagtttatt agtgaaactt tcaacggata     720
tttttattcc atttatgcca tttatctctc catgccttgt gaggcaaagg agtggtgttt     780
caccaggtta agaggtaatt g                                               801
```

<210> SEQ ID NO 44
<211> LENGTH: 201
<212> TYPE: DNA
<213> ORGANISM: Homo sapiens

<400> SEQUENCE: 44

```
tattcacttt attgtgatat ctgctttatt gtggtggtct ggaaccaaac caacagtaac      60
tccaagaggt gcctggacta ccacaatcca ccagcatgcg ygaatatcaa ctgacaagca     120
atattgaaaa atatagtcac ttttctttaa tttcttttga aaagaactaa tcatattaga     180
agtaaaaagt tattctgaaa a                                               201
```

<210> SEQ ID NO 45
<211> LENGTH: 807
<212> TYPE: DNA
<213> ORGANISM: Homo sapiens

<400> SEQUENCE: 45

```
ccggtcttgg gtggccggaa ccacatccta ggtaaggacc ctgccctccc tgctctcaga      60
gccctgggga atgcgcaggt gatgaggagg aaagagttgg agccctgggt cccagtcctg     120
gctttgtcac tgacctgcca gggaacccaa gggcctcaat ttccagatct gcaaaatggg     180
caccctcggt cttttgtata ttatgtctgt caaacagccg atgcccgacc tgagggagaa     240
ccaaagccca ctcagccagg gacccaaacc atgtcagctc atggatgttt tgtgtttatt     300
ttgctcrtct gtggtccttt ttaagacaat gccgttaatt ttggggacaa aatttcttgc     360
tctgataatc aaaaataatt attccagcta ggcacagtga ctcacgcctg taatcccagc     420
gctctgggag gctgaggcag acagatcacc tgaggtcagg agttcgagac cggcctggac     480
aacatggtga aactctgtgt ctactaaaaa catagattgg acgggtgtgg tggtgggcga     540
ctgtagtcct agatactccg gaggctgagg caggagaatt gcttgaatct gggaggtgga     600
gattgcagtg aactgagatt gttccactgc actccagccc agaaaacagt gtgagactcc     660
atctccaaaa taataataat aataatttca tcagcggcag aaaattgtaa tctgtctaac     720
atgactaaga aaagctccta cctgggggca gggacataag gactcaaaga gatggtgcag     780
```

gagtgctgtg tacagggcct ggcgctt 807

<210> SEQ ID NO 46
<211> LENGTH: 501
<212> TYPE: DNA
<213> ORGANISM: Homo sapiens

<400> SEQUENCE: 46
aatcctcata atgattaaaa agaaaagact aaaaaagaag aggaaaagta gaagatgaat 60
tagatacaaa agaatattat attactggct tagtcactta ttctaaaacc taccccttcc 120
atatggaata ttgtaccagg gcacctgaat cagatgtgca tagactctga cactatcttg 180
tcttcacttc accaatggag ttcattatgt gagatttgta gtccaaaaca actctcagaa 240
gcaaatcttc raaatatgca agaatttggt ttggaatgag ttaatttcca tgctttggct 300
aaagtagcag aacaagaaat gataggcata gtacagagaa tggagaaatt aagctcattc 360
cagaaagcag caagctctac tagaaagaaa actgagaggg tacgaacttc ttattttagg 420
ctatcaatcg acacagcagg gcattttcac ctaattttat ggattaagga tttgaaaatg 480
aaagcacgct gaagggctag t 501